United States Patent [19]

Summers et al.

[11] Patent Number: 5,459,152
[45] Date of Patent: Oct. 17, 1995

[54] PLATELET ACTIVATING FACTOR ANTAGONISTS

[75] Inventors: James B. Summers, Libertyville; Steven K. Davidsen, Mundelein; James H. Holms, Gurnee; Daisy Pireh, Lincolnshire; H. Robin Heyman, Chicago; Michael B. Martin, Waukegan; Douglas H. Steinman, Morton Grove; George S. Sheppard, Wilmette; George M. Carrera, Jr., Des Plaines, all of Ill.

[73] Assignee: Abbott Laboratories, Abbott Park, Ill.

[21] Appl. No.: 162,034

[22] PCT Filed: Jul. 14, 1992

[86] PCT No.: PCT/US92/05890

§ 371 Date: Dec. 2, 1993

§ 102(e) Date: Dec. 2, 1993

[87] PCT Pub. No.: WO93/01813

PCT Pub. Date: Feb. 4, 1993

[51] Int. Cl.$^6$ .................. C07D 513/04; A61K 31/44
[52] U.S. Cl. .............. 514/338; 514/339; 514/233.2; 514/33; 514/256; 546/270; 546/273; 546/256; 544/131; 544/333
[58] Field of Search ................... 546/270, 273; 514/338, 339

[56] References Cited

FOREIGN PATENT DOCUMENTS

| 0297987 | 1/1989 | European Pat. Off. | ...... C07D 513/04 |
| 0327417 | 8/1989 | European Pat. Off. | ...... C07D 513/04 |
| 0425134 | 5/1991 | European Pat. Off. | ...... C07D 513/04 |

OTHER PUBLICATIONS

*Chem. Abstr.*, 1156: 280013z (1991).
*Chem. Abstr.*, 116: 255603e (1992).
D. Lave, et al., *Drigs of the Future*, 14(9): 891–898 (1989).
D. Lave, et al., *J. Pharm. Belg.*, 45(3) 219–223 (1990).
F. Soler, *Drugs of the Future*, 17(3): 207–213 (1992).

*Primary Examiner*—Jane Fan
*Attorney, Agent, or Firm*—Jerry F. Janssen

[57] ABSTRACT

Indole compounds substituted at the 3-position by a 7-carbonyl(pyridin-3-yl)pyrrolo[1,2-c]thiazole, 7-carbonyl(pyridin-3-yl)pyrrolo[1,2-c]oxazole, or 7-carbonyl(pyridin-3-yl)pyrrolo[1,2-c]pyrrole group are potent antagonists of PAF and are useful in the treatment of PAF-related disorders including asthma, shock, respiratory distress syndrome, acute inflammation, transplanted organ rejection, gastrointesinal ulceration, allergic skin diseases, delayed cellular immunity, parturition, fetal lung maturation, and cellular differentiation.

7 Claims, No Drawings

PLATELET ACTIVATING FACTOR ANTAGONISTS

This application is A 371 of PCT/US92/05890 Jul. 14, 1992 now WO/93-01813 Feb. 4, 1993. This application is a continuation of Ser. No. 07/731,681 Jul. 1, 1991 now abandoned.

TECHNICAL FIELD

This invention relates to compounds having pharmacological activity, to compositions containing these compounds, and to a medical method of treatment employing the compounds and compositions. More particularly, this invention concerns certain indolecarbonyl pyridylpyrrolothiazole compounds and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

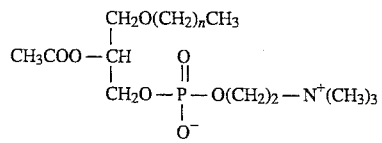

where n is 15 or 17.

PAF is physiologically active and causes contraction of the airway smooth muscle, increased vascular permeability, platelet aggregation, hypotension, and the like. It is now recognized as a powerful mediator of inflammation and may play a physiological or pathobiological role in a variety of clinical conditions, such as asthma and pulmonary dysfunction, acute inflammation, transplanted organ rejection, shock, thrombosis, anaphylaxis, gastrointestinal ulceration, allergic skin diseases, retinal and corneal diseases, chemically induced liver cirrhosis, and ovimplantation in pregnancy.

Several PAF antagonists have been reported (e.g. U.S. Pat. No. 4,948,795, European Patent Application EP 279681, and U.S. Pat. No. 4,786,645) but none have received wide acceptance. Therefore, there is a continuing need for the development of potent, orally active antagonists of PAF.

SUMMARY OF THE INVENTION

The present invention provides, in its principal aspect, compounds having PAF antagonsist activity of the formula:

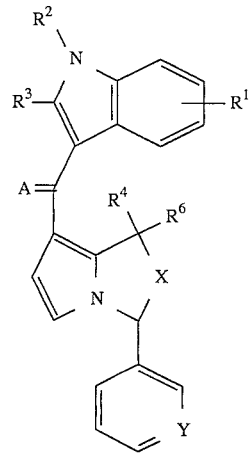

or a pharmaceutically acceptable salt thereof.

In the formula given above, $R^1$ is one or more groups independently selected from the group consisting of (A) hydrogen; (B) halogen; (C) alkyl of from one to six carbon atoms; (D) alkoxy of from one to six carbon atoms; (E) alkoxy of from one to seven carbon atoms; (F) phenyl, optionally substituted by (1) alkyl of from one to six carbon atoms, (2) alkoxy of from one to six carbon atoms, or (3) halogen; (G) $NR^7R^8$ where $R^7$ and $R^8$ are independently selected from (1) hydrogen, and (2) alkyl of from one to six carbon atoms, or (3) taken together with the nitrogen atom to which they are attached form a saturated 5- or 6-membered nitrogen-containing ring; (H)-$COOR^9$ where $R^9$ is independently selected from (1) hydrogen, and (2) alkyl of from one to six carbon atoms, (I)-$CONR^7R^8$ were $R^7$ and $R^8$ are as defined above; (J) -$SO_2NR^7R^8$ where $R^7$ and $R^8$ are as defined above; (K) 2- or 3-furyl, (L) 2- or 3-thienyl, (M) 2-, 4-, or 5-thiazolyl, (N) 2-, 3-, or 4-pyridyl, (O) 2-, or 4-pyrimdyl, (P) benzoyl, wherein the phenyl moiety is optionally substituted by (1) halogen, (2) alkyl of from one to six carbon atoms, or (3) alkoxy of from one to six carbon atoms; (Q) phenoxy optionally substituted by (1) halogen, (2) alkyl of from one to six carbon atoms, or (3) alkoxy of from one to six carbon atoms; (R) phenylalkyloxy in which the alkyl portion contains from one to six carbon atoms and the phenyl is optionally substituted with (1) halogen, (2) alkyl of from one to six carbon atoms, or (3) alkoxy of from one to six carbon atoms, and (S) phenylalkoyl in which the alkoyl portion contains from one to seven carbon atoms and the phenyl moiety is optionally substituted by; (1) halogen; (2) alkyl of from one to six carbon atoms, or (3) alkoxy of from one to six carbon atoms.

The substituent group $R^2$ is selected from the group consisting of (A) hydrogen, (B) alkyl of from one to six carbon atoms; (C)-$(CH_2)_pCOOR^9$, where p is 0 or an integer of from 1 to 4 and $R^9$ is as defined above, (D) -$(CH_2)_qNR^7R^8$, where q is an integer of from 2 and 4 and $R^7$ and $R^8$ areas defined above, (E) -$(CH_2)_pCOR^9$ where $R^9$ is as defined above; (F) -$(CH_2)_qOH$ where q is as defined above; (G) -$(CH_2)_pSO_2R^9$ where p and $R^9$ are as defined above, (H) -$(CH_2)_pSO_2NR^7R^8$ where p, $R^7$ and $R^8$ are as defined above, (I) -$(CH_2)_pCONR^{10}R^{11}$, where p is as defined above and $R^{10}$ and $R^{11}$ are independently selected from (1) hydrogen, (2) alkyl of from one to six carbon atoms, (3) -$(CH_2)_rCOOR^9$, where r is an integer of from 1 to 4 and $R^9$ is as defined above, (4) -$(CH_2)_rNR^7R^8$ where r, $R^7$ and $R^8$ are as defined above, (5) -$(CH_2)_rOH$, (6) -$(CH_2)_rSO_2R^9$ where r and $R^9$ are as defined above, (7) -$(CH_2)_rSO_2NR^7R^8$ where r, $R^7$ and $R^8$ are as defined above, (8) -$(CH_2)_pCN$ where p is as defined above; (9) -$(CH_2)_p$-1H-tetrazol-5-yl where p is as defined above; (10) -$CONHNH_2$, and (11) -$(CH_2)_r$-phenyl, where r is as defined above and the phenyl moiety is optionally substituted by halogen, alkyl of from one to six carbon atoms, or alkoxy of from one to six carbon atoms.

The groups $R^3$, $R^4$, and $R^5$ are independently selected from hydrogen or alkyl of from one to six carbon atoms.

X represents an atom or group of atoms selected from the group consisting of S, SO, $SO_2$, O, and $CH_2$.

Y represents an atom or group selected from the group consisting of (A) N, (B) $N^{30}$-$R^{12}$ where $R^{12}$ is an alkyl group of from one to six carbon atoms, (C) $N^+ \rightarrow O^-$, (D) $N^+$-$OR^{12}$ where $R^{12}$ is as defined above, (E) $N^+$-$NR^7R^8$ where $R^7$ and $R^8$ are as defined above, (F) $N^+$-$NHCONR^7R^8R^7$ and $R^8$ are as defined above, (G) $N^{30}$-$NHCOR^9$ where $R^9$ is as defined above, (H) $N^+$-$CR^7R^8OCOR^{12}$ where $R^7$, $R^8$ and $R^{12}$ are as defined above, (I) $N^+$-$OCR^7R^8$ $OCOR^{12}$ where $R^7$, $R^8$ and $R^{12}$ are as defined above, (J) $N^+$-$CR^7R^8OCONR^7R^8$ where $R^7$ and $R^8$ are as defined above, and (K) $N^+$-O-$CR^7R^8OCONR^7R^8$ where $R^7$ and $R^8$ are as defined above.

A represents O, $N^+OR^{10}$, $N+OCOR^{10}$, or $N^+NR^7R^8$, where where $R^7$, $R^8$ and $R^{10}$ are as defined above.

The pharmaceutically acceptable salts and individual stereoisomers of compounds of structural formula I above, as well as mixtures thereof, are also contemplated as falling within the scope of the present invention.

In another aspect, the present invention provides pharmaceutical compositions useful for the treatment of PAF-mediated disorders comprising a therapeutically effective amount of a compound of formula I above in combination with a pharmaceutically acceptable carrier.

In another aspect, the present invention provides a method of inhibiting PAF activity by administering to a host mammal in need of such treatment an effective amount of a PAF-inhibiting compound having structure I above.

In yet another aspect of the present invention, there is provided a method of treating PAF-mediated disorders including asthma, shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION AND PREFERRED EMBODIMENTS

In a preferred embodiment, compounds of the present invention are represented by formula I wherein:

$R^1$ is phenyl, optionally substituted by (a) alkyl of from one to six carbon atoms, (b) alkoxy of from one to six carbon atoms, or (c) halogen; $R^2$ is as defined above; $R^3$, $R^4$, and $R^5$ are hydrogen; X is -S-; Y is selected from the groups consisting of (a) -N-, (b) >N-O, (c) >N-$CR^7R^8OCOR^{12}$ or (d) >N-$OCR^7R^8OCOR^{12}$; A is selected from the groups consisting of (a) =O, or (b) =NOH. Preferred compounds of Formula I are those in which X is -S-, -SO-, or -$SO_2$-; $R^2$ is hydrogen, carbamoyl, alkyl of from one to six carbon atoms, -$COOR^8$, or -$SO_2R^8$; $R^3$ is hydrogen or alkyl of from one to six carbon atoms; and $R^1$ is hydrogen, phenyl, or phenylalkoxy or a pharmaceutically acceptable salt thereof.

In a particularly preferred embodiment, compounds of the present invention are represented by Formula I wherein $R^1$ is phenyl or 4-fluorophenyl; $R^2$ is $CONH_2$. $CONHCH_3$, or $CONH(CH_3)_2$; and $R^3$, $R^4$, X, Y, and A are as defined immediately above.

Examples of compounds contemplated as falling within the scope of the present invention include, but are not necessarily limited to:

3-(pyridin-3-yl)-7-(indol-3-yl)carbonyl-1H,3H-pyrrolo [1,2-c]thiazole;

3-(pyridin-3-yl)-7-(1-N,N-dimethylcarbamoylindol-3-yl)carbonyl-1H,3H-pyrrolo[ 1,2l -c]thiazole;

3-(pyridin-3-yl)-7-(5-phenylmethoxyindol-3-yl)carbonyl-1H,3H-pyrrolo[ 1,2-c]thiazole;

3-(pyridin-3-yl)-7-(6-phenylmethoxyindol-3-yl)carbonyl-1H,3H-pyrrolo[ 1,2-c]thiazole;

3-(pyridin-3-yl)-7-(7-phenylmethoxyindol-3-yl)carbonyl-1H,3H-pyrrolo[ 1,2-c]thiazole;

3-(pyridin-3-yl)-7-(1-N,N-dimethylcarbamoyl-5-phenylmethoxyindol-3-1)carbonyl- 1H,3H-pyrrolo[1,2-c]thiazole;

3-(pyridin-3-yl)-7-(1-N,N-dimethylcarbamoyl-6-phenylmethoxyindol-3-yl)carbonyl- 1H,3H-pyrrolo[1,2-c] thiazole;

3-(pyridin-3-yl)-7-(1-N,N-dimethylcarbamoyl-7-phenylmethoxyindol-3-yl)carbonyl- 1H,3H-pyrrolo[1,2-c] thiazole;

3-(pyridin-3-yl)-7-(1-tert-butyloxycarbonylindol-3-yl)carbonyl-1-H,3H-pyrrolo( 1,2-c]thiazole;

3-(pyridin-3-yl)-7-(6-phenylindol-3-yl)carbonyl-1H,3H-pyrrolo[1,2-c]thiazole;

3-(pyridin-3-yl)-7-[1-(morpholin-4-ylcarbonyl)indol-3-yl]carbonyl-1H,3H-pyrrolo[ 1,2l -c]thiazole;

3-(pyridin-3-yl)-7-(1-N,N-dimethylcarbamoyl-6-phenylindol-3-yl)carbonyl- 1H,3H-pyrrolo[1,2-c]thiazole;

2-oxide-3-(pyridin-3-yl)-7-(1-tert-butyloxycarbonylindol-3-ylcarbonyl)- 1H,3H-pyrrolo[1,2-c]thiazole;

2-oxide-3-(pyridin-3-yl)-7-(indol-3-ylcarbonyl)-1H,3H-pyrrolo[1,2-c]thiazole;

3-(pyridin-3-yl)-7-(indol-3-ylcarbonyl)-1H,3H-pyrrolo [1,2-c]oxazole;

3-(pyridin-3-yl)-7-(1-N,N-diisopropylcarbamoyl-6-phenylmethoxyindol-3-ylcarbonyl)- 1H,3H-pyrrolo[1,2-c] thiazole;

1,1-dimethyl-3-(pyridin-3-yl)-1-(indol-3-ylcarbonyl)-1H, 3H-pyrrolo[1,2-c] thiazole;

3-(pyridin-3-yl)-7-(1-carbomethoxycarbamoyl-6-phenylmethoxyindol-3-ylcarbonyl)- 1H,3H-pyrrolo[1,2-c] thiazole;

1,1-dimethyl-3-(pyridin-3-yl)-7-(1-N,N-dimethylcarbamoyl-indol- 3-ylcarbonyl)-1H,3H-pyrrolo[1,2-c]thiazole;

3-(pyridin-3-yl)-7-(1N-methyl-N-phenylcarbamoyl-6-phenylmethoxyindol- 3-ylcarbonyl)-1H,3H-pyrrolo[1, 2-c]thiazole;

3-(pyridin-3-yl)-7-(1-methyl-6-phenylmethoxyindol-3-ylcarbonyl)- 1H,3H-pyrrolo[1,2-thiazole;

3-(pyridin-3-yl)-7-(1-N-methylcarbamoyl-6-phenylmethoxyindol- 3-ylcarbonyl)-1H,3H-pyrrolo[1,2-c] thiazole;

2-oxide-3-(pyridin-3-yl)-7-(1-N,N-dimethylcarbamoyl-6-phenylindol-3-ylcarbonyl)- 1H,3H-pyrrolo[1,2-c thiazole;

1,1-dimethyl-3-(pyridin-3-yl)-7-(1-N,N-dimethylcarbamoyl-6-phenylindol- 3-ylcarbonyl)-1H,3H-pyrrolo[1,2-c]thiazole;

1,1-dimethyl-3-(pyridin-3-yl)-7-[6-(4-methoxyphenyl)indol-3-ylcarbonyl]- 1H,3H-pyrrolo[1,2-c]thiazole;

1,1-dimethyl-3-(pyridin-3-yl)-7-(1-N,N-dimethylcarbamoyl- 6-(4-methoxyphenyl)indol-3-ylcarbonyl]-1H,3H-pyrrolo[1,2-c]thiazole;

3-(pyridin-3-yl)-7-(1-carbophenoxy-6-phenylmethoxyindol-3-ylcarbonyl)- 1H,3H-pyrrolo[1,2-c]thiazole;

3-(pyridin-3-yl)-7-[6-(4-fluorophenyl)indol-3-ylcarbonyl]- 1H-3H-pyrrolo[1,2-c]thiazole;

3-(pyridin-3-yl)-7-[1-N,N-dimethylcarbamoyl-6-(4-fluorophenyl)indol- 3-ylcarbonyl]-1H,3H-pyrrolo[1,2-c]thiazole;

3-(pyridin-3-yl)-7-[1-N-methylcarbamoyl-6-phenylindol-3-ylcarbonyl)- 1H,3H-pyrrolo[1,2-c]thiazole;

3-(pyridin-3-yl)-7-[1-N-methylcarbamoyl-6-(4-fluorophenyl)indol- 3-ylcarbonyl]-1H,3H-pyrrolo[1,2-c]thiazole;

1,1-dimethyl-3-(pyridin-3-yl)-7-[1-N-methylcarbamoyl-6-(4-methoxyphenyl)indol-3-ylcarbonyl]-1H,3H-pyrrolo[1,2-c]thiazole;

3-(1-methylpyridin-3-yl)-7-(1-N,N-dimethylcarbamoyl-6-phenylindol-3-ylcarbonyl)- 1H,3H-pyrrolo[1,2-c]thiazole;

3-(1-oxide-pyridin-3-yl)-7-(1-N,N-dimethylcarbamoyl-6-phenylindol-3-ylcarbonyl)- 1H,3H-pyrrolo[1,2-c]thiazole;

3-(1-oxide-pyridin-3-yl)-7-(1-N-methylcarbamoyl-6-phenylindol-3-ylcarbonyl)- 1H,3H-pyrrolo[1,2-c]thiazole;

1,1-dimethyl-3-(pyridin-3-yl)-7-[6-(4-fluorophenyl)idol-3-ylcarbonyl]- 1H,3H-pyrrolo[1,2-c]thiazole;

3-(pyridin-3-yl)-7-(1-N-methylcarbamoyl-6-phenylmethoxyindol-3-ylcarbonyl)- 1H,3H-pyrrolo[1,2-c]thiazole;

3-(pyridin-3-yl)-7-[6-(4-methoxyphenyl)indol-3-yl]carbonyl- 1H,3H-pyrrolo[1,2-c]thiazole;

3-(1-oxide-pyridin-3-yl)-7-[1-N,N-dimethylcarbamoyl-6-(4-fluorophenyl)indol-3-ylcarbonyl]-1H,3H-pyrrolo[1,2-c]thiazole;

3-(pyridin-3-yl)-7-[1-N,N-dimethylcarbamoyl-6-(4-methoxyphenyl)indol- 3-ylcarbonyl]-1H,3H-pyrrolo[1,2-c]thiazole;

3-(pyridin-3-yl)-7-(6-pyrid-3-ylindol-3-ylcarbonyl)-1H,3H-pyrrolo-[ 1,2-c]thiazole;

3-(pyridin-3-yl)-7-(1-N,N-dimethylcarbamoyl-6-pyrid-4-ylindol-3-ylcarbonyl)- 1H,3H-pyrrolo[1,2-c]thiazole;

3-(pyridin-3-yl)-7-[1-N-methylcarbamoyl-6-(4-methoxyphenyl)indol- 3-ylcarbonyl]-1H,3H-pyrrolo[1,2-c]thiazole;

3-(1-oxide-pyridin-3-yl)-7-(1-N,N-dimethylcarbamoylindol-3-ylcarbonyl)- 1H,3H-pyrrolo[1,2-c]thiazole;

3-(1-oxide-pyridin-3-yl)-7-[1-N,N-dimethylcarbamoyl-6-(4-methoxyphenyl)indol- 3-ylcarbonyl]-1H,3H-pyrrolo[1,2-c]thiazole;

3-(pyridin-3-yl)-7-[1-(2-carbomethoxyethyl)-6-(4-fluorophenyl)indol- 3-ylcarbonyl]-1H,3H-pyrrolo[1,2-c]thiazole;

3-(pyridin-3-yl)-7-(6-chloroindol-3-ylcarbonyl)-1H,3H-pyrrolo[1,2-c]thiazole;

3-(pyridin-3-yl)-7-[1-N,N-dimethylcarbamoyl-6-(3,4,5-trimethoxyphenyl)indol- 3-ylcarbonyl]-1H,3H-pyrrolo[1,2-c]thiazole;

3-(pyridin-3-yl)-7-[1-(2-carboxyethyl)-6-(4-fluorophenyl)indol-3-ylcarbonyl]- 1H,3H-pyrrolo[1,2-c]thiazole;

3-(pyridin-3-yl)-7-[1-(2-sulfamylethyl)-6-(4-fluorophenyl)indol-3-ylcarbonyl]- 1H,3H-pyrrolo[1,2-c]thiazole;

3-(pyridin-3-yl)-7-[1-methanesulfonyl-6-(4-fluorophenyl)indol-3-ylcarbonyl]- 1H,3H-pyrrolo[1,2-c]thiazole;

3-(pyridin-3-yl)-7-(1-N,N-dimethylcarbamoyl-6-phenylindol-3-ylcarbonyl)- 1H,3H-pyrrolo[1,2-c]thiazole Hydrochloride;

3-(pyridin-3-yl)-7-[1-(2-N,N-dimethylcarbamoylmethyl)-6-(4-fluorophenyl)indol- 3-ylcarbonyl]-1H,3H-pyrrolo[1,2-c]thiazole;

3-(1-oxide-pyridin-3-yl)-7-(1-N,N-dimethylcarbamoyl-6-phenylindol-3-ylcarbonyl)- 1H,3H-pyrrolo[1,2-c]thiazole hydrochloride;

3-(pyridin-3-yl)-7-[1-N,N-dimethylsulfamyl-6-(4-fluorophenyl)indol- 3-ylcarbonyl]-1H,3H-pyrrolo[1,2-c]thiazole;

3-(pyridin-3-yl)-7-[1-N,N-dimethylcarbamoyl-6-(3-aminophenyl)indol-3-ylcarbonyl]- 1H,3H-pyrrolo[1,2-c]thiazole;

3-(pyridin-3-yl)-7-[1-(2-tert-butoxycarbonylaminoethyl)-6-(4-fluorophenyl)indol- 3-ylcarbonyl]-1H,3H-pyrrolo[1,2-c]thiazole;

3-(1-oxide-pyridin-3-yl)-7-(1-methyl-6-phenylmethoxyindol-3-ylcarbonyl)- 1H,3H-pyrrolo[1,2-c]thiazole;

3-(pyridin-3-yl)-7-[1-(2-aminoethyl)-6-(4-fluorophenyl)indol-3-ylcarbonyl]- 1H,3H-pyrrolo[1,2-c]thiazole;

3-(1-oxide-pyridin-3-yl)-7-[1-N,N-dimethylsulfamyl-6-(4-fluorophenyl)indol- 3-ylcarbonyl]-1H,3H-pyrrolo[1,2-c]thiazole;

3-(pyridin-3-yl)-7-[1-phenylsulfonyl-6-(4-fluorophenyl)indol-3-ylcarbonyl]- 1H,3H-pyrrolo[1,2-c]thiazole;

3-(pyridin-3-yl)-7-[1-N-(2-hydroxyethyl)carbamoyl-6-(4-fluorophenyl)indol- 3-ylcarbonyl]-1H,3H-pyrrolo[1,2-c]thiazole;

3-(pyridin-3-yl)-7-(6-bromoindol-3-ylcarbonyl)-1H,3H-pyrrolo[1,2-c]thiazole;

3-(pyridin-3-yl)-7-(1-N,N-dimethylcarbamoyl-6-bromoindol-3-ylcarbonyl)- 1H,3H-pyrrolo[1,2-c]thiazole;

3-(pyridin-3-yl)-7-(1-N,N-dimethylcarbamoyl-6-chloroindol-3-ylcarbonyl)- 1H,3H-pyrrolo[1,2-c]thiazole;

3-(1-oxide-Pyridin-3-yl)-7-(1-N,N-dimethylcarbamoyl-6-chloroindol- 3-ylcarbonyl)-1H,3H-pyrrolo[1,2-c]thiazole;

3-(1-amino-pyridin-3-yl)-7-[1-N,N-dimethylcarbamoyl-6-(4-fluorophenyl)indol- 3-ylcarbonyl]-1H,3H-pyrrolo[1,2-c]thiazole;

3-(pyridin-3-yl)-7-[1-(2-methanesulfonylaminoethyl)-6-(4-fluorophenyl)indol- 3-ylcarbonyl]-1H,3H-pyrrolo[1,2-c]thiazole;

3-(pyridin-3-yl)-7-[1-hydrazinocarbonyl-6-(4-fluorophenyl)indol-3-ylcarbonyl]- 1H,3H-pyrrolo[1,2-c]thiazole;

3-(pyridin-3-yl)-7-[1-(2-aminoethyl)-6-(4-fluorophenyl)indol-3-ylcarbonyl]- 1H,3H-pyrrolo[1,2-c]thiazole Hydrochloride;

3-(pyridin-3-yl)-7-[1-ethanesulfonyl-6-(4-fluorophenyl)indol-3-ylcarbonyl]- 1H,3H-pyrrolo[1,2-c]thiazole;

3-(pyridin-3-yl)-7-[1-(2-hydroxyethyl)-6-(4-fluorophenyl)indol-3-ylcarbonyl]- 1H,3H-pyrrolo[1,2-c]thiazole;

3-(1-oxide-pyridin-3-yl)-7-[1-phenylsulfonyl-6-(4-fluorophenyl)indol- 3-ylcarbonyl]-1H,3H-pyrrolo[1,2-c]thiazole;

3-(pyridin-3-yl)-7-(1-N,N-dimethylcarbamoyl-6-pyrimid-2-ylindol- 3-ylcarbonyl)-1H,3H-pyrrolo[1,2-c]thiazole;

3-(1-oxide-pyridin-3-yl)-7-[1-(2-N,N-dimethylcarbamoylmethyl)- 6(4-fluorophenyl)indol-3-ylcarbonyl]-1H, 3H-pyrrolo[1,2-c]thiazole;

3-(pyridin-3-yl)-7-[1-carbamoyl-6-(4-fluorophenyl)indol-3-ylcarbonyl]- 1H,3H-pyrrolo[1,2-c]thiazole;

3-(1-carbamoylamino-pyridin-3-yl)-7-[1-N,N-dimethylcarbamoyl- 6-(4-fluorophenyl)indol-3-ylcarbonyl]-1H, 3H-pyrrolo[1,2-c]thiazole;

3-(1-pyrid-3-oylamino-pyridin-3-yl)-7-[1-N,N-dimethylcarbamoyl- 6-(4-fluorophenyl)indol-3-ylcarbonyl]-1H, 3H-pyrrolo[1,2-c]thiazole;

3-(1-oxide-pyridin-3-yl)-7-[1-(2-aminosulfonylethyl)-6- (4-fluorophenyl)indol- 3-ylcarbonyl]-1H,3H-pyrrolo[1,2-c]thiazole;

3-(pyridin-3-yl)-7-[1-N,N-dimethylcarbamoyl-6-(3-aminosulfonylphenyl)indol- 3-ylcarbonyl]-1H,3H-pyrrolo[1,2-c]thiazole;

3-(pyridin-3-yl)-7-[1-(2-N-methylcarbamoylmethyl)-6- (4-fluorophenyl)indol- 3-ylcarbonyl]-1H,3H-pyrrolo[1,2-c]thiazole;

3-(pyridin-3-yl)-7-(1-N,N-dimethylcarbamoyl-6-(4-fluorophenyl)indol- 3-ylcarbonyloxime]-1H,3H-pyrrolo[1, 2-c]thiazole;

3-(pyridin-3-yl)-7-[6-(4-fluorophenyl)indol-3-ylcarbonyloxime]- 1H,3H-pyrrolo[1,2-c]thiazole;

3-(pyridin-3-yl)-7-[1-(N-methyl-N-(dimethylaminoethyl))carbamoyl- 6-(4-fluorophenyl)indol-3-ylcarbonyl]- 1H,3H-pyrrolo[1,2-c]thiazole;

3-(pyridin-3-yl)-7-[1-N-carboxymethylcarbamoyl-6-(4-fluorophenyl)indol- 3-ylcarbonyl]-1H,3H-pyrrolo[1,2-c]thiazole;

3-(1-methyl-pyridin-3-yl)-7-[1-N,N-dimethylcarbamoyl-6-(4-fluorophenyl)indol- 3-ylcarbonyl]-1H,3H-pyrrolo[1,2-c]thiazole;

3-(pyridin-3-yl)-7-(1-N,N-dimethylcarbamoyl-6-thiazol-2-ylindol-3-yl-carbonyl)- 1H,3H-pyrrolo[1,2-c]thiazole;

3-(pyridin-3-yl)-7-[1-N-sulfoethylcarbamoyl-6-(4-fluorophenyl)indol- 3-ylcarbonyl]-1H,3H-pyrrolo[1,2-c]thiazole;

3-(pyridin-3-yl)-7-[1-N,N-dimethylcarbamoyl-6-(2-aminopyrimid-5-yl)indol- 3-yl)carbonyl-1H,3H-pyrrolo[1,2-c]thiazole;

3-(1-oxide-pyridin-3-yl)-7-[1-(2-aminoethyl)-6-(4-fluorophenyl)indol- 3-ylcarbonyl]-1H,3H-pyrrolo[1,2-c]thiazole;

3-(1-oxide-pyridin-3-yl)-7-[1-N,N-dimethylcarbamoyl-6-(4-hydrazinylcarbonylphenyl)indol-3-ylcarbonyl]- 1H,3H-pyrrolo[1,2-c]thiazole;

3-(1-acetoxymethylpyridin-3-yl)-7-[1-N,N-dimethylcarbamoyl- 6-(4-fluorophenyl)indol-3-ylcarbonyl]-1H, 3H-pyrrolo[1,2-c]thiazole;

3-(pyridin-3-yl)-7-[1-N-methyl-N-hydroxymethylcarbamoyl- 6-(4-fluorophenyl)indol-3-ylcarbonyl]-1H, 3H-pyrrolo[1,2-c]thiazole;

3-(pyridin-3-yl)-7-[1-cyanomethyl-6-(4-fluorophenyl)indol-3-ylcarbonyl]- 1H,3H-pyrrolo[1,2-c]thiazole;

3-(pyridin-3-yl)-7-[1-carbamoylmethyl-6-(4-fluorophenyl)indol-3-ylcarbonyl]- 1H,3H-pyrrolo[1,2-c]thiazole;

3-(pyridin-3-yl)-7-[1-carboxymethyl-6-(4-fluorophenyl)indol-3-ylcarbonyl]- 1H,3H-pyrrolo[1,2-c]thiazole;

3-(pyridin-3yl)-7-[1-(1H-tetrazol-5-ylmethyl)-6-(4-fluorophenyl)indol- 3-ylcarbonyl]-1H,3H-pyrrolo[1,2-c]thiazole;

3-(pyridin-3-yl)-7-[1-N,N-dimethylcarbamoyl-6-[2, 4(1H,3H)-pyrimidinedion- 5-yl)indol-3-yl)carbonyl]- 1H,3H-pyrrolo[1,2-c]thiazole;

3-(pyridin-3-yl)-7-[1-N-sulfoethylcarbamoyl-6-(4-fluorophenyl)indol- 3-ylcarbonyl]-1H,3H-pyrrolo[1,2-c]thiazole;

3-(pyridin-3-yl)-7-[1-N-sulfoethylcarbamoyl-6-(4-fluorophenyl)indol- 3-ylcarbonyl]-1H,3H-pyrrolo[1,2-c]thiazole;

3-(pyridin-3-yl)-7-(1-N,N-dimethylcarbamoyl-6-thiophen-2-ylindol-3-yl-carbonyl)- 1H,3H-pyrrolo[1, 2-c]thiazole;

3-(pyridin-3-yl)-7-[1-N,N-dimethylcarbamoyl-6-(4-hydroxymethyl)phenylindol- 3-ylcarbonyl)-1H,3H-pyrrolo[1,2-c]thiazole;

2-oxide-3-(1-oxide-pyridin-3-yl)-7-[1-N,N-dimethylcarbamoyl-6-(4-fluorophenyl)indole- 3-ylcarbonyl]-1H, 3H-pyrrolo[1,2-c]thiazole;

3-(pyridin-3-yl)-7-[1-N,N-dimethylcarbamoyl-6-(4-fluorophenyl)indol- 3-ylcarbonylhydrazone]-1H,3H-pyrrolo[1,2-c]thiazole;

3-(pyridin-3-yl)-7-[1-N-(2-(4-imidazolyl)ethyl)carbamoyl-6-(4-fluorophenyl)indol- 3-ylcarbonyl]-1H,3H-pyrrolo[1,2-c]thiazole; and 3-(pyridin-3-yl)-7-[1-N,N-dimethylcarbamoyl-6-(4-fluorophenyl)indol- 3-ylcarbonylsemicarbazide]-1H,3H-pyrrolo[1,2-c]thiazole;

or a pharmaceutically acceptable salt of each thereof.

As used throughout this specification and the appended claims, the following terms have the meanings ascribed to them;

The term "alkenyl" as used herein refers to straight or branched chain groups of 2 to 6 carbon atoms containing a carbon-carbon double bond. Representative examples of alkenyl groups include ethenyl, 1-propenyl, 2-propenyl, 1-butenyl, and the like.

The term "alkoxy" as used herein refers to an alkyl group, as defined herein, which is bonded to the parent molecular moiety through an oxygen atoms. Representative examples of alkoxy groups include methoxy, ethoxy, tert-butoxy, and the like.

The term "alkoyl" as used herein refers to formyl and radicals of the structure -C(O)-alkyl in which the alkyl portion is a straight or branched alkyl group of from one to six carbon atoms. Representative examples of alkyl groups include formyl, acetyl, propionyl, butyryl, isobutyryl, pivaloyl, and the like.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "alkylsulfonyl" is used herein to mean -SO$_2$(alkyl) where the alkyl group is as defined above. Representative examples of alkylsulfonyl groups include methylsulfonyl, ethylsulfonyl, isopropylsulfonyl, and the like.

The term "benzyl" as used herein refers specifically to a phenyl substituted methyl in which the phenyl group may be substituted with 1, 2, or 3 substituents independently selected from halo, nitro, cyano, alkyl of from one to six carbon atoms, alkoxy, and halo-substituted alkyl and the like.

The term "carboalkoxy" as used herein refers to a structure of formula -C(O)OR wherein R is a straight or branched alkyl radical of from one to six carbon atoms, benyzl, or substituted benzyl, Representative examples of carboalkoxy groups include carbomethoxy, carboethoxy, carbo(iso-propoxy), carbobutoxy, carbo(sec-butoxy), carbo(iso-butoxy), carbo(tert-butoxy), benzyloxycarbonyl, and the like.

The term "nitrogen heterocycle" as used herein refers to any 5- or 6-membered saturated ring containing from one to three heteroatoms independently selected from the group consisting of one, two, or three nitrogens, one oxygen and one nitrogen, and one sulfur and one nitrogen; wherein the nitrogen and sulfur heteroatoms may be optionally oxidized, wherein the nitrogen heteroatoms may be optionally quaternized, and wherein one or more carbon or nitrogen atoms may be substituted with alkyl of from one to six carbon atoms. Representative nitrogen heterocycles include, but are not limited to, pyrrolidinyl, piperidinyl, morpholinyl, piperazinyl, thiomorpholinyl, and the like.

The term "carbamoyl" refers to a structure of formula -CONR'R" wherein R' and R" are independently selected from hydrogen, a straight or branched alkyl radical of from one to six carbon atoms, or taken together may form a nitrogen heterocycle, as previously defined. Representative examples of carbamoyl groups, include -C(O)NH$_2$, N,N-dimethylcarbamoyl, N-tert-butylcarbamoyl, N-methyl-N-ethylcarbamoyl, (morpholin-4-yl)carbonyl, (piperidin-1-yl)carbonyl, (4-methylpiperazin-1-yl)carbonyl and the like.

The term "phenylalkoxy" is used herein to mean a phenyl group appended to an alkoxy radical as previously defined. Representative examples of phenylalkoxy groups include phenylmethoxy (i.e. benzyloxy), 1-phenylethoxy, 2-phenylethoxy, 2-phenylpropoxy, and the like.

The term "phenylalkoyl" is used herein to mean a phenyl group appended through an alkyl or alkenyl group of from one to six carbon atoms or a valence bond to a formyl radical of the structure -C(O)- in which the phenyl group may optionally be substituted with alkyl of from one to six carbon atoms, halogen, or alkoxy a previously defined. Representative examples of phenylalkoyl groups include benzoyl, phenylacetyl, cinnamoyl, phenylpropionyl, and the like.

The terms "PAF-related disorders" and "PAF-mediated disorders" are used herein to mean disorders related to PAF or mediated by PAF, including asthma, shock, respiratory distress syndromes, acute inflammation, gastric ulceration, transplant organ rejection, psoriasis, allergic, kin disease, ischemia and reperfusion injury, delayed cellular immunity, parturtition, fetal lung maturation, and cellular differentiation.

The term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts, and the like. (See, for example S. M. Berge, et al., "Pharmaceutical Salts," *J. Pharm. Sci.* 66: 1–19 (1977) which is incorporated herein by reference.)

Individual enantiomeric forms of compounds of the present invention can be separated from mixtures thereof by techniques well known in the art. For example, a mixture of diastereomeric salts may be formed by reacting the compounds of the present invention with a optically pure form of an acid, followed by purification of the mixture of diastereomers by recrystallization or chromatography and subsequent recovery of the resolved compound from the salt by basification. Alternatively, the enantiomers of the compounds of the present invention can be separated from one another by chromatographic techniques employing separation on a chiral chromatographic medium.

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitioneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents n the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl, alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

Compounds of the present invention can also be administered in the form of liposomers. As is known in the art, liposomers are generally derived from phospholipids or other lipid substances. Liposomers are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, ed., *Methods in Cell Biology*, Volume XIV, Academic Press, New York, N.Y. (1976), p. 33 et seq.

Dosage forms for topical administration of a compound of this invention include powders, sprays, ointments, and inhalants. The active compound is mixed under sterile conditions with a pharmaceutically acceptable carrier and any needed preservatives, buffers, or propellants which may be required. Opthalmic formulations eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the conditions being treated, and the condition and prior medical history of the patient being treated. However, it is within the skill of the art start doses of the compound at levels lower than required to achieve the desired therapeutic effect and to gradually increase the dosage until the desired effect is achieved.

Generally dosage levels of about 0.001 to about 100 mg, more preferably of about 0.01 to about 20 mg, and most preferably about 0.1 to about 10 mg of active compound per kilogram of body weight per day are administered orally to a mammalian patient. If desired, the effective daily dose may be divided into multiple doses for purposes of administration, e.g. two to four separate doses per day.

In general, the compounds of the present invention are synthesized by reaction Schemes 1 through 15 as illustrated below. It should be understood that X, A, $R^1$, $R^2$, $R^3$, $R^5$, $R^6$, $R^7$, $R^8$, $R^9$, $R^{10}$, $R^{11}$, and $R^{12}$ as used herein correspond to the groups identified by Formula I.

The compounds of Formula I may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgement as to the order of synthetic steps, protecting groups required, and deprotection conditions.

Scheme 1

According to the foregoing reaction Scheme 1, L-Cysteine, L-Serine, L-Penicillamine, or a related amino acid (1) is condensed with nicotinaldehyde to produce the thiazolidine or oxazolidine acids 2. The secondary nitrogen atom is then formulated by the action of formic acid/acetic anhydride to yield the N-formyl heterocycles 3.

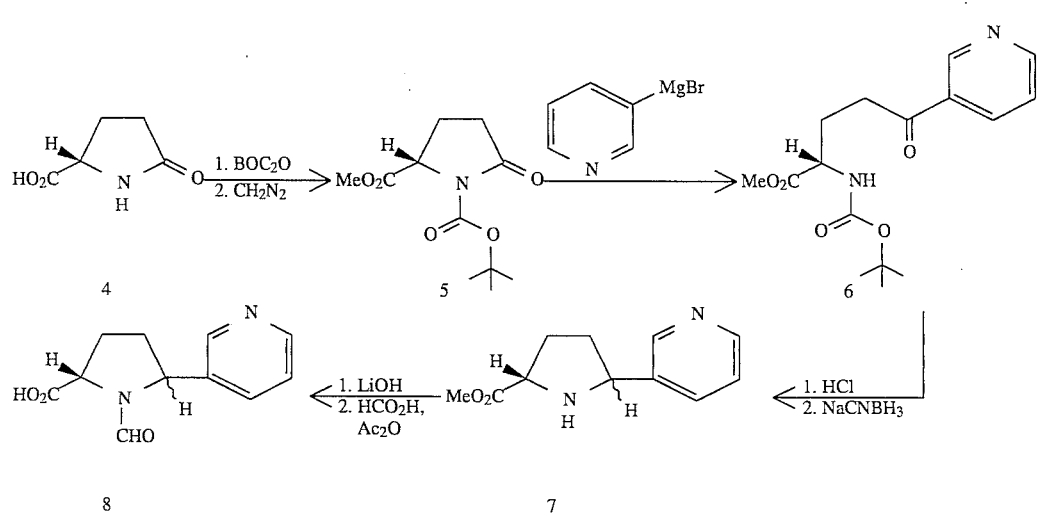

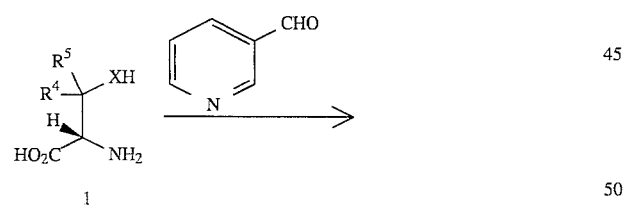

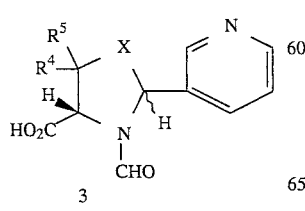

Scheme 2

According to the foregoing reaction Scheme 2, the nitrogen atom of L-pyroglutamic acid may be protected with an appropriate group, preferably tert-butyloxycarbonyl (BOC) with di-tert-butyl dicarbonate followed by methyl ester formation which gives lactam 5. Addition of 3-pyridylmagnesium bromide cleaves the heterocyclic ring and gives ketone 6. The nitrogen atom is deprotected under acidic conditions and reductive cyclization is achieved upon treatment with sodium cyanoborohydride. Hydrolysis of the methyl ester followed by formulation with formic acid/acetic anhydride gives the N-formyl pyrrolidine 8.

Scheme 3

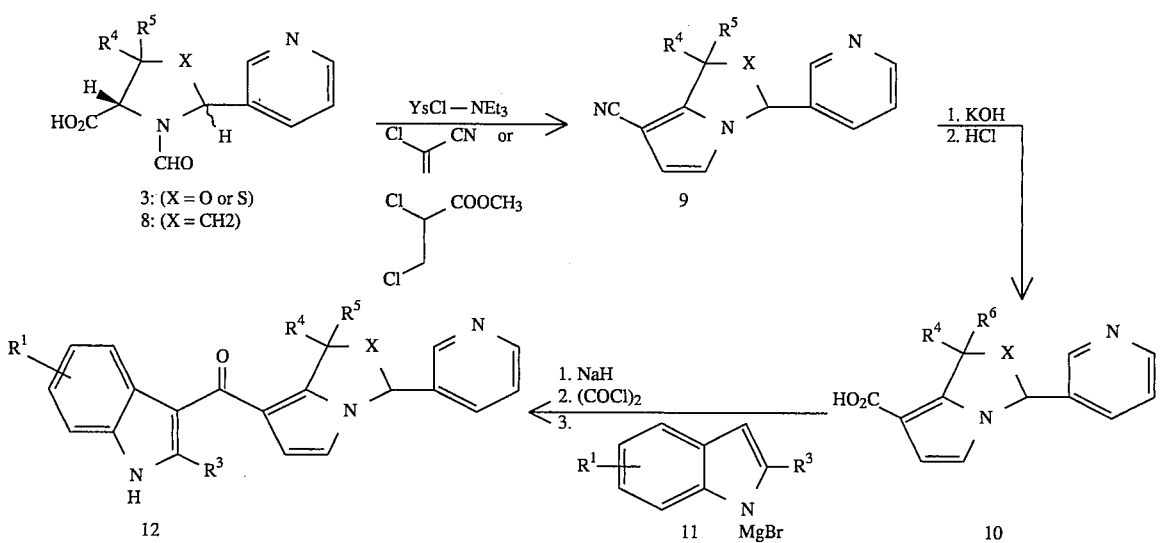

Scheme 3

According to the foregoing reaction Scheme 3, N-formyl heterocycles 3 and 8 may be heated independently with 2-chloroacylonitrile in the presence of triethylamine and p-toluenesulfonyl chloride to afford the corresponding fused bicyclic heterocycle 9. Base catalyzed hydrolysis of the nitrile group followed by acidification affords acid 10. The indole group is introduced by treatment of the anhydrous acid chlorides (prepared from 10 by treatment with sodium hydride followed by oxyalyl chloride) with indole Grignard 11 derived from the reaction of the appropriate substituted indole and ethylmagnesium bromide.

Scheme 4

According to the foregoing reaction Scheme 4, the appropriately substituted indole group is also introduced by treatment of magnesium indole salt with zinc chloride in ether followed by reaction with the anhydrous acid chloride of 10.

Scheme 4

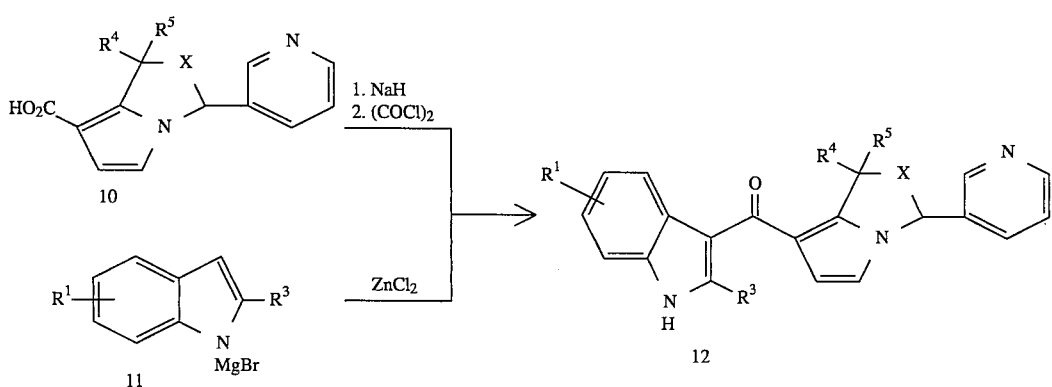

Scheme 5

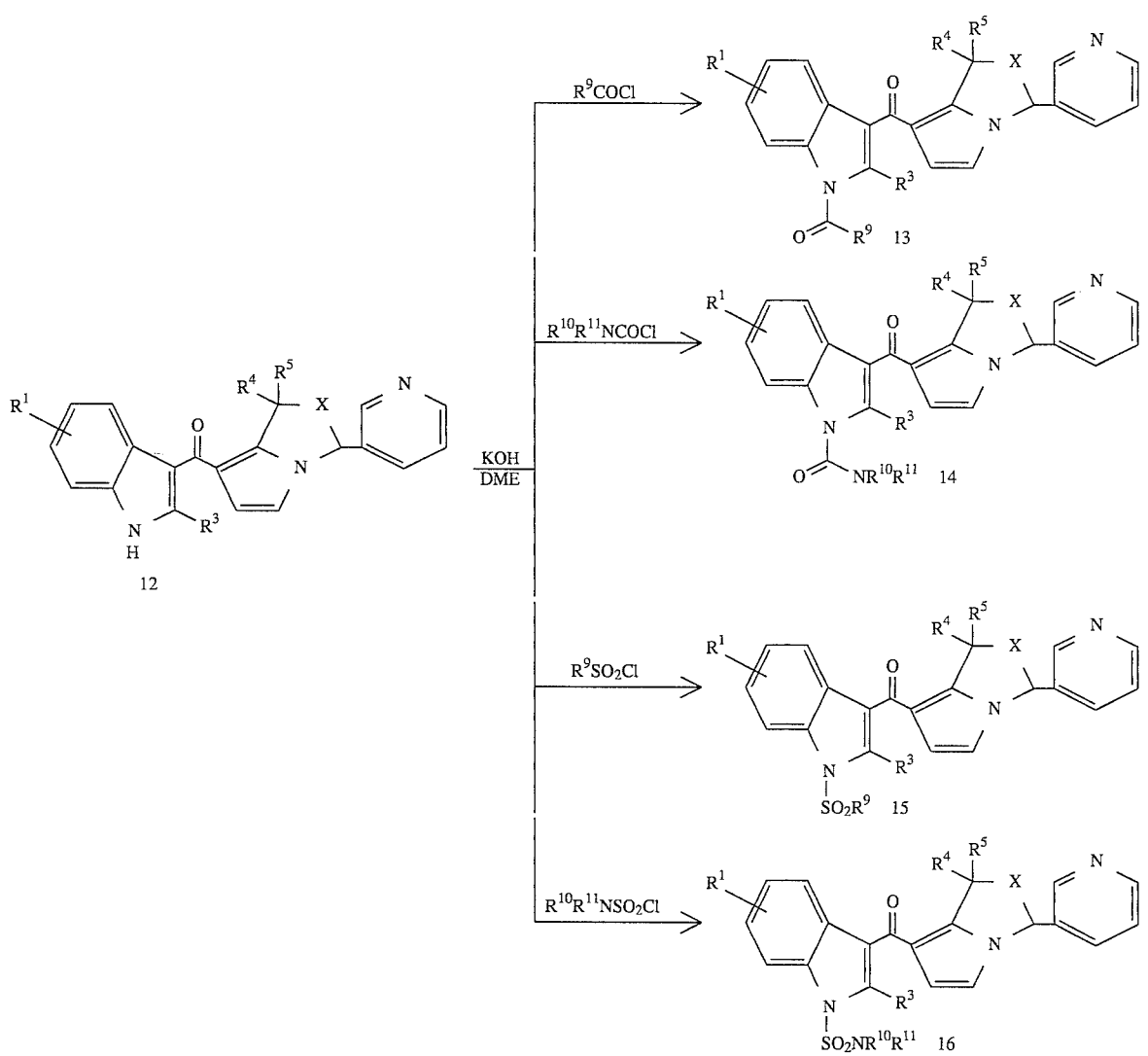

Scheme 5

According to the foregoing reaction Scheme 5, the indole nitrogen atom of the bicyclic heterocycle 12 may be functionalized with an amide group by reaction with the corresponding acid chloride, preferably using potassium hydroxide in 1,2-dimethyloxyethane, giving N-acyl indoles 13. Alternatively, compound 12 may be treated independently with the appropriate carbamoyl chloride under similar conditions to give urea 14. Treatment of a potassium hydroxide solution of 12 in 1,2-dimethoxyethane with the appropriate sulfonyl chloride gives the corresponding sulfonamide 15. Finally, 12 in a potassium hydroxide solution with the appropriate sulfamoyl chloride gives the sulfonylurea 16.

Scheme 6

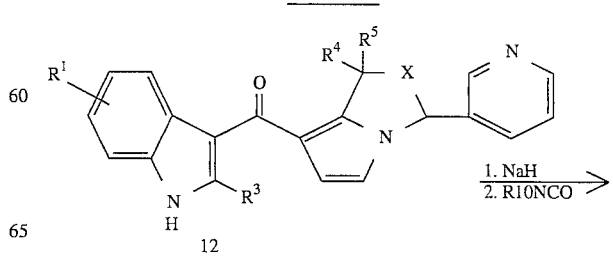

-continued
Scheme 6

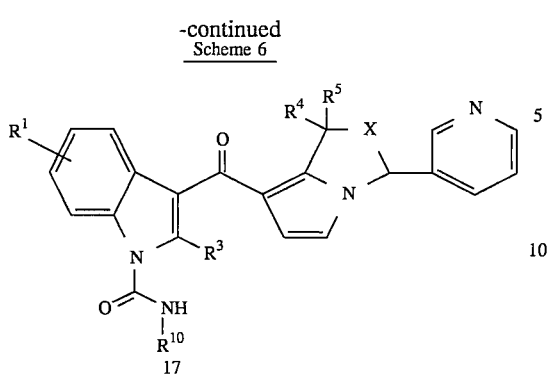

Scheme 6

According to the foregoing reaction Scheme 6, 3-acyl indole heterocycle 12 are treated with the approximate isocyanate to give the urea substituted indole 17.

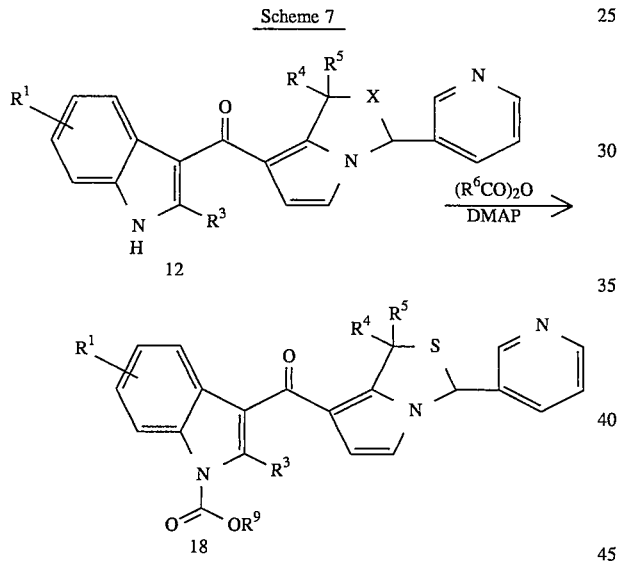

Scheme 7

According to the foregoing reaction Scheme 7, 3-acyl indole heterocycle 12 is treated with the appropriate alkyl dicarbonate in the presence of 4-dimethylaminopyridine to give the corresponding N-carboalkoxy indole 18.

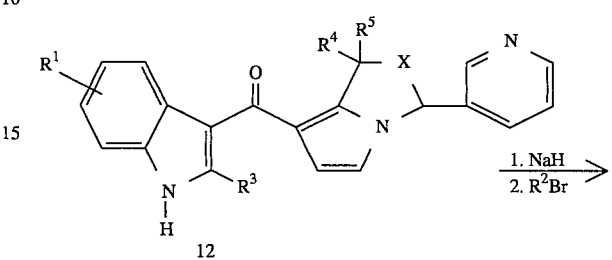

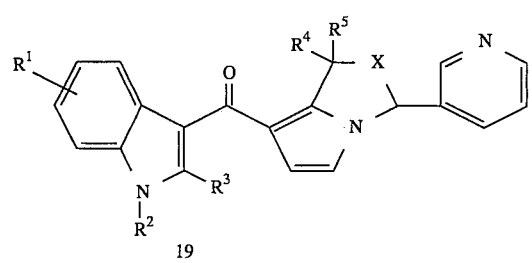

Scheme 8

According to the foregoing reaction Scheme 8, 3-acyl indole heterocycle 12 is treated with sodium hydride followed by the addition of the appropriate alkyl halide to give the corresponding N-alkyl indole 19.

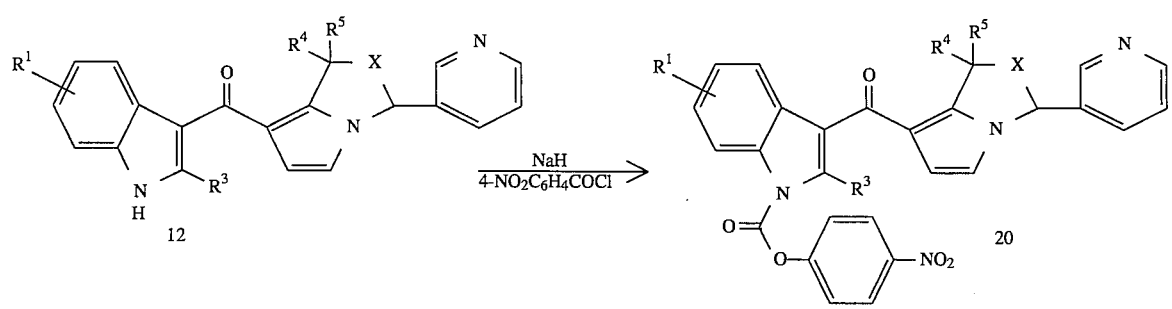

-continued
Scheme 9
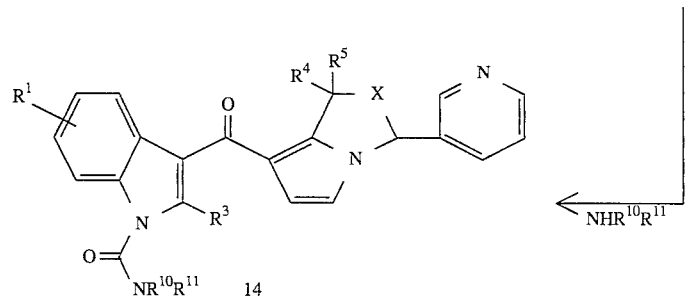
14
Scheme 9
According to the foregoing reaction Scheme 9, 3-acyl indole heterocycle 12 is treated with 4-nitrophenylchloroformate to give the activated acylindole derivative 20 that is subsequently reacted with an appropriately substituted amine to afford urea 14.
Scheme 10
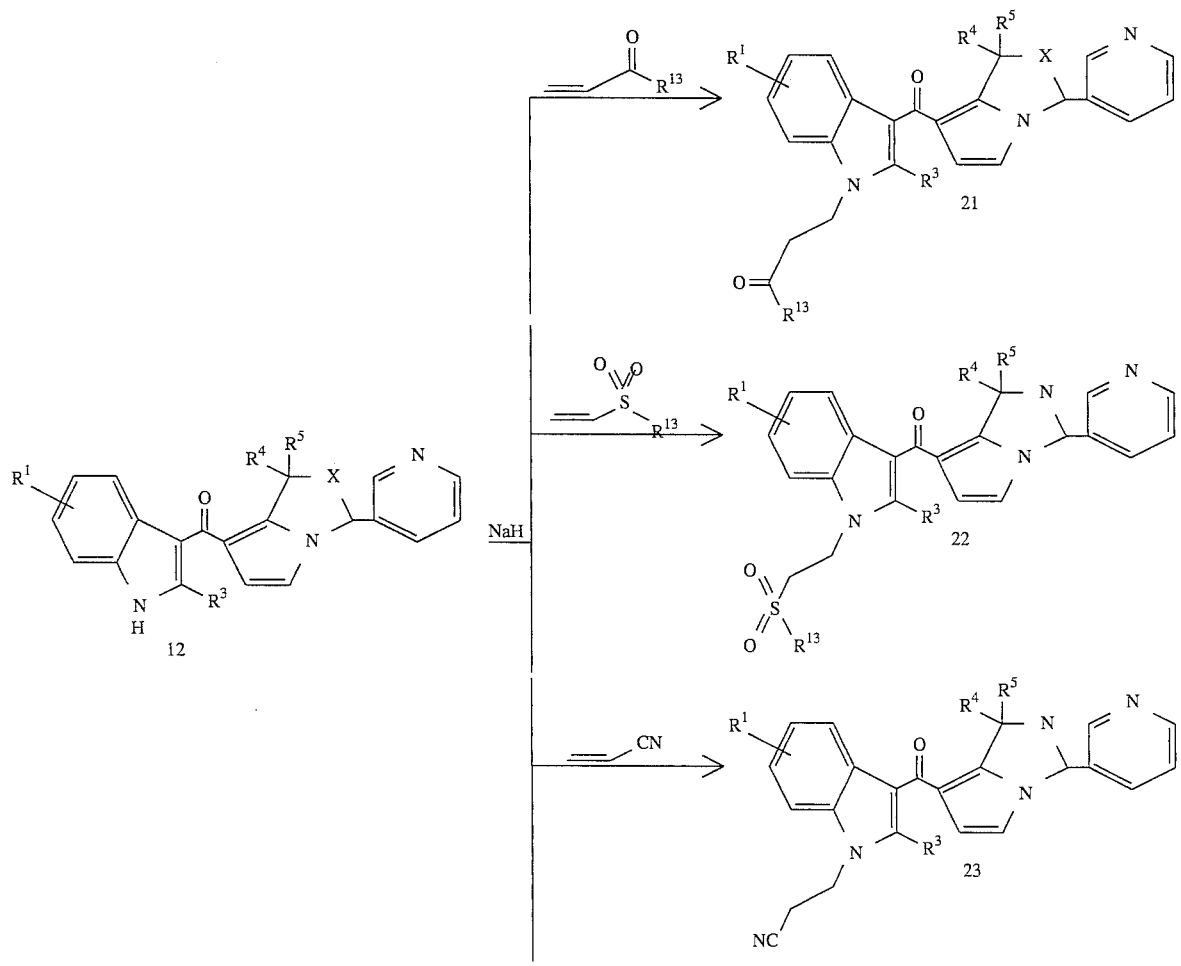

-continued
Scheme 10

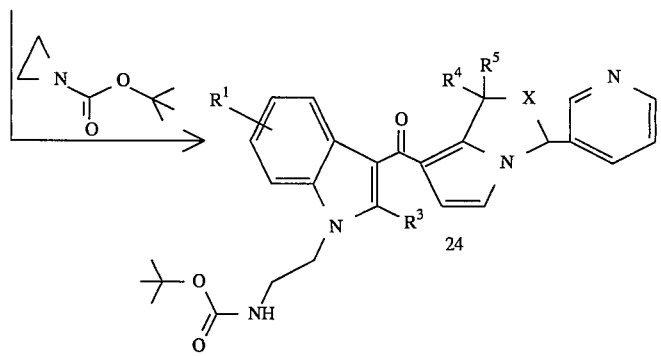

Scheme 10

According to the foregoing reaction Scheme 10, 3-acyl indole heterocycle 12 is treated with sodium hydride and then reacted with an α,β unsaturated carbonyl compound to give 21, with an α,β unsaturated sulfonyl compound to give 22, with an α,β unsaturated nitrile to give 23, or with an acyl aziridine to afford 24. $R^{13}$ in 21 and 22 is used herein to indicate $R^9$, $OR^9$, or $NR^{10}R^{11}$.

Scheme 11

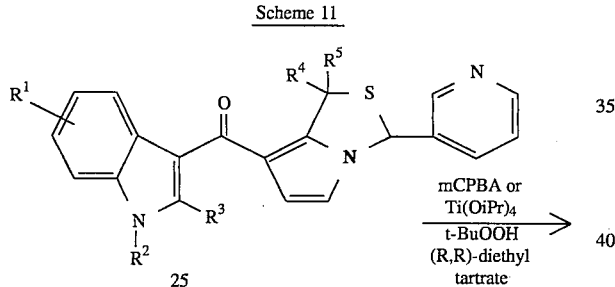

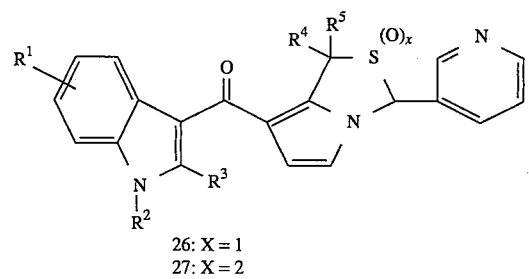

26: X = 1
27: X = 2

Scheme 11

According to the foregoing reaction Scheme 11, the 3-acyl indole heterocycle 25 is treated with tert-butyl hydroperoxide, titanium tetraisopropoxide, and (R,R)-diethyl tartrate, or with m-chloroperoxybenzoic acid to give the corresponding sulfoxide 26 or sulfone 27.

Scheme 12

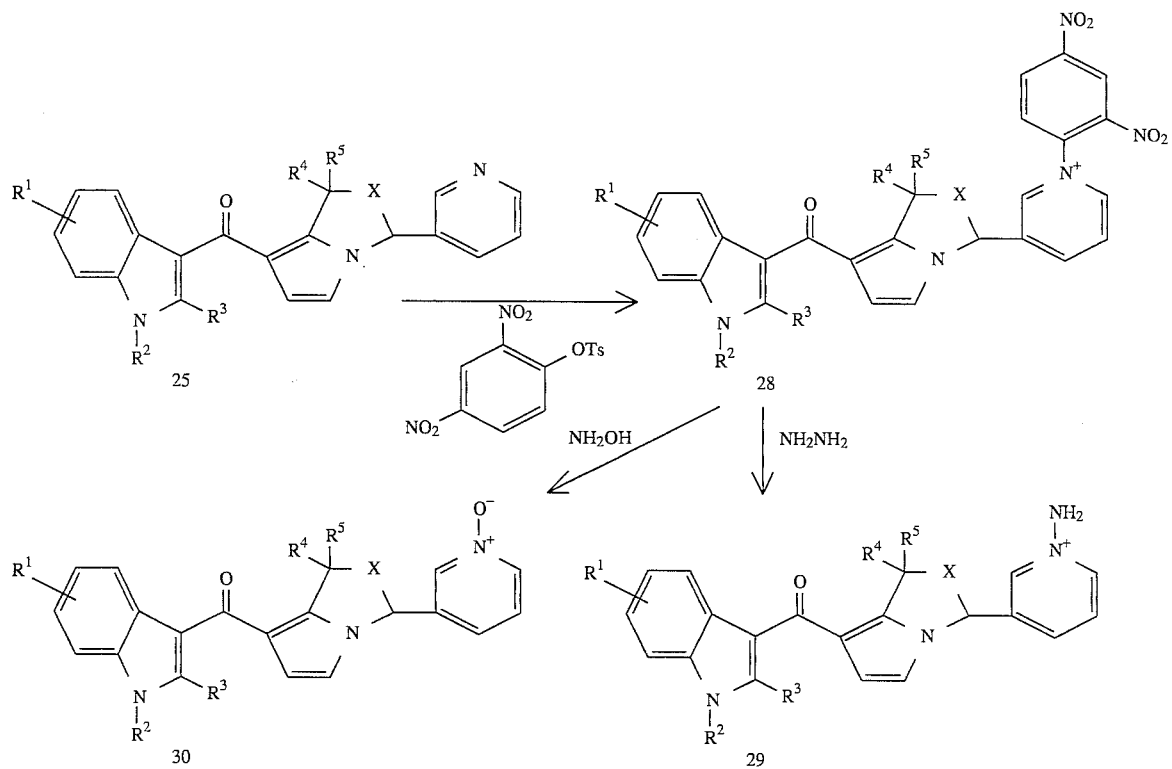

Scheme 12

According to the foregoing reaction Scheme 12, the 3-acyl indole heterocycle 25 is treated with 2,4-dinitrophenyl 4-toluenesulfonate to the pyridinium salt 28. The salt is treated with hydroxylamine to give N-oxide 30 or alternatively with hydrazine to give 29.

Scheme 13

According to the foregoing reaction Scheme 13, the 3-acyl indole heterocycle 25 is treated with an alkyl halide to give pyridinium salt 30. $R^{14}$ is used herein to indicate $R^{12}$ or $CR^7R^8OCOR^8$.

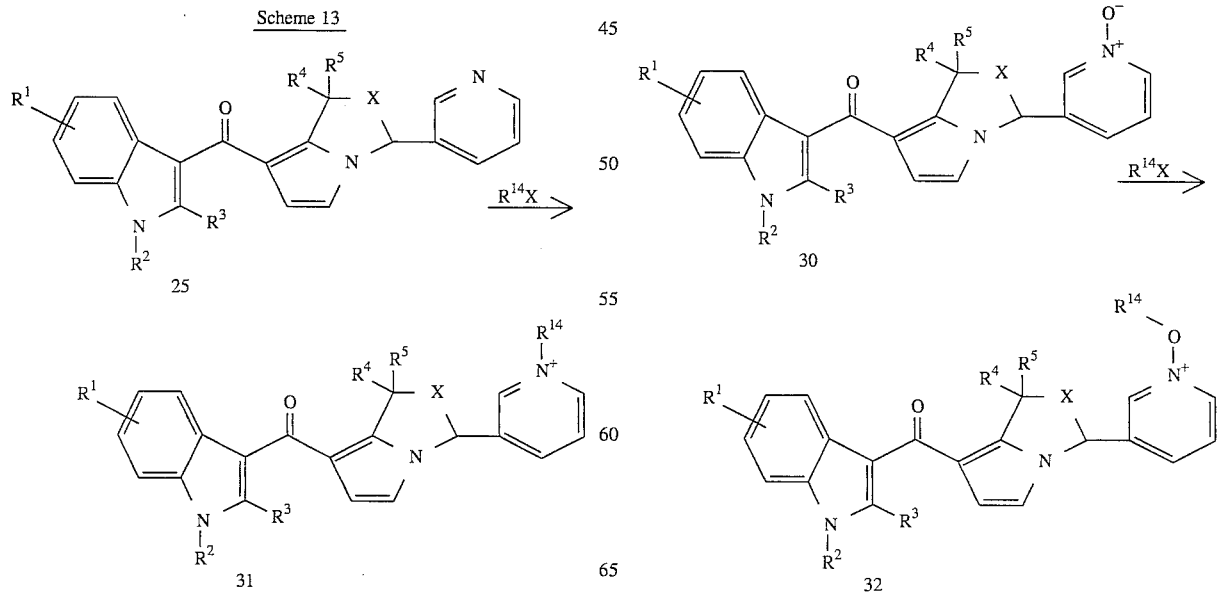

Scheme 14

According to the foregoing reaction Scheme 14, the 3-acyl indole N-oxide heterocycle 30 is treated with an alkyl halide to give pyridinium salt 32.

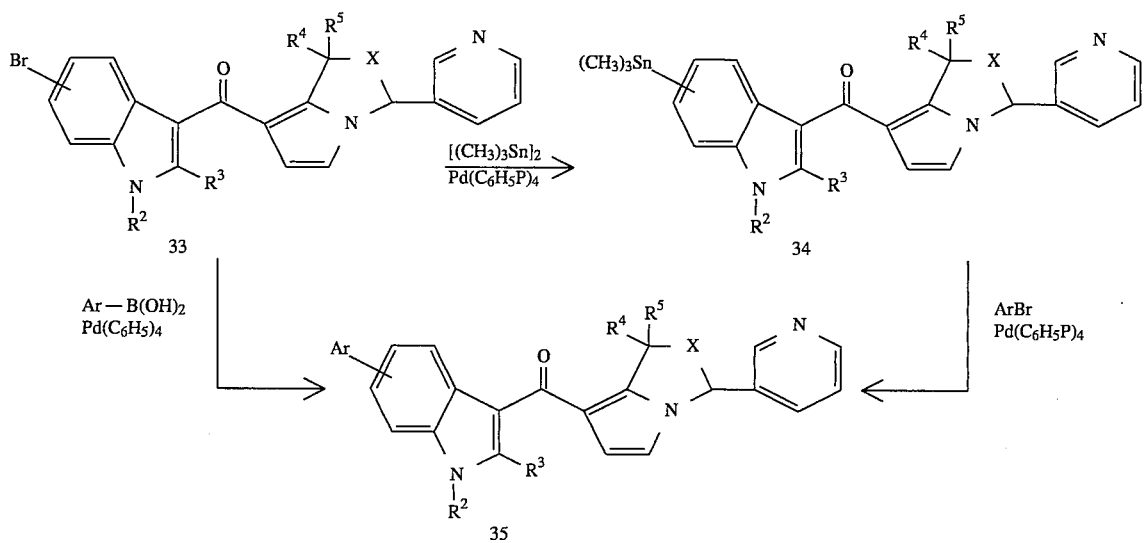

Scheme 15

Scheme 15

According to the foregoing reaction Scheme 15, the bromo indole heterocycle 33 (prepare as described in reaction Scheme 4) is treated with hexamethyltin in the presence of tetrakis(triphenylphosphine)palladium to give 34. This tin reagent is then treated with an aryl halide also in the presence of tetrakis(triphenylphosphine)palladium to afford the aryl indole 35. Alternatively 33 may be converted to 35 directly using the appropriate arylboronic acid in the presence of tetrakis(triphenylphoshine)palladium. Ar is used herein to indicate substituted or unsubstituted phenyl, thiazolyl, pyridyl, pyrimidyl, and the like.

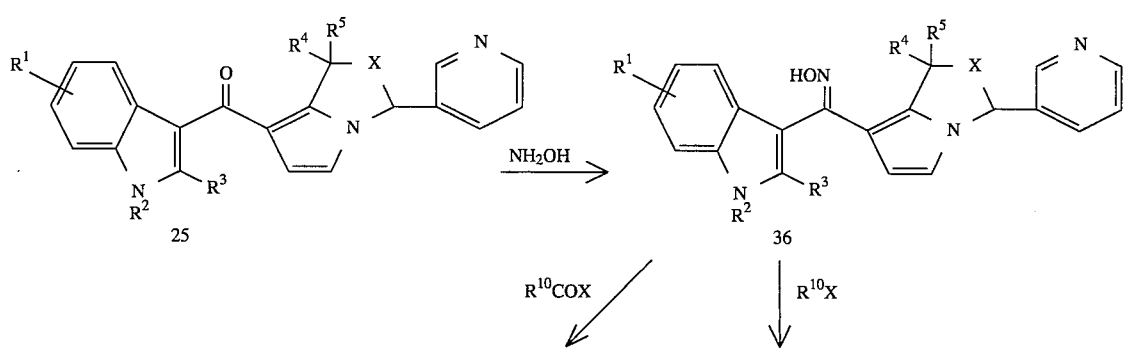

Scheme 16

-continued
Scheme 16

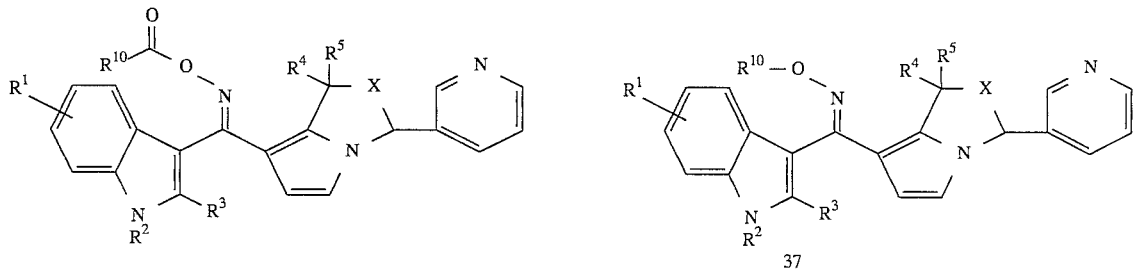

Scheme 16

According to the foregoing reaction Scheme 16, the indole heterocycle 25 is treated with hydroxylamine to give oxime 36. This oxime can be alkylated with an appropriate alkyl halide to give 37, or acylated with an activated acyl compound to give 38.

PAF Inhibitory Activity of the Compounds of the Present Invention

The ability of representative compounds of the present invention to inhibit PAF activity was determined in an in vitro test using the following method.

Citrated whole rabbit blood was obtained from Pel-Freez (Rogers, AR). Rabbit platelets where prepared by centrifugation and washing. The platelets where lysed by freeze-thawing and sonication; platelet membranes where prepared by centrifugation and washing. Final membrane preparations where stored frozen in 10 mM Tris/5 mM $MgCl_2$/2 mM EDTA (TME buffer, pH 7.0) with 0.25 M sucrose added for membrane stabilization.

The standard PAF receptor binding assay contained 10 μg platelet membrane protein, 0.6 nM $[^3H]C_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 μl. The assay was conducted in Millititre-GV™ (Millipore Corp.) filtration plates; incubation time was for 60 minutes at room temperature (22°–23° C.). "Specific binding" was operationally defined as the arithmetic difference between "total binding" of 0.6 nM $[^3H]C_{18}$-PAF (in the absence of added PAF) and "nonspecific binding" (in the presence of 1 μM PAF). After the prescribed incubation, platelet membranes where filtered under vacuum and washed with 1 millilitre of "binding buffer". The filters was dried and removed. The bound radioactivity was quantitated with a Berthold TLC-Linear Analyzer model LB2842.

Dose-response curves of inhibition of specific $[^3H]C_{18}$-PAF binding by test compounds where conducted in triplicate, with at least four doses covering the active range. Experiments where repeated at least once. $IC_{50}$ values (concentration producing 50% inhibition) where determined by point-to-point evaluation. $K_i$ values of inhibitory binding constants where calculated according to the method of Cheng and Prusoff [*Biochem. Pharmacol.* 22 (1973) 3099–3108] whereby $$K_i = \frac{IC_{50}}{1 + ([[^3H]PAF]/K_d[^3H]PAF)}$$
$$= \frac{IC_{50}}{1 + (0.6\ nM/0.6\ mM)}$$
$$= \frac{IC_{50}}{2}$$

The values of $K_i$ for representative compounds of the present invention appear in Table 1.

TABLE 1

| PAF Receptor Binding Activity | |
|---|---|
| Example | $K_i$(nM) |
| 1 | 53. |
| 2 | 2,000 |
| 3 | 180. |
| 4 | 64. |
| 5 | 90. |
| 6 | 120. |
| 7 | 17. |
| 8 | 170. |
| 9 | 110. |
| 10 | 95 |
| 11 | 225. |
| 12 | 23. |
| 13 | 2,200. |
| 14 | 2,400. |
| 15 | 5,600. |
| 16 | 85. |
| 17 | 1,200. |
| 18 | 35. |
| 19 | 100. |
| 20 | 180. |
| 21 | 15. |
| 22 | 9. |
| 23 | 95. |
| 24 | 51. |
| 25 | 272 |
| 26 | 55 |
| 27 | 200 |
| 28 | 75 |
| 29 | 7.5 |
| 30 | 135 |
| 31 | 10 |
| 32 | 150 |
| 33 | 2,800 |
| 34 | 14 |
| 35 | 44 |
| 36 | 1,100 |
| 37 | 10 |
| 38 | 1,000 |
| 39 | 3.3 |
| 40 | 26 |
| 41 | 2,000 |

TABLE 1-continued

PAF Receptor Binding Activity

| Example | $K_i$(nM) |
|---|---|
| 42 | 10.5 |
| 43 | 26 |
| 44 | 40 |
| 45 | 4.1 |
| 46 | 10 |
| 47 | 590 |
| 48 | 8 |
| 49 | 160 |
| 50 | 3.3 |
| 51 | 120 |
| 52 | 16 |
| 53 | 0.7 |
| 54 | 17 |
| 55 | 940. |
| 56 | 110 |
| 57 | 38 |
| 58 | 49 |
| 59 | 27 |
| 60 | 210 |
| 61 | 1,100 |
| 62 | 7.4 |
| 63 | 580 |
| 64 | 15.3 |
| 65 | 89 |
| 66 | 38 |
| 67 | 2,000 |
| 68 | 9.6 |
| 69 | 25 |
| 70 | 2.6 |
| 71 | 244 |
| 72 | 5 |
| 73 | 211 |
| 74 | 84 |
| 75 | 7.5 |
| 76 | 6.1 |
| 77 | 100 |
| 78 | 123 |
| 79 | 18. |
| 80 | 45. |
| 81 | 1.12 |
| 82 | 0.3 |
| 83 | 10.7 |
| 84 | 6.9 |
| 85 | 129. |
| 86 | 4,000 |
| 87 | 71 |
| 88 | 680 |
| 89 | 280 |
| 90 | 480 |
| 91 | 20 |
| 92 | 19 |
| 93 | 0.8 |
| 94 | 40 |
| 95 | 10 |
| 96 | 18 |
| 97 | 19 |
| 98 | 240 |
| 99 | 19 |
| 100 | >300 |
| 101 | 0.95 |
| 102 | 16 |
| 103 | 85 |
| 104 | 2.2 |
| 105 | 4.3 |
| 106 | 8.0 |

The foregoing may be better understood from the following Examples, which are presented for the purpose of illustration and not intended to limit the scope of the inventive concept.

EXAMPLE 1

Preparation of
3-(Pyridin-3-yl)-7-(indol-3-yl)carbonyl-1H,3H-pyrrolo[1,2-c]thiazole To a solution of 3-(pyridin-3-yl)-1H,3H-pyrrolo[1,2-c]thiazole-7-carboxylic acid, prepared as described in U.S. Pat. No. 4,529,728, (1.00 g) in anhydrous tetrahydrofuran (THF) (50 mL) under dry nitrogen was added sodium hydride, 60% oil dispersion (0.18 g, 1.1 equivalents) and stirred 1.0 hour at ambient temperature. To the resulting suspension was added a catalytic amount of dimethylformamide (DMF) followed by the dropwise addition of oxalyl chloride (0.43 mL, 1.2 equivalents). After the reaction mixture had stirred 2.0 hours at ambient temperature, the solvent was evaporated in vacuo at 45° C. The residue was suspended in a mixture of methylene chloride and benzene (3:1 v/v, 30 mL).

In a separate flask, a 3.0 M solution of methyl magnesium bromide in either (2.0 mL, 1.5 equivalents) was added dropwise to a solution of indole (0.72 g, 1.5 equivalents) in benzene (30 mL) at room temperature and stirred 0.75 hour. The resulting green indolylmagnesium bromide solution was cannulated into the suspension of acid chloride described above. The reaction mixture was stirred at room temperature for 18 hours and then quenched with water (equal volume) and extracted with ether (2× equal volume). The combined organic phases where dried over magnesium sulfate and concentrated in vacuo at 45° C. to afford crude product which was purified by flash chromatography (15 p.s.i.) on 250 g silica gel eluting with 1:1 THF/hexane. The resulting yellow solid was triturated with methylene chloride, filtered, and dried at 50° in vacuo to afford the title compound as a white powder (112 mg, 8%). m.p. 237°–238° C. $^1$H NMR (DMSO-$d_6$, 300 MHz) δ4.45 (d, J=15Hz, 1H), 4.63 (dd, J=15, 2Hz, 1H), 6.69 (d, J=3Hz, 1H), 6.77 (d, J=1.5Hz, 1H), 6.88 (d, J=3Hz, 1), 7.20 (dquintet, J=7.5Hz, 1H), 7.43 (dd, J=7.5, 5.3Hz, 1H), 7.48 (d, J=8Hz, 1H), 7.65 (dt, J=2, 8.4Hz, 1H), 8.21 (d, J=3Hz, 1H), 8.24–8.28 (m, 1H), 8.53–8.58 (m, 2H), 11.86 (s, 1H). MS (DCI/NH$_3$) m/e 346 (M+H)$^+$.

EXAMPLE 2

Preparation of
3-(Pyridin-3-yl)-7-(1-N,N-dimethylcarbamoylindol-3-yl)carbonyl- 1H,3H-pyrrolo[1,2-c]thiazole 3-(Pyridin-3-yl)-7-(indol-3-yl)carbonyl-1H,3H-pyrrolo[1,2-c]thiazole prepared as described in Example 1, (0.11 g) was dissolved in dimethoxyethane (DME) (20 mL) and powdered potassium hydroxide (0.09 g, 5 equivalents) was added in one portion. After stirring at ambient temperature for 0.5 hour, N,N-dimethylcarbamoyl chloride (0.038 g, 1.1 equivalents) was added (dropwise and the reaction was stirred for 1 hour. The reaction mixture was poured into water (50 mL) and extracted with either (2×50 mL). The combined extracts where dried over magnesium sulfate and concentrated in vacuo at 50° C. to afford crude product as an amber oil. The crude product was dissolved in the minimal amount of toluene (2 mL) and ether was added until cloudy (20 mL). After standing for 18 hours at −20° C., the supernatant was decanted from a yellow precipitate. The desired product was then precipitated from the supernatant with the addition of excess pentane (50 mL). The white flocculent precipitate was dried in vacuo at 50° C. to afford the title compound as a white powder (28 mg, 21%). m.p. 241°–243° C. $^1$H NMR (DMSO-$d_6$, 300 MHz) δ 3.05 (s, 6H), 4.48 (d, J=15Hz, 1H), 4.66 (dd, J=15, 2Hz, 1H), 6.73 (d, J=3Hz, 1H), 6.79 (d, J=1Hz, 1H), 6.89 (d, J= 3Hz, 1H), 7.28–7.47 (m, 3H), 7.60–7.70 (m, 2H), 8.23–8.28 (m, 1H), 8.32 (s, 1H), 8.55–8.59 (m, 2H). MS (DCI/NH$_3$) m/e 417 (M+H)$^+$. IR (KBr) 1600, 1687, 2930, 3440 cm$^{-1}$.

EXAMPLE 3

Preparation of
3-(Pyridin-3-yl)-7-(5-phenylmethoxyindol-3-yl)carbonyl-1H,3H-pyrrolo[1,2-c]thiazole The title compound was prepared by the procedure described in Example 1 except 5-phenylmethoxyindole was used instead of indole. The crude product was purified by flash chromatography (15 p.s.i.) on 250 g silica gel eluting with 3:2 THF/hexane to afford the title compound. m.p. 178°–179° C. $^1$H NMR (DMSO-$d_6$, 300 MHz) δ4.45 (d, 1H, J=15Hz), 4.62 (dd, 1H, J=15, 2Hz), 5.13 (s, 2H), 6.68 (d, 1H, J=3Hz), 6.76 (d, 1H, J=1Hz), 6.87 (d, 1H, J=3Hz), 6.94 (dd, 1H, J=9, 3Hz), 7.29–7.53 (m, 7H), 7.65 (dt, 1H, J=2.4, 8.4Hz), 7.91 (d, 1H, J=2.5Hz), 8.18 (d, 1H, J=3Hz), 8.53–8.58 (m, 2H), 11.77 (d, 1H, J=2.5Hz). Anal calcd for C$_{27}$H$_{21}$N$_3$O$_2$S: C, 71.82; H, 4.69: N, 9.31. Found: C, 71.41; H, 4.78; N, 9.19. MS (DCI/NH$_3$) m/e 452 (M+H)$^+$. IR (KBr) 1422, 1585, 3400 cm$^{-1}$.

EXAMPLE 4

Preparation of
3-(Pyridin-3-yl)-7-(6-phenylmethoxyindol-3-yl)carbonyl-1H,3H-pyrrolo[1,2-c]thiazole The title compound was prepared by the procedure described in Example 1 using 6-phenylmethoxyindole instead of indole. The crude product was purified by flash chromatography (15 p.s.i.) on 250 g silica gel eluting was 3:2 THF/hexane and then recrystallized from THF, a minimum of methanol, and excess ether to afford the title compound. m.p. 229°–231° C. $^1$H NMR (DMSO-$d_6$, 300 MHz) δ4.45 (d, J= 15Hz, 1H), 4.62 (dd, J=15, 2Hz, 1H), 5.15 (s, 2H), 6.67 (d, J=3Hz, 1H), 6.75 (d, J=2Hz, 1H), 6.85 (d, J=3Hz, 1H), 6.91 (dd, J=9, 2.5Hz, 1H), 7.04 (d, J= 2.5Hz, 1H), 7.30–752 (m, 6H), 7.65 (dt, J=8, 2Hz, 1H), 8.09 (s, 1H), 8.13 (d, J= 9Hz, 1H), 8.53–8.58 (m, 2H), 11.68 (m, 1H). Anal calcd for C$_{27}$H$_{21}$N$_3$O$_2$S: C, 71.82; H, 4.69; N, 9.31. Found: C, 71.72; H, 4.78; N, 9.16. MS (CDI/NH$_3$) m/e 452 (M+H)$^+$. IR (KBr) 1520, 1570, 1620, 3200, 3420 cm$^{-1}$.

EXAMPLE 5

Preparation of
3(Pyridin-3-yl)-7-(7-phenylmethoxyindol-3-yl)carbonyl-1H,3H-pyrrolo[1,2-c]thiazole The title compound was prepared by the procedure described in Example 1 using 7-phenylmethoxyindole instead of indole. The crude product was purified by flash chromatography (15 p.s.i.) on 250 g silica gel eluting with 1:1 THF/hexane and then recrystallized from ethyl acetate/ether to afford the title compound. m.p. 184°– 188° C. $^1$H NMR (DMSO-$d_6$, 300 MHz) δ4.45 (d, J=15Hz, 1H), 4.62 (dd, J=15, 2Hz, 1H), 6.68 (d, J=3Hz, 1H), 6.76 (d, J=1Hz, 1H), 6.85 (d, J= 3Hz, 1H), 6.89 (d, J=8Hz, 1H), 7.08 (t, J=8Hz, 1H), 7.31–7.46 (m, 4H), 7.56–7.67 (m, 3H), 7.83 (d, J=8Hz, 1H), 8.03 (d, J=3Hz, 1H), 8.53–8.58 (m, 2H), 12.06 (d, J=3Hz). Anal calcd for C$_{27}$H$_{21}$N$_3$O$_2$S: C, 71.82; H, 4.69; N, 9.31. Found: C, 71.33; H, 4.70; N, 9.16. MS (DCI/NH$_3$) m/e 452 (M+H)$^+$.

EXAMPLE 6

Preparation of
3-(Pyridin-3-yl)-7-(N,N-dimethylcarbamoyl-5-phenylmethoxyindol-3-yl)carbonyl-1H,3H-pyrrolo[1,2-c]thiazole The title compound was prepared by the procedure described in Example 2 using the compound resulting from Example 3, 3-(pyridin-3-yl)-7-(5-phenylmethoxyindol-3-yl)carbonyl-1H,3H-pyrrolo[1,2-c]thiazole, instead of 3-(pyridin- 3-yl)-7-(indol-3-yl)carbonyl-1H,3H-pyrrolo[1, 2-c]thiazole. The product was recrystallized from ethyl acetate/pentane to give the title compound. m.p. 87°–91° C. $^1$H NMR (DMSO-$d_6$, 300 MHz) δ3.04 (s, 6H), 4.48 (d, J=15Hz, 1H), 4.65 (dd, J=2, 15Hz, 1H), 5.16 (s, 2H), 6.72 (d, J=3Hz, 1H), 6.79 (d, J=1Hz, 1H), 6.89 (d, J= 3Hz, 1H), 7.06 (dd, J=15, 3Hz, 1H), 7.30–7.56 (m, 7H), 7.66 (dt, H=8, 2Hz, 1H), 7.88 (d, J=3Hz, 1H), 8.28 (s, 1H), 8.55–8.59 (m, 2H). Anal calcd for C$_{30}$H$_{26}$N$_4$O$_3$S: C, 68.95; H, 5.01; N, 10.72. Found: C, 68.44; H, 5.17; N, 10.43. MS (CDI/NH$_3$) m/e 523 (M+H)$^+$.

EXAMPLE 7

Preparation of
3-(Pyridin-3-yl)-7-(1-N,N-dimethylcarbamoyl-6-phenylmethoxyindol-3-yl)carbonyl-1H,3H-pyrrolo[1,2-c]thiazole The title compound was prepared by the procedure by the procedure described in Example 2 using the compound resulting from Example 4, 3-(pyridin-3-yl)-7-(6-phenyl-methoxyindol- 3-yl)carbonyl-1H,3H-pyrrolo[1,2-c]thiazole, instead of 3-(pyridin- 3-yl)-7-(indol-3-yl)carbonyl-1H,3H-pyrrolo[1,2-c]thiazole. The product was recrystallized from toluene/ether/excess pentane to give the title compound. m.p. 85°– 91° C. $^1$H NMR (DMSO-$d_6$, 300 MHz) δ3.01 (s, 6H), 4.47 (d, J=15Hz, 1H), 4.55 (dd, J=15, 2Hz, 1H), 5.17 (s, 2H), 6.71 (d, J=3Hz, 1H), 6.78 (d, J=1Hz, 1H), 6.88 (d, J=3Hz, 1H), 7.30–7.52 (m, 6H), 7.66 (dt, J=8.2Hz, 1H), 8.12 (d, J= 15Hz, 1H), 8.19 (s, 1H), 8.54–8.58 (m, 2H). Anal calcd for C$_{30}$H$_{26}$N$_4$O$_3$S: C, 68.95; H, 5.01; N, 10.72. Found: C, 68.66; H, 5.04; N, 10.55. MS (CDI/NH$_3$) m/e 523 (M+H)$^+$.

EXAMPLE 8

Preparation of
3-(Pyridin-3-yl)-7-(1-N,N-dimethylcarbamoyl-7-phenylmethoxyindol-3-yl)carbonyl-1H,3H-pyrrolo[1,2-c]thiazole The title compound was prepared by the procedure described in Example 2 using the compound resulting from Example 5, 3-(pyridin-3-yl)- 7-(7-phenylmethoxyindol-3-yl)carbonyl-1H,3H-pyrrolo[1,2-c]thiazole, instead of 3-(pyridin-3-yl)-7-(indol-3-yl)carbonyl-1H,3H-pyrrolo[1,2-c]thiazole. The product was recrystallized from methylene chloride/THF/hexane to give the title compound. m.p. 210°–211° C. $^1$H NMR (DMSO-$d_6$, 300 MHz) δ2.70 (d, J=21Hz, 6H), 4.45 (d, J= 15Hz, 1H), 4.54 (dd, J=15, 2Hz, 1H), 5.21 (s, 2H), 6.70 (d, J=3Hz, 1H), 6.78 (d, J=1Hz, 1H), 6.88 (s, 1H), 7.05 (d, J=8Hz, 1H), 7.23 (t, J=8Hz, 1H), 7.33–7.53 (m, 6H), 7.66 (dt, J=8, 2Hz, 1H), 7.89 (d, J=8Hz, 1H), 8.28 (s, 1H), 8.52–8.58 (m, 2H). MS (DCI/NH$_3$) m/e 523 (M+H)$^+$.

EXAMPLE 9

Preparation of
3-(Pyridin-3-yl)-7-(1-tert-butyloxycarbonylindol-3-yl)carbonyl-1H, 3H-pyrrolo[1,2-c]thiazole The compound resulting from Example 1 was reacted with di-t-butyldicarbonate in acetonitrile in the presence of 4-dimethylaminopyridine to give, after recrystallization from ether/pentane at −20° C., the title compound. m.p. 150°–152° C. $^1$H NMR (DMSO-d$_6$, 300 MHz) δ1.66 (s, 9H), 4.48 (d, J=15Hz, 1H), 4.65 (dd, J =15, 2Hz, 1H), 6.75 (d, J=3Hz), 1H), 6.83 (d, J=3Hz, 1H), 7.37–7.48 (m, 3H), 7.69 (dt, J=9, 2Hz, 1H), 8.12 (d, J=9Hz, 1H), 8.26 (s, 1H), 8.56–8.60 (m, 2H). Anal calcd for C$_{25}$H$_{23}$N$_3$O$_3$S: C, 67.40; H, 5.20; N, 9.43. Found: C, 67.26; H, 5.53; N, 9.10. MS (CDI/NH$_3$) m/e 446 (M+H)$^+$. IR(KBr) 1540, 1605, 17335, 2980 cm$^{-1}$.

EXAMPLE 10

Preparation of
3-(Pyridin-3-yl)-7-(6-phenylindol-3-yl)carbonyl-1H, 3H-pyrrolo[1,2-c]thiazole The title compound was prepared by the procedure described in Example 1 using 6-phenylindole instead of indole. The product was recrystallized from THF/methanol/ether and then triturated in methylene chloride to afford the title compound. m.p. 258° C. $^1$H NMR (DMSO-d$_6$, 300 MHz) δ4.48 (d, J=15Hz, 1H), 4.65 (dd, J=15, 2Hz, 1H), 6.71 (d, J=3Hz), 6.90 (d, J=3Hz, 1H), 7.32–7.53 (m, 5H), 7.64–7.73 (m, 4H), 8.27 (d, J=3Hz, 1H), 8.33 (d, J= 9Hz, 1H), 8.54–8.59 (m, 2H), 11.96 (d, J=3Hz, 1H). Anal calcd for C$_{26}$H$_{19}$N$_3$OS: C, 74.09; H, 4.54; N, 9.97. Found: C, 73.93; H, 4.57; N, 9.92. MS (DCI/NH$_3$) m/e 422 (M+H)$^+$. IR(KBr) 1505, 1522, 1550, 1580, 3180, 3420 cm$^{-1}$.

EXAMPLE 11

Preparation of
3-(Pyridin-3-yl)-7-[1-(morpholin-4-ylcarbonyl)indol-3-yl]carbonyl-1H,3H-pyrrolo[1,2-c]thiazole The title compound was prepared by the procedure described in Example 2 using the compound resulting from Example 1, 3-(pyridin-3-yl)-7-indol-3-yl)carbonyl- 1H,3H-pyrrolo[1,2-c]thiazole, and (morpholin-4-yl)chloroformate to give, after recrystallization from ethyl acetate/ether, the title compound, m.p. 161°–163° C. $^1$H NMR (DMSO-d$_6$, 300 MHz) δ3.53–3.58 (m, 4H), 3.66–3.72 (m, 4H), 4.48 (d, J =15Hz, 1H), 4.65 (d, J=15Hz, 1H), 6.75 (d, J=2Hz, 1H), 6.80 (s, 1H), 6.90 (d, J=3Hz, 1H), 7.28–7.47 (m, 3H), 7.68 (d, J=8Hz, 2H), 8.22–8.30 (m, 2H), 8.55–8.59 (m, 2H). MS (DCI/NH$_3$) m/e 459 (M+H)$^+$. IR(CDCl$_3$) 1540, 1605, 1690, 2850, 2920, 2970 cm$^{-1}$.

EXAMPLE 12

Preparation of
3-(Pyridin-3-yl)-7-(1-N,N-dimethylcarbamoyl-6-phenylindol-3-yl)carbonyl-1H,3H-pyrrolo[1,2-c]thiazole The title compound was prepared by the procedure described in Example 2 using the compound resulting from Example 10, 3-(pyridin-3-yl)-7-(6-phenylindol-3-yl)carbonyl- 1H,3H-pyrrolo[1,2-c]thiazole, instead of 3-(pyridin-3-yl)-7-(indol-3-yl)carbonyl- 1H,3H-pyrrolo[1,2-c]thiazole. The crude product was purified by flash chromatography (15 p.s.i.) on 250 g silica gel eluting with ethyl acetate to give the title compound as an amorphous solid. m.p. 115°–125° C. $^1$H NMR (DMSO-d$_6$, 300 MHz) δ3.09 (s, 6H), 4.50 (d, J=15Hz, 1H), 4.68 (dd, J=15, 2Hz, 1H), 6.74 (d, J= 3Hz, 1H), 6.80 (d, J=1Hz, 1H), 6.92 (d, J=3Hz, 1H), 7.34–7.53 (m, 4H), 7.84 (d, J=1Hz, 1H), 8.33 (d, J=9Hz, 1H), 8.38 (s, 1H), 8.57–8.60 (m, 2H). MS (DCI/NH$_3$) m/e 493 (M+H)$^+$. IR(CDCl$_3$) 1540, 1610, 1690, 2930 cm$^{-1}$.

EXAMPLE 13

Preparation of 2-Oxide-3-(pyridin-3-yl)-7-(1-tert-butyloxycarbonylindol-3-ylcarbonyl)-1H,3H-pyrrolo[1,2-c]thiazole To a solution of 3-(pyridin-3-yl)-7-(1-tert-butyloxycarbonylindol-3-yl)carbonyl- 1H,3H-pyrrolo[1,2-c]thiazole (270 mg, 0.61 mmol) prepared as described in example 9, in CHCl3 (50 mL) at −20° C. was added a solution of 3-chloroperbenzoic acid in CHCl3 (50 mL). The reaction mixture was stirred for three hours at −20° C. and then was partitioned between CHCl$_3$ and saturated aqueous NaHCO$_3$. The organic phase was washed with brine, dried over MgSO$_4$, filtered, and concentrated. Purification by flash chromatography on silica gel (ethyl acetate) afforded the desired sulfoxide (150 mg). m.p. 155°–157° C. $^1$H NMR (DMSO-d6, 300 MHz) δ1.67 (s, 9H), 4.27 (d, 1H, J=17 Hz), 4.68 (d, 1H, J=17 Hz), 6.72 (s, 1H), 6.97 (d, 1H, J=3 Hz), 7.12 (d, 1H, J=3 Hz), 7.36–7.50 (m, 4H), 8.11–8.16 (m, 1H), 8.20–8.24 (m, 1H), 8.31 (s, 1H), 8.45 (m, 1H), 8.61 (dd, 1H, J=2, 4 Hz), MS (DCI/NH$_3$) m/e 462 (M+H)$^+$, 479 (M+NH4)$^+$, 414. IR (CDCl3) 2980, 1740, 1620, 1545. Anal calcd for C$_{25}$H$_{23}$N$_3$O$_4$S: C, 65.06; H, 5.02; N, 9.10. Found: C, 63.92; H, 5.16; N, 8.72.

EXAMPLE 14

Preparation of
2-Oxide-3-(pyridin-3-yl)-7-(indol-3-ylcarbonyl)-1H,3H-pyrrolo[1,2-c]thiazole The title compound was prepared by the procedure described in Example 13 using the compound resulting from Example 1, 3-(Pyridin-3-yl)-7-(indol-3-yl)carbonyl- 1H,3H-pyrrolo[1,2-c]thiazole, instead of 3-(pyridin-3-yl)-7-(1-tert-butyloxycarbonylindol- 3-yl)carbonyl-1H,3H-pyrrolo[1,2-c]thiazole, m.p. 158° C. (decomp). $^1$H NMR (DMSO-d6, 300 MHz) δ4.25 (d, 1H, J=18 Hz), 4.67 (d, 1H, J=18 Hz), 6.68 (s, 1H), 7.00 (d, 1H, J=3 Hz), 7.06 (d, 1H, J=3 Hz), 7.16–7.27 (m, 2H), 7.39–7.52 (m, 3H), 8.25–8.29 (m, 2H), 8.42 (d, 1H, J=2 Hz), 8.59–8.62 (m, 1H), 11.92 (s, 1H). MS (DCI/NH$_3$) m/e 362 (M+H)$^+$, 379 (M+NH4)$^+$, 346, 315. IR (KBr) 3420, 2920, 1592, 1422. Anal calcd for C$_{20}$H$_{15}$N$_3$O$_2$S: C, 66.47; H, 4.18; N, 11.63. Found: C, 63.69; H, 4.64; N, 10.39.

EXAMPLE 15

Preparation of
3-(Pyridin-3-yl)-7-(indol-3-ylcarbonyl)-1H,3H-pyrrolo
[1,2-c]oxazole The desired compound was prepared according to the method of Example 1, except substituting 3-(3-pyridin-3-yl)-1H,3H-pyrrolo[1,2-c]oxazole-7-carboxylic acid, prepared from 2-pyridine carboxaldehyde and L-serine as described in U.S. Pat. No. 4,529,728, for 3-(3-pyridin-3-yl)-1H,3H-pyrrolo[1,2-c]thiazole-7-carboxylic acid. $^1$H NMR (DMSO-d6) δ5.28 (dd, 1H, J=1.5, 13.0Hz), 5.44 (dd, 1H, J=2.0, 13.0Hz), 6.80 (d, 1H, J=3.0Hz), 6.84 (s, 1H), 6.90 (d, 1H, J=3.0Hz), 7.19 (pd, 2H, J=1.5, 7.0Hz), 7.47 (d, 1H, J=7.0Hz), 7.49 (m, 1H), 7.825 (m, 2H), 8.68 (dd, 1H, J=2.0, 5.0Hz), 8.71 (d, 1H, J=2.0Hz). MS (DCI/NH$_3$) m/e 330 (M+1)$^+$.

EXAMPLE 16

Preparation of
3-(Pyridin-3-yl)-7-(1-N,N-diisopropylcarbamoyl-6-
phenylmethoxyindol-
3-ylcarbonyl)-1H,3H-pyrrolo[1,2-c]thiazole The title compound was prepared by the procedure described in Example 2 using the compound resulting from Example 4, 3-(pyridin-3-yl)-7-(6-phenylmethoxyindol-3-yl)carbonyl-1H,3H-pyrrolo[1,2-c]thiazole, instead of 3-(pyridin- 3-yl)-7-(indol-3-yl)carbonyl-1H,3H-pyrrolo[1,2-c]thiazole and using diisopropylcarbamoylchloride instead of dimethylcarbamoylchloride. $^1$H NMR (CDCl$_3$, 300 MHz) δ1.30 (d, 12H, J=7 Hz), 3.63 (m, 2H), 4.47 (d, 1H, J=15 Hz), 4.65 (d, 1H, J=15 Hz), 5.18 (s, 2H), 6.72 (d, 1H, J=3 Hz), 6.78 (s, 1H), 6.88 (d, 1H, J=3Hz), 6.97 (s, 1H), 7.04 (d, 1H, J=10 Hz), 7.29–7.50 (m, 6H), 7.62–7.69 (m, 1H), 8.15 (d, 1H, J=9 Hz), 8.19 (s, 1H), 8.53–8.58 (m, 2H). MS (DCI/NH$_3$) m/e 579 (M+H)$^+$, 457. IR (CDCl$_3$) 2970, 1685, 1616. Anal calcd for C$_{34}$H$_{34}$N$_4$O$_3$S: C, 70.56; H, 5.92; N, 9.68. Found: C, 69.08; H, 5.84; N, 9.39.

EXAMPLE 17

Preparation of
1,1-Dimethyl-3-(pyridin-3-yl)-7-(indol-3-ylcarbonyl)-
1H,3H-pyrrolo[ 1,2-c]thiazole Step 1,
2-(3-pyridinyl)-5,5-dimethyl-4-thiazolidinecarboxylic
acid To a suspension of DL-penicillamine (50 g, 335 mmol) in 1:1 aqueous ethanol (500 mL) was added 3-pyridinecarboxaldehyde (36 g, 335 mmol). The resulting clear-yellow solution was stirred for 17 hours at ambient temperature during which time a white precipitate formed. The white solid was filtered off and rinsed with 3:1 H$_2$O, ethanol and ether to give 2-(3-pyridinyl)-5,5-dimethyl-4-thiazolidinecarboxylic acid (51 g, 64%).

Step 2, 2-(3-pyridinyl)-3-formyl-5,5-dimethyl-4-
thiazolidinecarboxylic acid

Formic acid (17 g, 378 mmol) and acetic anhydride (13 g, 126 mmol) where combined at 10° C. A slurry of 2-(3-pyridinyl)-5,5-dimethyl-4-thiazolidinecarboxylic acid (10 g, 42 mmol), Prepared as in step 1, in THF (250 mL) was added over five minutes. The resulting clear-yellow solution was wanted slowly to ambient temperature and stirred for 17 hours, during which time it became a white suspension. The THF was removed in vacuo, and the resulting slurry was filtered to yield a white solid. The solid was rinsed with ether to give 2-(3-pyridinyl)-3-formyl-5,5-dimethyl- 4-thiazolidinecarboxylic acid (10 g) which was used without further purification.

Step 3. methyl
1,1-dimethyl-3-(pyrid-3-yl)-1H,3H-pyrrolo[1,2-c]
thiazole-7-carboxylate To a solution of p-toluenesulfonyl chloride (18 g, 95 mmol) and methyl 2,3-dichloropropionate (15 g, 95 mmol) in refluxing CH$_2$Cl$_2$ (125 mL) was added a mixture of 2-(3-pyridinyl)-3-formyl-5,5-dimethyl-4-thiazolidinecarboxylic acid (5.1 g, 19 mmol) and triethylamine (2.3 g, 22 mmol) in CH$_2$Cl$_2$ (125 mL). After one hour at reflux triethylamine (4.6 g, 44 mmol) was added and the reaction mixture was refluxed for a further 17 hours. The reaction mixture was cooled to ambient temperature and partitioned between cold 1N aqueous NaOH and ethyl acetate. The organic phase was washed with cold 1N aqueous NaOH and brine, dried over MgSO$_4$, filtered, and concentrated in vacuo. The crude product was dissolved in 5% aqueous HCl and the solution was extracted twice with ether. The aqueous phase was neutralized with solid Na$_2$CO$_3$ and extracted twice with ethyl acetate. The combined ethyl acetate extracts where washed with brine, dried over MgSO$_4$, and concentrated in vacuo. Chromatography on silica gel (150 g, 1:1 ethyl acetate, hexanes), afforded methyl 1,1-dimethyl-3-(pyrid-3-yl)-1H,3H-pyrrolo[1,2-c]thiazole-7-carboxylate (1.1 g, 20%) as an off-while powder.

Step 4,
1,1-dimethyl-3-(pyrid-3-yl)-1H,3H-pyrrolo[1,2-c]
thiazole- 7-carboxylic acid A mixture of methyl 1,1-dimethyl-3-(pyrid-3-yl)-1H,3H-pyrrolo[1,2-c]thiazole- 7-carboxylate (1.1 g, 3.8 mmol), 1N aqueous NaOH (19 mmol), and methanol (40 mL) was refluxed for 17 hours. The reaction mixture was cooled to ambient temperature and taken to pH 4 with concentrated HCl. The thick solution was extracted twice with 9:1 CHCl$_3$, isopropanol. The combined organic layers where washed with brine, dried over MgSO$_4$, filtered, and concentrated in vacuo to give a yellow powder. The powder was triturated with ether to afford 1,1-dimethyl-3-(pyrid- 3-yl)-1H,3H-pyrrolo[1,2-c]thiazole-7-carboxylic acid as a pale-yellow powder.

Step 5,
1,1-Dimethyl-3-(pyridin-3-yl)-7-(indol-3-ylcarbonyl)-
1H,3H-pyrrolo[1,2-c] thiazole The desired compound was prepared according to the method of Example 1, except substituting 1,1-dimethyl-3-(pyrid-3-yl)-1H,3H-pyrrolo[1,2-c]thiazole- 7-carboxylic acid (1.0 g, 3.6 mmol) for 3-(pyridin-3-yl)-1H,3H-pyrrolo [1,2-c]thiazole- 7-carboxylic acid to give 1,1-Dimethyl-3-(pyridin-3-yl)-7-(indol-3-ylcarbonyl)-1H,3H-pyrrolo[ 1,2-c]thiazole (183 mg, 14%). m.p. 254°–257° C. $^1$H NMR (CDCl$_3$, 300 MHz) δ2.05 (s, 3H), 2.07 (s, 3H), 6.19 (d, J=3Hz, 1H), 6.50 (s, 1H), 6.70 (d, J=3 Hz, 1H), 7.35 (m, 1H), 7.43 (m, 1H), 7.70 (dt, J=9.0, 1.5 Hz, 1H), 7.82 (d, J=3 Hz, 1H), 8.53 (bs, 1H), 8.64 (dd, J=6.0, 1.5 Hz, 2H), MS (DCI/NH$_3$) m/e 374 (M+1)$^+$, 253, 141, 124.

EXAMPLE 18

Preparation of
3-(Pyridin-3-yl)-7-(1-carbomethoxycarbamoyl-6-phenylmethoxyindol-3-ylcarbonyl)-1H,3H-pyrrolo[1,2-c]thiazole The desired compound was prepared according to the method of Example 2, except substituting 3-(pyridin-3-yl)-7-(6-phenylmethoxyindol-3-yl)carbonyl-1H,3H-pyrrolo[1,2-c]thiazole, prepared as in Example 4 for 3-(pyridin-3-yl)-7-(indol-3-yl)carbonyl- 1H,3H-pyrrolo[1,2-c]thiazole and substituting methyl chloroformate for N,N-dimethylcarbamoyl chloride. m.p. 152°–153° C. $^1$H NMR (DMSO-d6, 300 MHz) δ4.03 (s, 3H), 4.47 (d, 1H, J=15 Hz), 4.63 (dd, 1H, J=2, 15 Hz), 5.20 (s, 2H), 6.73 (d, 1H, J=3H), 6.80 (d, 1H, J=2Hz), 6.81 (d, 1H, J=3 Hz), 7.12 (dd, 1H, J=3, 9 Hz), 7.30–7.52 (m, 6H), 7.67 (dt, 1H, J=8, 2 Hz), 7.79 (d, 1H, J=3 Hz), 8.08 (d, 1H, J=9 Hz), 8.16 (s, 1H), 8.55–8.59 (m, 2H). MS (DCI/NH$_3$) m/e 510 (M+H)$^+$. Anal calcd for C$_{29}$H$_{23}$N$_3$O$_4$S: C, 68.35; H, 4.55; N, 8.25. Found: C, 67.84; H, 4.63; N, 8.04.

EXAMPLE 19

Preparation of
1,1-Dimethyl-3-(pyridin-3-yl)-7-(1-N,N-dimethylcarbamoyl-indol-3-ylcarbonyl)-1H,3H-pyrrolo[1,2-c]thiazole The title compound was prepared by the procedure described in Example 2 using the compound resulting from Example 17, 1,1-dimethyl-3-(pyridin-3-yl)-7-(indol- 3-yl-carbonyl)-1H,3H-pyrrolo[1,2-c]thiazole, instead of 3-(Pyridin-3-yl)-7-(indol- 3-yl)carbonyl-1H,3H-pyrrolo[1,2-c]thiazole. $^1$H NMR (CDCl$_3$, 300 MHz) δ 2.05 (s, 3H), 2.06 (s, 3H), 3.13 (s, 6H), 6.20 (d, 1H, J=3Hz), 6.51 (s, 1H), 6.72 (d, 1H, J=3Hz), 7.36 (m, 3H), 7.58 (m, 1H), 7.69 (dt, 1H, J=7.5, 1.5Hz), 7.91 (s, 1H), 8.34 (m, 1H), 8.64 (b, 2H). MS (DCI/NH$_3$) 445(M+H)$^+$, 322, 124.

EXAMPLE 20

Preparation of
3-(Pyridin-3-yl)-7-(1-N-methyl-N-phenylcarbamoyl-6-phenylmethoxyindol-3-ylcarbonyl)-1H,3H-pyrrolo[1,2-c]thiazole The title compound was prepared by the procedure described in Example 2 using the compound resulting from Example 4, 3-(pyridin-3-yl)-7-(6-phenylmethoxyindol-3-yl)carbonyl-1H,3H-pyrrolo[1,2-c]thiazole, instead of 3-(pyridin- 3-yl)-7-(indol-3-yl)carbonyl-1H,3H-pyrrolo[1,2-c]thiazole and using N-methyl-N-phenylcarbamoylchloride instead of N,N-dimethylcarbamoylchloride. $^1$H NMR (DMSO-d6, 300 MHz) δ3.49 (s, 3H), 4.34 (d, 1H, J=15Hz), 4.52 (dd, 1H, J=15, 2Hz), 5.18 (s, 2H), 5.72 (d, 1H J=3Hz), 6.55 (d, 1H), 6.72 (d, 1H, J=3Hz), 7.00 (dd, 1H, J=9, 3Hz), 7.18–7.55 (m, 12H), 7.60–7.66 (m, 2H), 7.98 (d, 1H, J=8Hz), 8.52 (d, 1H, J=2Hz), 8.58 (dd, 1H, J=2.8 Hz). MS (DCI/NH$_3$) m/e 585 (M+H)$^+$, 463, 452, 372. IR (KBr) 1690, 1610, 1592, 1540, 1485. Anal calcd for C$_{35}$H$_{28}$N$_4$O$_3$S: C, 71.90; H, 4.83; N, 9.58. Found: C, 71.43; H, 4.95; N, 9.45.

EXAMPLE 21

Preparation of
3-(Pyridin-3-yl)-7-(1-methyl-6-phenylmethoxyindol-3-ylcarbonyl)- 1H,3H-pyrrolo[1,2-c]thiazole, The title compound was prepared by the procedure described in Example 2 using the compound resulting from Example 4, 3-(pyridin-3-yl)-7-(6-phenylmethoxyindol-3-yl)carbonyl-1H,3H-pyrrolo[1,2-c]thiazole, instead of 3-(pyridin- 3-yl)-7-(indol-3-yl)carbonyl-1H,3H-pyrrolo[1,2-c]thiazole and using methyl iodide instead of N,N-dimethylcarbamoylchloride, m.p. 172°–173° C. $^1$H NMR (DMSO-d6, 300 MHz) δ3.84 (s, 3H), 4.45 (d, 1H,J=5Hz), 4.62 (dd, 1H, J=15, 2Hz), 5.18 (s, 2H), 6.69 (d, 1H, J=3Hz), 6.76 (d, 1H, J=1Hz), 6.90 (d, 1H, J=3Hz), 6.95 (dd, 1H, J=9, 2Hz), 7.20 (d, 1H, J=2Hz), 7.32–7.53 (m, 6H), 7.65 (dt, 1H, J=8, 2Hz), 8.15 (d, 1H, 9Hz), 8.17 (s, 1H), 8.53–8.58 (m, 2H). MS (DCI/NH$_3$) m/e 466 (M+H)$^{30}$, 436, 374, 345. IR (CDCl3) 1595, 1570, 1525, 1245, 1080. Anal calcd for C$_{28}$H$_{23}$N$_3$O$_2$S: C, 72.24; H, 4.98; N, 9.03. Found: C, 72.34; H, 5.06; N, 8.88.

EXAMPLE 22

Preparation of
3-(Pyridin-3-yl)-7-(1-N-methylcarbamoyl-6-phenylmethoxyindol-3-ylcarbonyl)-1H,3H-pyrrolo[1,2-c]thiazole The title compound was prepared by the procedure described in Example 2 using the compound resulting from Example 4, 3-(pyridin-3-yl)-7-(6-phenylmethoxyindol-3-yl)carbonyl-1H,3H-pyrrolo[1,2-c]thiazole, instead of 3-(pyridin- 3-yl)-7-(indol-3-yl)carbonyl-1H,3H-pyrrolo[1,2-c]thiazole and using methylisocyanate instead of N,N-dimethylcarbamoylchloride, m.p. 212°–214° C. $^1$H NMR (DMSO-d6) δ3.84 (s, 3H), 4.45 (d, 1H, J=5Hz), 4.62 (dd, 1H, J=15, 2Hz), 5.18 (s, 2H), 6.69 (d, 1H, J=3Hz), 6.76 (d, 1H, J=1Hz), 6.90 (d, 1H, J= 3Hz), 6.95 (dd, 1H, J=9, 2Hz), 7.20 (d, 1H, J=2Hz), 7.327.53 (m, 6H), 7.65 (dt, 1H, J=8, 2Hz), 8.15 (d, 1H, 9Hz), 8.17 (s, 1H), 8.53–8.58 (m, 2H). MS (DCI/NH$_{3l}$) m/e 509 (M+H)$^+$, 452. Anal calcd for C$_{29}$H$_{24l N4}$O$_3$S: C, 68.49; H, 4.76; N, 11.02. Found: C, 68.43; H, 4.31; N, 11.47.

EXAMPLE 23

Preparation of
2-Oxide-3-(pyridin-3-yl)-7-(1-N,N-dimethylcarbamoyl-6-phenyllindol-3-ylcarbonyl)-1H,3H-pyrrolo[1,2-c]thiazole The title compound was prepared by the procedure described in Example 13 using the compound resulting from Example 12, 3-(pyridin-3-yl)-7-(1-N,N-dimethylcarbamoyl-6-phenylindol-3-yl)carbonyl-1H,3H-pyrrolo[1,2-c]thiazole, instead of 3-(pyridin-3-yl)-7-(1-tert-butyloxycarbonylidol-3-yl)carbonyl-1H,3H-pyrrolo[ 1,2-c]thiazole. $^1$H NMR (DMSO-d6, 300 MHz) δ3,09 (s, 0.12H), 3.11 (s, 0.88H), 4.29 (d, 0.12H, J=17Hz), 4.30 (d, 0.88H, J=17Hz), 4.72 (d, 0.88H, J=17Hz), 4.82 (d, 0.12H, J=17Hz), 6.72 (s, 0.88H), 6.77 (d, 0.12H, J=3Hz), 6.81 (s, 0.12), 6.96 (d, 0.12, J=3Hz), 7.05 (d, 0.88H, J=3Hz), 7.35–7.44 (m, 1H), 7.45– 7.53 (m, 4H), 7.65 (dd, 1H, J=9, 2Hz), 7.72 (dd, 2H, J=9, 1Hz), 7.86 (m, 1H), 8.34 (d, 1H, J=9Hz), 8.43 (m, 2H), 8.62 (dd, 0.88H, 4, 2Hz), 8.69 (dd, 0.12H, 4Hz, 2Hz), MS (DCI/NH$_3$) m/e 526 (M+NH4)$^+$, 509 (M+H)$^+$, 461, 403, 388. Anal calcd for $C_{29}H_{24}N_4O_3S$: C, 68.49; H, 4.76; N, 11.02. Found: C, 70.44; H, 5.33; N, 12.05.

EXAMPLE 24

Preparation of
1,1-Dimethyl-3-(pyridin-3-yl)-7-(1-N,N-dimethylcarbamoyl-
6-phenylindol-3-ylcarbonyl)-1H,3H-pyrrolo[1,2-c]thiazole The title compound was prepared by the procedure described in Example 19 using, 6-phenylindole instead of indole. $^1$H NMR (CDCl$_3$, 300 MHz) δ2.04 (s, 3H), 2.07 (s, 3H), 6.22 (d, 1H, J=3Hz), 6.53 (s, 1H), 6.75 (d, 1H, J=3Hz), 7.36 (m, 1H), 7.47 (m, 2H), 7.60 (dd, 1H, J=7.5, 1.5Hz), 7.67 (m, 2H), 7.81 (m, 2H), 7.92 (s, 1H), 8.37 (d, 1H, J=9Hz), 8.67 (b, 2H). MS (DCI/NH$_3$) m/e 521 (M+H)$^+$, 398.

EXAMPLE 25

Preparation of
1,1-Dimethyl-3-(pyridin-3-yl)-7-[6-(4-methoxyphenyl)indol-3-ylcarbonyl]-1H,3H-pyrrolo[1,2-c]thiazole, Step 1, Preparation of 6-(4-methoxyphenyl)-1l-tert-butoxycarbonylindole To a solution of 1-tert-butoxycarbonyl-6-bromoindole (5.0 g, 17 mmol) in toluene (200 mL) was added tetrakis(triphenylphosphine)palladium(0) (0.94 g, 0.84 mmol), 2N aqueous Na$_2$CO$_3$ (100 mL), and a solution of 4-methoxyboronic acid in ethanol (50 mL). The 2-phase mixture was heated at 110°–125° C. for two hours. The reaction mixture was cooled to ambient temperature and the layers where separated. The aqueous phase was extracted twice with ether. The combined organic layers where washed twice with brine, dried over MgSO$_4$, filtered, and concentrated in vacuo to give a brown oil. Chromatography on silica gel (250 g, 5% ether, hexanes) afforded 6-(4-methoxyphenyl)-1-tert-butoxycarbonylindole (3.2 g, 58%).

Step 2. Preparation of 6-(4-methoxyphenyl)indole

To a suspension of 6-(4-methoxyphenyl)-1-tert-butoxycarbonylindole (3.9 g, 12 mmol) in methanol (50 mL) was added 1N methanolic NaOH (60 mL) and CH$_2$Cl$_2$ (20 mL). The reaction was stirred for one hour at ambient temperature and 1.5 hours at reflux. The reaction mixture was cooled to ambient temperature and H$_2$O (50 mL) was added to dissolve all solids. The two-phase mixture was poured into CHCl$_3$ and the layers where separated. The organic phase was washed with brine, dired over MgSO$_4$, filtered, and concentrated in vacuo. Flash chromatography on silica gel (100 g, 25% ethyl acetate, hexanes) afforded 6-(4-methoxyphenyl)indole as white flakes (2.2 g, 81%).

Step 3. Preparation of
1,1-Dimethyl-3-(pyridin-3-yl)-7-[6-(4-methoxyphenyl)indol- 3-ylcarbonyl]-1H,3H-pyrrolo[1,2-c]thiazole The title compound was prepared by the procedure described in Example 17 using 6-(4-methoxyphenyl)indole instead of indole, m.p. 236°–239° C. $^1$H NMR (CDCl$_3$, 300 MHz) δ2.06 (s, 3H), 2.08 (s, 3H), 4.06 (s, 3H), 6.19 (d, J=3 Hz, 1H), 6.49 (s, 1H), 6.70 (d, J=3 Hz, 1H), 6.99 (d, J=9 Hz, 2H), 7.36 (dd, J=7.5, 6.0 Hz, 1H), 7.51 (dd, J=7.5, 1.5 Hz, 1H), 7.58 (m, 3H), 7.71 (dt, J=9.0, 1.5 Hz), 7.81 (d, J=3 Hz, 1H), 8.40 (d, J=9 Hz, 1H), 8.62 (b, 3H), MS (DCI/NH$_3$) m/e 480 (M+1)$^+$.

EXAMPLE 36

Preparation of
1,1-Dimethyl-3-Dimethyl-3-(pyridin-3-yl)-7-[1-N,N-dimethylcarbamoyl-
6-(4-methoxyphenyl)indol-3-ylcarbonyl]-1H,3H-pyrrolo[1,2-c]thiazole The title compound was prepared by the procedure described in Example 2 using the compound resulting from Examples 25, 1,1-dimethyl-3-(pyridin-3-yl)- 7-[6-(4-methoxyphenyl)indol-3-ylcarbonyl]-1H,3H-pyrrolo[1,2-c]thiazole, instead of 3-(pyridin-3-yl)-7-(indol-3-yl)carbonyl-1H,3H-pyrrolo[1,2-c]thiazole. m.p. 271°–273° C. $^1$H NMR (CDCl$_3$, 300 MHz) δ2.06 (s, 3H), 2.07 (s, 3H), 3.15 (s, 3H), 3.86 (s, 3H), 6.20 (d, J=3 Hz, 1H), 6.51 (s, 1H), 6.73 (d, J=3 Hz, 1H), 6.99 (dd, J=9.0, 6.0 Hz, 2H), 7.37 (m, 1H), 7.55 (dd, J=9.0, 1.5 Hz, 1H), 7.59 (d, J=9 Hz, 2H), 7.70 (dt, J=9.0, 1.5 Hz, 1H), 7.73 (d, J=1.5 Hz, 1H), 7.89 (s, 1H), 8.34 (d, J=9 Hz, 1H), 8.64 (b, 2H), MS (DCI/NH$_3$) m/e 551 (M+1)$^+$, 428. Anal calcd for $C_{32}H_{30}N_4O_3S$: C, 69.80; H, 5.49; N, 10.17. Found: C, 69.57; H, 5.59; N, 9.89.

EXAMPLE 27

Preparation of
3-[Pyridin-3-yl)-7-(1-carbophenoxy-6-phenylmethoxyindol-
3-ylcarbonyl)-1H,3H-pyrrolo[1,2-c]thiazole The desired compound was prepared according to the method of Example 2, except substituting 3-(pyridin-3-yl)-7-(6-phenylmethoxyindol-3-)carbonyl-1H,3H-pyrrolo[ 1,2-c]thiazole, prepared as in Example 4 for 3-(pyridin-3-yl)-7-(indol-3-yl)carbonyl- 1H,3H-pyrrolo[1,2-c]thiazole and substituting phenyl chloroformate for N,N-dimethylcarbamoyl chloride. $^1$H NMR (DMSO-d6, 300 MHz) δ4.45 (d, 1H, J=15Hz), 4.62 (dd, 1H, J=15Hz, 2Hz), 5.16 (s, 2H), 6.69 (d, 1H, J=3Hz), 6.76 (s, 1H), 6.85 (d, 1H, J=3Hz), 7.12 (dd, 1H, J=9Hz, 3Hz), 7.26–7.52 (m, 11H), 7.60– 7.68 (m, 1H), 7.77 (d, 1H, J=3Hz), 8.08 (d, 1H, J=9Hz), 8.30 (s, 1H), 8.51–8.54 (m, 2H), MS (DCI/NH$_3$) m/e 572 (M+H)$^+$.

EXAMPLE 28

Preparation of
3-(Pyridin-3-yl)-7-[6-(4-fluorophenyl)indol-3-ylcarbonyl]- 1H,3H-pyrrolo[1,2-c]thiazole Step 1. Preparation of 6-(4-fluorophenyl)indole The desired compound was prepared according to the method of Example 25, step 1, except substituting 4-fluorophenylboronic acid for 4-methoxyphenylboronic acid, and 6-bromoindole for 1-tert-butoxy-6-bromoindole.

Step 2. Preparation of
3-(Pyridin-3-yl)-7-[6-(4-fluorophenyl)indol-3-ylcarbonyl]- 1H,3H-pyrrolo[1,2-c]thiazole 3-(Pyridin-3-yl)-7-[6-(4-fluorophenyl)indol-3-ylcarbonyl]- 1H,3H-pyrrolo[1,2-c]thiazole was prepared according to the method of Example 1, except substituting 6-(4-fluorophenyl)indole for indole. m.p. 248°–252° C. $^1$H NMR (DMSO-d6, 300 MHz) δ4.47 (d, 1H, J=15Hz), 4.64 (dd, 1H, J=15Hz, 2Hz), 6.71 (d, 1H, J=3Hz), 6.78 (s, 1H), 6.90 (d, 1H, J=3Hz), 7.30 (t, 2H, J=9Hz), 7.41–7.50 (m, 2H), 7.63–7.78 (m, 4H), 8.27 (d, 1H, J=3Hz), 8.31 (d, 1H, J=8Hz), 8.55–8.60 (m, 2H), 11.96 (d, 1H, J=3Hz). MS (DCI/NH$_3$) m/e 440 (M+H)$^+$, 406, 315, 212, IR (KBr) 3420, 1590, 1510, 1425, 1230, 860. Anal calcd for C$_{26}$H$_{18}$N$_3$OSF: C, 71.05; H, 4.13; N, 9.56. Found: C, 70.06; H, 4.19; N, 9.31.

EXAMPLE 29

Preparation of 3-(Pyridin-3-yl)-7-[1-N,N-dimethylcarbamoyl-6-(4-fluorophenyl)indol-3-ylcarbonyl]-1H,3H-pyrrolo[1,2-c]thiazole The title compound was prepared by the procedure described in Example 2 using the compound resulting from Example 28, 3-(pyridin-3-yl)- 7-[6-(4-fluorophenyl)indol-3-ylcarbonyl]-1H,3H-pyrrolo[1,2-c]thiazole, instead of 3-(pyridin-3-yl)-7-(indol-3-yl)carbonyl-1H,3H-pyrrolo[1,2-c]thiazole, m.p. 212°–214°0 1 C. $^1$H NMR (DMSO-d6, 300 MHz) δ3.08 (s, 6H), 4.50 (d, 1H, J=15Hz), 4.67 (dd, 1H, J=15. 2Hz), 6.73 (d, 1H, J=3Hz), 6.80 (d, 1H, J=1Hz), 6.92 (d, 1H, J=3Hz), 7.32 (t, 2H, J=9Hz), 7.44 (dd, 1H, J=5, 8Hz), 7.61 (dd, 1H, J=9, 1Hz), 7.68 (dt, 1H, J=8, 1Hz), 7.72–7.84 (m, 3H), 8.32 (d, 1H, J=9Hz), 8.37 (s, 1H), 8.55–8.60 (m, 2H), MS (DCI/NH$_3$) m/e 511 (M+H)$^+$, 465, 387. IR (KBr) 1690, 1605, 1540, 1515, 1480. Anal calcd for C$_{29}$H$_{23}$FN$_4$O$_2$S; C, 68.22; H, 4.54; N, 10.97. Found: C, 67.46; H, 4.58; N, 10.67.

EXAMPLE 30

Preparation of 3-(Pyridin-3-yl)-7-(1-N-methylcarbamoyl-6-phenylindol-3-ylcarbonyl)-1H,3H-pyrrolo[1,2-c]thiazole The title compound was prepared by the procedure described in Example 2 using the compound resulting from Example 10, 3-(pyridin-3-yl)-7-(6-phenylindol-3-yl)carbonyl- 1H,3H-pyrrolo[1,2-c]thiazole, instead of 3-(pyridin-3-yl)-7-(indol-3-yl)carbonyl- 1H,3H-pyrrolo[1,2-c]thiazole and using methylisocyanate instead of N,N-dimethylcarbamoyl chloride. m.p. 238°–240° C. $^1$H NMR (DMSO-d6, 300 MHz) δ 2.89 (d, 3H, J=4Hz), 4.51 (d, 1H, J=Hz), 4.68 (dd, 1H, J=15, 2Hz), 6.77 (d, 1H) J=3Hz), 6.81 (d, 1H, J=1Hz), 7.06 (d, 1H, 3Hz), 7.35–7.53 (m, 4H), 7.63 (dd, 1H, J=9, 1Hz), 7.66 (m, 3H), 8.32 (d, 1H, J=9Hz), 8.53–8.63 (m, 5H), MS (DCI/NH$_3$) m/e 479 (M+H)$^+$, 422, 298. IR (KBr) 1710, 1600, 1530, 1470. Anal calcd for C$_{28}$H$_{22}$N$_4$O$_2$S: C, 70.27; H, 4.63; N, 11.71. Found: C, 69.63; H, 4.87; N, 11.20.

EXAMPLE 31

Preparation of 3-(Pyridin-3-yl)-7-[1-N-methylcarbamoyl-6-(4-fluorophenyl)indol-3-ylcarbonyl]-1H,3H-pyrrolo[1,2-c]thiazole The title compound was prepared by the procedure described in Example 2 using the compound resulting from Example 28, 3-(pyridin-3-yl)- 7-[6-(4-fluorophenyl)indol-3-ylcarbonyl]-1H,3H-pyrrolo[1,2-c]thiazole, instead of 3-(pyridin-3-yl)-7-(indol-3-yl)carbonyl-1H,3H-pyrrolo[ 1,2-c]thiazole and using methylisocyanate instead of N,N-dimethylcarbamoyl chloride. m.p. 227°–228° C. $^1$H NMR (DMSO-d6, 300 MHz) δ2.89 (d, 3H, J=4Hz), 4.51 (d, 1H, J=15Hz), 4.67 (dd, 1H, J=15, 2Hz), 6.78 (d, 1H, J=3Hz), 6.81 (d, 1H, J=1Hz), 7.05 (d, 1H, J=3Hz), 7.32 (t, 2H, J=9Hz), 7.45 (dd, 1H, J=8, 5Hz), 7.61 (dd, 1H, J=9, 1Hz), 7.65–7.77 (m, J=3H), 8.31 (d, 1H), J=8Hz). 8.50–8.63 (m, 5H). MS (DCI/NH$_3$) m/e 497 (M+H)$^+$, 400. IR (KBr) 1712, 1600, 1535, 1510, 1430. Anal calcd for C$_{28}$H$_{21}$N$_4$O$_2$SF: C, 67.73; H, 4.26; N, 11.28. Found: C, 67.05; H, 4.31; N, 10.94.

EXAMPLE 32

Preparation of 1,1-Dimethyl-3-(pyridin-3-yl)-7-[1-N-methylcarbamoyl-6-(4-methoxyphenyl)indol-3-ylcarbonyl]-1H,3H-pyrrolo[1,2-c]thiazole The title compound was prepared by the procedure described in Example 2 using the compound resulting from Example 25, 1,1-dimethyl-3-(pyridin-3-yl)- 7-[6-(4-methoxyphenyl)indol-3-ylcarbonyl]-1H,3H-pyrrolo[1,2-c]thiazole, instead of 3-(pyridin-3-yl)-7-(indol-3-yl)carbonyl-1H,3H-pyrrolo[1,2-c]thiazole and using methylisocyanate instead of N,N-dimethylcarbamoyl chloride. $^1$H NMR (CDCl$_3$, 300 MHz) δ2.03 (s, 6H), 3.12 (s, 3H), 3.14 (s, 3H), 3.86 (s, 3H), 6.16 (b, 1H), 6.19 (d, 1H, J=3Hz), 6.51 (s, 1H), 6.70 (d, 1H, J=3Hz), 6.96 (d, 2H, J=9Hz), 7.49 (m, 1H), 7.50–7.60 (c, 3H), 7.73 (d, 1H, J=9Hz), 7.96 (s, 1H), 8.06 (s, 1H), 8.24 (d, 1H, J=9Hz), 8.58–8.70 (b, 2H). MS (DCI/HN$_3$) 537 (M+H)$^+$, 480.

EXAMPLE 33

Preparation of 3-(1-methylpyridin-3-yl)-7-(1-N,N-dimethylcarbamoyl-6-phenylindol-3-ylcarbonyl)-1H,3H-pyrrolo[1,2-c]thiazole To a solution of 3-(pyridin-3-yl)-7-(1-N,N-dimethylcarbamoyl-6-phenylindol- 3-ylcarbonyl)-1H,3H-pyrrolo[1,2-c] thiazole (100 mg, 0.20 mmol), prepared as in Example 11, in acetone (15 mL) was added iodomethane (19 μL, 0.30 mmol) via syringe. The reaction mixture was stirred at reflux for 18 hours. The reaction mixture was cooled to ambient temperature and iodomethane (7 μL) was added and the reaction mixture was warmed back to reflux and stirred for 18 hours. The reaction mixture was concentrated in vacuo and the residue taken up in methanol. Crude material was precipitated by addition of ether. Pure 3-(1-Methylpyridin-3-yl)-(1-N,N-dimethylcarbamoyl- 6-phenylindol-3-ylcarbonyl)-1H,3H-pyrrolo[1,2-c]thiazole (38 mg), was obtained by recrystallization from methanol, ether, m.p. 171°–174° C. $^1$H NMR (D$_3$COD, 300 MHz) δ3.17 (s, 6H), 4.44 (s, 3H), 4.57 (d, 1H, J=15Hz), 4.76 (dd, 1H, J=15, 2Hz), 6.76 (d, 1H, J=3Hz), 6.87 (d, 1H, J=2Hz), 6.98 (d, 1H, J=3Hz), 7.35 (t, 1H, J=8Hz), 7.47 (t, 2H, J=8Hz), 7.62 (dd, 1H, J=9, 2Hz), 7.65– 7.72 (m, 2H), 7.81–7.82 (m, 1H), 8.10 (dd, 1H, J=6, 8Hz), 8.25 (s, 1H), 8.32 (d, 1H, J=9Hz), 8.45 (d, J=9Hz), 8.91 (d, 1H, J=6Hz), 8.97 (s, 1H), MS (FAB) m/e 507 (M+1)$^+$. IR (KBr) 1690, 1610, 1535, 1475. Anal calcd for C$_{30}$H$_{27}$IN$_4$O$_2$S: C, 56.79; H, 4.29; N, 8.83. Found: C, 54.50; H, 4.12; N, 8.45.

EXAMPLE 34

Preparation of
3-(1-Oxide-pyridin-3-yl)-7-(1-N,N-dimethylcarbamoyl-6-phenylindol-3-ylcarbonyl)-1H,3H-pyrrolo[1,2-c]thiazole

Step 1. Preparation of 3-[1-(2,4-dinitrophenyl)pyridin-3-yl]-7-(1-N,N-dimethylcarbamoyl-6-phenylindol-3-yl)carbonyl-1H,3H-pyrrolo[1,2-c]thiazole A mixture of 3-(pyridin-3-yl)-7-(1-N,N-dimethylcarbamoyl-6-phenylindol-3-yl)carbonyl- 1H,3H-pyrrolo[1,2-c]thiazole (500 mg, 1.01 mmol), prepared as described in Example 12, and 2,4-dinitrophenyl-p-toluene sulfonate (515 mg, 1.5 mmol), prepared according to the method described in J. Amer. Chem. Soc., 74, 5859 (1952), in acetonitrile (10 mL) was heated at 100°–110° C. for 23 hours. The heterogeneous reaction mixture was cooled to ambient temperature, ether (30 mL) was added, and the slurry was stirred for 10 min. The solid was filtered off and recrystallized from methanol to afford 3-[1-(2,4-dinitrophenyl)pyridin-3-yl]-7-(1-N,N-dimethylcarbamoyl-6-phenylindol-3-yl)carbonyl-1H,3H-pyrrolo[1,2-c]thiazole (608 mg) as a tan solid.

Step 2. Preparation of 3-(1-Oxide-pyridin-3-yl)-7-(1-N,N-dimethylcarbamoyl-6-phenylindol-3-ylcarbonyl)-1H,3H-pyrrolo[1,2-c]thiazole To a suspension of 3-[1-(2,4-dinitrophenyl)pyridin-3-yl]-7-(1-N,N-dimethylcarbamoyl- 6-phenylindol-3-yl)carbonyl-1H,3H-pyrrolo[1,2-c]thiazole (250 mg, 0.30 mmol), prepared as in step 1, in methanol (6 ml) was added aqueous hydroxylamine (1N, 0.60 mmol) and the reaction mixture was heated at 90° C. for three hours. The reaction mixture was concentrated in vacuo and triturated with either to give a reddish powder. Pure 3-(1-Oxide-pyridin-3-yl)-7-(1-N,N-dimethylcarbamoyl-6-phenylindol- 3-ylcarbonyl)-1H,3H-pyrrolo[1,2-c]thiazole was obtained by flash chromatography on silica gel(24:1 $CH_2Cl_2$, 5% aqueous methanol). $^1$H NMR ($CD_3OD$, 300 MHz) δ3.18 (s, 6H), 4.52 (d, 1H, J=15.0Hz), 4.68 (dd, 1H, J=1.5, 15.0Hz), 6.69 (d, 1H, J=1.0Hz), 6.72 (d, 1H, J=3.0Hz), 6.95 (d, 1H, J=3.0Hz), 7.34 (m, 1H), 7.43–7.50 (c, 3H), 7.55 (dd, 1H, J=7.0, 8.5Hz), 7.61 (dd, 1H, J= 1.5, 9.0Hz), 7.69 (d, 2H, J=8.0Hz), 7.82 (d, 1H, J=1.0Hz), 8.25 (s, 1H), 8.28 (br s, 1H), 8.30 (d, 1H, J=8.0Hz), 8.31 (m, 1H). MS (DCI/$NH_3$) 509 (M+1), 493.

EXAMPLE 35

Preparation of
3-(1-Oxide-pyridin-3-yl)-7-(1-N-methylcarbamoyl-6-phenylindol-3-ylcarbonyl)-1H,3H-pyrrolo[1,2-c]thiazole The title compound is prepared by the procedure described in Example 34 using the compound resulting from Example 30, 3-(pyridin-3-yl)-7-(1-N-methylcarbamoyl-6-phenylindol-3-ylcarbonyl)-1H,3H-pyrrolo[1,2-c]thiazole instead of 3-(pyridin-3-yl)- 7-(1-N,N-dimethylcarbamoyl-6-phenylindol-3-yl)carbonyl- 1H,3H-pyrrolo[1,2-c]thiazole. $^1$H NMR ($CD_3OD$, 300 MHz) δ3,00 (s, 3H), 4.52 (d, 1H, J=15.0Hz), 4.66 (dd, 1H, J=1.5, 15.0Hz), 6.69 (d, 1H, J=1.0Hz), 6.73 (d, 1H, J=3.0Hz), 7.03 (d, 1H, J=3.0Hz), 7.34 (m, 1H), 7.45–7.48 (c, 3H), 7.55 (dd, 1H, J=7.0, 9.0Hz), 7.61 (dd, 1H, J=1.5, 9.0Hz), 7.70 (d, 2H, J=8.0Hz), 8.23 (d, 1H, J=1.5Hz), 8.29 (d, 1H, J=8.0Hz), 8.30 (dd, 1H, J=1.5, 7.0Hz), 8.49 (s, 1H), 8.50 (s, 1H), MS (FAB) 495 (M+1)$^+$ 479.

EXAMPLE 36

Preparation of
1,1-Dimethyl-3-(pyridin-3-yl)-7-[6-(4-fluorophenyl)indol-3-ylcarbonyl]-1H,3H-pyrrolo[1,2-c]thiazole The title compound was prepared by the procedure described in Example 17 using 6-(4-fluorophenyl)indole, prepared as in Example 28, instead of indole. $^1$H NMR ($CDCl_3$, 300 MHz) δ2.05 (s, 6H), 6.18 (d, 1H, J=3Hz), 6.51 (s, 1H), 6.69 (d, 1H, J=3Hz), 7.13 (t, 2H, J=14.9Hz), 7.43 (m, 1H), 7.49 (dd, 1H, J=9, 1.5Hz), 7.58 (m, 3H), 7.78 (m, 1H), 7.80 (d, 1H, J=3Hz), 8.42 (d, 1H, J=9Hz), 8.61 (d, 1H, J=1.5Hz), 8.65 (m, 1H), 8.98 (bs, 1H), MS (CDI/$NH_3$) 468 (M+H)$^+$.

EXAMPLE 37

Preparation of
3-(Pyridin-3-yl)-7-(1-carbamoyl-6-phenylmethoxyindol-3-ylcarbonyl)- 1H,3H-pyrrolo[1,2-c]thiazole

Step 1. Preparation of 3-(Pyridin-3-yl)-7-[1-(4-nitrophenoxycarbonyl)-6-phenylmethoxyindol-3-ylcarbonyl]-1H,3H-pyrrolo[1,2-c]thiazole To a solution of 3-(pyridin-3-yl)-7-(6-phenylmethoxyindol-3-yl)carbonyl- 1H,3H-pyrrolo[1,2-c]thiazole (200 mg, 0.443 mmol), prepared as in Example 4, in DMF (12 mL) was added NaH (60% oil dispersion, 19 mg, 0.465 mmol) and the reaction mixture was stirred for 7 min at ambient temperature. 4-nitrophenyl chloroformate (94 mg, 0.45 mmol) was added and the amber solution was stirred for two hours at ambient temperature. The reaction mixture was partitioned between $H_2O$ and ethyl acetate. The organic phase was dried over $MgSO_4$, filtered, and concentrated. The title compound (98 mg), was purified by flash chromatography on silica gel (60 g, 1:1 ethyl acetate, hexanes).

Step 2. Preparation of Preparation of 3-(Pyridin-3-yl)-7-(1-carbamoyl-6-phenylmethoxyindol-3-ylcarbonyl)-1H,3H-pyrrolo[1,2-c]thiazole Several drops of anhydrous ammonia where condensed into a solution of 3-(Pyridin- 3-yl)-7-[1-(4-nitrophenoxycarbonyl)-6-phenylmethoxyindol-3-ylcarbonyl]- 1H,3H-pyrrolo[1,2-c]thiazole (50 mg) in 1:1 THF methanol (4 mL) at −78° C. The reaction mixture was stirred for 1 hour at −78° C. The reaction mixture was warmed to ambient temperature and concentrated in vacuo. The crude material was purified by flash chromatography on silica gel (50 g, ethyl acetate) to yield 32 mg of 3-(Pyridin-3-yl)- 7-(1-carbamoyl-6-phenylmethoxyindol-3-ylcarbonyl)-1H,3H-pyrrolo[1,2-c]thiazole. $^1$H NMR (DMSO-d6, 300 MHz) δ4.48 (d, 1H, J=15Hz), 4.55 (dd, 1H, J=15, 2Hz), 5.15 (s, 2H), 6.74 (d, 1H, J=3Hz), 6.79 (d, 1H, J=1Hz), 7.01 (d, 1H, J=3Hz), 7.04 (dd, 1H, J=3, 9Hz), 7.30–7.52 (m, 6H), 7.68 (d, 1H, J=8, 2Hz), 7.89 (s, 2H), 7.98 (d, 1H, J=3Hz), 8.11 (d, 1H, J=9Hz), 8.41 (s, 1H), 8.55–8.59 (m, 2H). MS (DCI/$NH_3$) m/e 495 (M+H)$^+$, 452. IR (KBr) 1710, 1600, 1540, 1480, Anal calcd for $C_{28}H_{22}N_4O_3S$: C, 68.00; H, 4.48; N, 11.33. Found: C, 67.14;

EXAMPLE 38

Preparation of 3-(Pyridin-3-yl)-7-[6-(4-methoxyphenyl)indol-3-yl]carbonyl- 1H,3H-pyrrolo[1,2-c]thiazole The desired compound was prepared using the procedure of example 28, except using 4-methoxybromobenzene instead of 4-fluorobromobenzene, m.p. 246°–248° C. $^1$H NMR (DMSO-d6, 300 MHz) δ3.81 (s, 3H), 4.47 (d, 1H, J=15Hz), 4.64 (dd, 1H, J=15Hz, 2Hz), 6.70 (d, 1H, J=3Hz). 6.77 (s, 1H), 6.90 (d, 1H, J=3Hz), 7.04 (d, 2H, J=2Hz), 7.41–7.48 (m, 2H), 7.61–6.69 (m, 4H), 8.23 (d, 1H, J=2Hz), 8.29 (d, 1H, J=9Hz), 8.53–8.59 (m, 2H), 11.90 (s, 1H), MS (DCI/NH$_3$) m/e 452 (M+H)$^+$. IR (KBr) 1605, 1575, 1510. Anal calcd for $C_{27}H_{21}N_3O_2S$: C, 71.82; H, 4.69; N, 9.31. Found: C, 70.97; H, 4.74; N, 9.06.

EXAMPLE 39

Preparation of 3-(1-Oxide-pyridin-3-yl)-7-[1-N,N-dimethylcarbamoyl-6-(4-fluorophenyl)indol-3-ylcarbonyl]-1H,3H-pyrrolo[1,2-c]thiazole The title compound is prepared by the procedure described in Example 34 using the compound resulting from Example 29, 3-(pyridin-3-yl)-7-[1-N,N-dimethylcarbamoyl-6-(4-fluorophenyl)indol-3-ylcarbonyl]- 1H,3H-pyrrolo[1,2-c]thiazole instead of 3-(pyridin-3-yl)-7-(1-N,N-dimethylcarbamoyl- 6-phenylindol-3-yl)carbonyl-1H,3H-pyrrolo[1,2-c]thiazole. $^1$H NMR (CD$_3$OD, 300 MHz) δ3.15 (s, 6H), 4.48 (d, 1H, J=15 Hz), 4.65 (1H, J=15, 2Hz), 6.68 (d, 1H, J=1Hz), 6.73 (d, 1H, J=3Hz), 6.95 (1H, J=4Hz), 7.2 (t, 2H, J=9Hz), 7.45 (m, 1H), 7.5–7.6 (cm, 2H), 7.65–7.75 (m, 2H), 7.8 (d, 1H, J=1Hz), 8.23–8.33 (m, 4H). MS (FAB) m/e 527. (R (CDCl$_3$) 1690, 1600, 1540, 1510, 1480, 1440, 1390, 1225, 1180.

EXAMPLE 40

Preparation of 3-(Pyridin-3-yl)-7-[1-N,N-dimethylcarbamoyl-6-(4-methoxyphenyl)indol-3-ylcarbonyl]-1H,3H-pyrrolo[1,2-c]thiazole The title compound was prepared by the procedure described in Example 2 using the compound resulting from Example 38, 3-(pyridin-3-yl- 7-[6-(4-methoxyphenyl)indol-3-yl]carbonyl-1H,3H-pyrrolo[1,2-c]thiazole, instead of 3-(pyridin-3-yl)-7-(indol-3-yl)carbonyl-1H,3H-pyrrolo[1,2-c]thiazole. m.p. 204°– 205° C. $^1$H NMR (DMSO-d6, 300 MHz) δ3.08 (s, 6H), 3.81 (s, 3H), 4.49 (d, 1H, J=15Hz), 4.68 (dd, 1H, J=15, 2Hz), 6.73 (d, 1H, J=3Hz,), 6.80 (s, 1H), 6.91 (d, 1H, J=3Hz), 7.05 (d, 2H, J=9Hz), 7.45 (dd, 1H, J=5, 8Hz), 7.58 (dd, 1H, J=1, 8Hz), 7.63–7.70 (m, 3H), 7.78 (s, 1H), 8.29 (d, 1H, J=9Hz), 8.33 (s, 1H), 8.55– 8.59 (m, 2H), MS (DCI/NH$_3$) m/e 523 (M+H)$^+$. IR (KBr) 1690, 1605, 1540, 1520, 1480, Anal calcd for $C_{20}H_{26}N_4O_3S$: C, 68.95; H, 5.01; N, 10.72. Found: C, 67.22; H, 5.05; N, 9.93.

EXAMPLE 41

Preparation of 3-(Pyridin-3-yl)-7-(6-pyrid-4-ylindol-3-ylcarbonyl)- 1H,3H-pyrrolo[1,2-c]thiazole

Step 1. Preparation of 6-indolylboronic acid

To a suspension of potassium hydride (35% oil dispersion, 0.84 g, 7.33 mmol) in THF (10 mL) at 0° C. was added a solution 6-bromoindole (1.43 g, 7.20 mmol) in THF (6 mL). The reaction mixture was stirred for 15 min at 0° C., then cooled to −78° C. and t-butyllithium solution (1.7M in pentance, 14.6 mmol) was added quickly dropwise. After stirring for 20 min. at −78° C., a solution of tri-n-butyl borate (3.94 mL, 14.6 mmol) in THF (4 mL) was added quickly. The reaction mixture was stirred for 1 hour at −78° C. and 2hours at 0° C. The reaction was quenched by addition of 1N aqueous HCl (15 mL) and stirring for 30 min at 0° C. The reaction mixture was partitioned between H$_2$O and ether. The aqueous phase was extracted 3 times with ether. The combined ethereal extracts where washed 3 times with cold 1N aqueous NaOH, and then discarded. The basic aqueous extracts where acidified with 1N aqueous HCl and extracted 3 times with ether. The combined organic layers where dried over Na$_2$SO$_4$, filtered, and concentrated in vacuo to give 6-indolylboronic acid (0.86 g) which was used without further purification.

Step 2. Preparation of 6-(3-pyridinyl)indole

The desired compound was prepared according to the method of Example 25, step 1, except substituting 6-indolylboronic acid, prepared as in step 1 for 4-methoxyphenylboronic acid, and 3-bromopyridine for 1-tert-butoxycarbonyl-6-bromoindole.

Step 3. Preparation of 3-(Pyridin-3-yl)-7-(6-pyrid-3-ylindol-3-ylcarbonyl)- 1H,3H-pyrrolo[1,2-c]thiazole To a suspension of 3-(pyridin-3-yl)-3-yl)-1H,3H-pyrrolo [1,2-c]thiazole-7-carboxylic acid (0.84 g, 3.43 mmol), prepared as described in U.S. Pat. No. 4,529,728, in dry CHCl$_3$ under N$_2$ was added NaH (60% oil dispersion, 151 mg, 3.77 mmol) in a single portion. The suspension was stirred for 30 min at ambient temperature, then 2 drops of DMF where added, followed by oxalyl chloride (0.34 mL, 3.77 mmol). The suspension was stirred for 30 min at ambient temperature.

In a separate flask, methylmagnesium bromide solution (3.0M in ether, 2.3 mL, 6.9 mmol) was added to a suspension of 6-(3-pyridinyl)indole, prepared in step 2, in ether (35 mL). The yellow suspension was stirred for 30 min at ambient temperature, after which zinc chloride solution (1.0M in ether, 6.9 mmol) was added quickly and the suspension was stirred for a further 20 min.

The solution of acid chloride in CHCl$_3$ was cannulated into the indolylzinc chloride suspension and the reaction mixture was stirred for 18 hours at ambient temperature. The reaction was quenched with saturated aqueous NH$_4$Cl and extracted with THF, ethyl acetate, and again with THF. The combined organic layers where dried over MgSO$_4$, filtered, and concentrated in vacuo. Flash chromatography on silica gel (200 g, 7% methanol, CHCl$_3$) afforded 3-(Pyridin-3-yl)-7-(6-pyrid-3-ylindol- 3-ylcarbonyl)-1H,3H-pyrrolo[1,2-c] thiazole (116 mg). m.p. 270°–271° C. $^1$H NMR (DMSO-d6, 300 MHz) δ4.48 (d, 1H, J=15Hz), 4.65 (dd, 1H, J=2, 15Hz), 6.71 (d, 1H, J=3Hz), 6.78 (d, 1H, J=1Hz), 6.91 (d, 1H, J=3Hz), 7.45 (dd, 1H, J=8, 5Hz), 7.50 (dd, 1H, J=5, 8Hz), 7.55 (dd, 1H, J=9, 2Hz), 7.66 (dt, 1H, J=9, 2Hz), 7.79 (d, 1H, J=2Hz), 8.30 (s, 1H), 8.37 (d, 1H, J=9Hz), 8.53–8.59 (d, 1H, J=9Hz), 8.53– 8.59 (m, 3H), 8.94 (d, 1H, J=2Hz). MS (DCI/NH$_3$) m/e 423 1 (M+H)$^+$, 223, 195. IR (KBr) 3180, 1585, 1575, 1540. Anal calcd for C$_{25}$H$_{18}$N$_4$OS: C, 71.07; H, 4.29; N, 13.26. Found: C, 70.14; H, 4.28; N, 12.93.

EXAMPLE 42

Preparation of
3-(Pyridin-3-yl)-7-(1-N,N-dimethylcarbamoyl-6-pyrid-4-ylindol-3-ylcarbonyl)-1H,3H-pyrrolo[1,2-c]thiazole The title compound was prepared by the procedure described in Example 2 using the compound resulting from Example 41, 3-(pyridin-3-yl)-7-(6-pyridin-4-ylindol- 3-ylcarbonyl)-1H,3H-pyrrolo[1,2-c]thiazole, instead of 3-(pyridin-3-yl)-7-(indol- 3-yl)carbonyl-1H,3H-pyrrolo[1,2-c]thiazole, $^1$H NMR (DMSO-d6, 300 MHz) δ3.09 (s, 6H), 4.50 (d, 1H, J=15Hz), 4.68 (dd, 1H, J=2, 15Hz), 6.74 (d, 1H, J=3Hz), 6.80 (d, 1H, J=1Hz), 6.92 (d, 1H, J=3Hz), 7.45 (dd, 1H, J=5. 8Hz), 7.51 (dd, 1H, J=5, 8Hz), 7.65–7.71 (m, 2H), 7.90 (d, 1H, J=1Hz), 8.14 (dt, 1H, J=2, 8Hz), 8.36 (d, 1H, J=8Hz), 8.40 (s, 1H), 8.56–8.61 (m, 3H), 8.95 (d, 1H, J=2Hz). MS (DCI/NH$_3$) m/e 494 (M+H), 387, 337. R (KBr) 2920, 1690, 1602, 1530, 1480. Anal calcd for C$_{28}$H$_{23}$N$_5$O$_2$S: C, 68.14; H, 4.70; N, 14.19. Found: C, 67.27; H, 4.75; N, 14.06.

EXAMPLE 43

Preparation of
3-(Pyridin-3-yl)-7-[1-N-methylcarbamoyl-6-(4-methoxyphenyl)indol-3-ylcarbonyl]-1H,3H-pyrrolo[1,2-c]thiazole The title compound was prepared by the procedure described in Example 2 using the compound resulting from Example 38, 3-(pyridin-3-yl)- 7-[6-(4-methoxyphenyl)indol-3-yl]carbonyl-1H,3H-pyrrolo[1,2-c]thiazole, instead of 3-(pyridin-3-yl)-7-(indol-3-yl)carbonyl-1H,3H-pyrrolo[1,2-c]thiazole and using methylisocyanate instead of N,N-dimethylcarbamoyl chloride. m.p. 251° C. $^1$H NMR (DMSO-d6, 300 MHz) δ2.89 (d, 3H, J=5Hz), 3.81 (s, 3H), 4.51 (d, 1H, J=15Hz), 4.68 (dd, 1H, J=2, 15Hz), 6.78 (d, 1H, J=3Hz), 6.81 (d, 1H, J=1Hz), 7.03–7.08 (m, 3H), 7.45 (dd, 1H, J=5, 8Hz), 7.59 (dd, 1H, J=1, 9Hz), 7.61–7.71 (m, 3H), 8.28 (d, 1H, J=9Hz), 8.48–8.52 (m, 2H), 8.56–8.62 (m, 3H). MS (DCI/NH$_3$) m/e 509 (M+H)$^+$, 452. IR (KBr) 1705, 1605, 1530, 1515, 1475. Anal calcd for C$_{29}$H$_{24}$N$_4$O$_3$S: C, 68.49; H, 4.76; N, 11.02. Found: C, 67.56; H, 4.96; N, 10.58.

EXAMPLE 44

Preparation of 3-(1-Oxide-pyridin-3-yl)-7-(1-N,N-dimethylcarbamoylindol-3-ylcarbonyl)-1H,3H-pyrrolo[1,2-c]thiazole The title compound was prepared by the procedure described in Example 34 using the compound resulting from Example 2, 3-(pyridin-3-yl)-7-(1-N,N-dimethylcarbamoylindol-3-yl)carbonyl-1H,3H-pyrrolo[1,2-c]thiazole instead of 3-(pyridin-3-yl)-7-(1-N,N-dimethylcarbamoyl-6-phenylindol-3-yl)carbonyl- 1H,3H-pyrrolo[1,2-c]thiazole. $^1$H NMR (DMSO-d6, 300 MHz) δ3.05 (s, 6H), 4.46 (d, 1H, J=15Hz), 4.65 (dd, 1H, J=2, 15Hz), 6.70 (d, 1H, J=2Hz), 6.86 (d, 1H, J=3Hz), 6.91 (d, 1H, J=3Hz), 7.13 (d, 1H, J=8Hz), 7.28–7.47 (m, 3H) 7.62 (d, 1H, J=8Hz), 8.18–8.28 (m, 3H), 8.33 (s, 1H), IR (KBr) 2920, 1690, 1600, 1535, 1480.

EXAMPLE 45

Preparation of
3-(1-Oxide-pyridin-3-yl)-7-[1-N,N-dimethylcarbamoyl-6-(4-methoxyphenyl)indol-3-ylcarbonyl]-1H,3H-pyrrolo[1,2-c]thiazole The title compound was prepared by the procedure described in Example 34 using the compound resulting from Example 40, 3-(pyridin-3-yl)-7-[1-N,N-dimethylcarbamoyl-6-(4-methoxyphenyl)indol-3-ylcarbonyl]- 1H,3H-pyrrolo[1,2-c]thiazole instead of 3-(pyridin-3-yl)-7-(1-N,N-dimethylcarbamoyl- 6-phenylindol-3-yl)carbonyl-1H,3H-pyrrolo[1,2-c]thiazole. $^1$H NMR (DMSO-d6, 300 MHz) δ3.09 (s, 6H), 3.81 (s, 3H), 4.47 (d, 1H, J=15Hz), 4.67 (dd, 1H, J=2, 15Hz), 6.71 (d, 1H, J=1Hz), 6.87 (d, 1H, J=3Hz), 6.94 (d, 1H, J=8Hz), 7.40–7.46 (m, 1H), 7.59 (dd, 1H, J=2, 9Hz), 7.63–7.70 (m, 2H), 7.78 (d, 1H, J=1Hz), 8.19–8.22 (m, 2H), 8.29 (d, 1H, J=9Hz), 8.34 (s, 1H). MS (DCI/NH$_3$) m/e 523 (M+H)$^+$, 539.

EXAMPLE 46

Preparation of
3-(Pyridin-3-yl)-7-[1-(2-carbomethoxyethyl)-6-(4-fluorophenyl)indol-3-ylcarbonyl]-1H,3H-pyrrolo[1,2-c]thiazole Sodium hydride (95%, 37.4 mg, 1.48 mmol) was added to a solution of 3-(pyridin- 3-yl)-7-[6-(4-fluorophenyl)indol-3-ylcarbonyl]-1H,3H-pyrrolo[1,2-c]thiazole (0.50 g, 1.14 mmol), prepared according to the method of Example 28, in DMF (30 mL). The reaction mixture was stirred for 30 min. at ambient temperature, and then methyl acrylate (0.40 mL, 4.56 mmol) was added. The reaction mixture was poured into brine and extracted three times with ethyl acetate. The combined organic layers where dried over MgSO$_4$, filtered, and concentrated in vacuo. 3-(Pyridin-3-yl)-7-[1-( 2-carbomethoxyethyl)-6-(4-fluorophenyl)indol-3-ylcarbonyl]-1H,3H-pyrrolo[1,2-c]thiazole (190 mg, 32%) was obtained by flash chromatography on silica gel (5 g, 40%, then 60%, then 80% ethyl acetate, hexanes). $^1$H NMR (CDCl$_3$, 300 MHz) δ2.93 (t, 2H, J=6, 8Hz), 3.68 (s, 3H), 4.53 (dd, 3H, J=6, 11Hz), 4.7 (dd, 1H, J=2, 15Hz), 6.38 (d, 1H, J=3Hz), 6.43 (s, 1H), 6.78 (d, 1H, J=3Hz), 7.15 (t, 2H, J=9, 10Hz), 7.35 (dd, 1H, J=5, 8 Hz), 7.5 (dd, 2H, J=3, 10Hz), 7.6–7.1 (m, 3H), 7.95 (s, 1H), 8.45 (dd, 1H, J=1, 9Hz), 8.6–8.68 (m, 2H). MS (DCI/MH$_3$) m/e 526 (M+H)$^+$.

EXAMPLE 47

Preparation of
3-(Pyridin-3-yl)-7-(6-chloroindol-3-ylcarbonyl)-1H,3H-pyrrolo[1,2-c]thiazole The desired compound was prepared by the procedure of Example 28, using 6-chloroindole instead 6-phenylindole. m.p. 263°–265° C. $^1$H NMR (DMSO-d6, 300 MHz) δ4.45 (d, 1H, J=15Hz), 4.62 (dd, 1H, J=2, 15Hz), 6.70 (d, 1H, J=3Hz), 6.77 (s, 1H), 6.89 (d, 1H, J=3Hz), 7.20 (dd, 1H, J=2, 9Hz), 7.43 (dd, 1H, J=5, 7Hz), 7.52 (d, 1H, J=2Hz), 7.65 (dt, 1H, J=1, 8Hz), 8.25 (d, 1H, J=9Hz), 8.28 (d, 1H, J=2Hz), 8.53–8.58 (m, 2H), 11.98 (s, 1H). MS (DCI/NH$_3$) m/e 380

(M+H)+, 350. Anal calcd for $C_{20}H_{14}ClN_3OS$: C, 63.24; H, 3.71; N, 11.06. Found: C, 61.98; H, 2.89; N, 10.73.

EXAMPLE 48

Preparation of
3-(Pyridin-3-yl)-7-[1-N,N-dimethylcarbamoyl-6-(3,4,5-trimethoxyphenyl)indol-3-ylcarbonyl]-1H,3H-pyrrolo[1,2-c]thiazole The title compound was prepared by the method of Example 2, using 3-(pyridin- 3-yl)-7-[6-(3,4,5-trimethoxyphenyl)indol-3-ylcarbonyl]-1H,3H-pyrrolo-[ 1,2-c]thiazole, prepared according to the methods of Example 28, except using 3,4,5-trimethoxybromobenzene instead of 4-fluorobromobenzene instead of 3-(pyridin-3-yl)- 7-(indol-3-yl)carbonyl-1H,3H-pyrrolo[1,2-c]thiazole, m.p. 194°–196° C. $^1$H NMR (DMSO-d6, 300 MHz) δ3.09 (s, 6H), 3.71 (s, 3H), 3.89 (s, 6H), 4.50 (d, 1H, J=15Hz), 4.68 (dd, 1H, J=2, 15Hz), 6.74 (d, 1H, J=3Hz), 6.80 (s, 1H), 6.91–6.95 (m, 3H), 7.45 (dd, 1H, J=5, 8Hz), 7.62 (dd, 1H, J=1, 9Hz), 7.68 (dt, 1H, J=1, 9Hz), 7.82 (s, 1H), 8.30 (d, 1H, J=8Hz), 8.36 (s, 1H), 8.55–8.60 (m, 2H). MS (DCI/NH$_3$) m/e 583 (M+H)+, 461, 387. IR (KBr) 2940, 1690,1605, 1580, 1535. Anal calcd for $C_{32}H_{30}N_4O_5S$: C, 65.96; H, 5.19; N, 6.92. Found: C, 64.28; H, 4.06; N, 9.26.

EXAMPLE 49

Preparation of
3-(Pyridin-3-yl)-7-[1-(2-carboxyethyl)-6-(4-fluorophenyl)indol-3-ylcarbonyl]-1H,3H-pyrrolo[1,2-c]thiazole Step 1. Preparation of
3-(pyridin-3-yl)-7-[1-(2-carboethoxyethyl)-6-(4-fluorophenyl)indol-3-ylcarbonyl]-1-1H,3H-pyrrolo[1,2-c]thiazole The desired compound was prepared according to the method of Example 46, except substituting ethyl acrylate for methyl acrylate.

Step 2. Preparation of
3-(Pyridin-3-yl)-7-[1-(2-carboxyethyl)-6-(4-fluorophenyl)indol-3-ylcarbonyl]-1H,3H-pyrrolo[1,2-c]thiazole A mixture of 3-(pyridin-3-yl)-7-[1-(2-carboethoxyethyl)-6-(4-fluorophenyl)indol-3-ylcarbonyl]-1H,3H--pyrrolo[1,2-c]thiazole (90 mg, 0.17 mmol), and lithium hydroxide (11 mg), where stirred in 33% aqueous THF (15 mL) for 45 min. The reaction mixture was diluted with H$_2$O and taken to pH 4 with 1M aqueous HCl. The reaction mixture was extracted three times with ethyl acetate. The combined organic layers where dried over MgSO$_4$, filtered,and concentrated in vacuo. 3-(Pyridin-3-yl)-7-[1-(2-carboxyethyl)-6-(4-fluorophenyl)indol-3-ylcarbonyl]- 1H,3H-pyrrolo[1,2-c]thiazole (63 mg), was crystallized from ethyl acetate, hexanes. $^1$H NMR (CDCl$_3$, 300MHz) δ2.95 (t, 2H, J=6, 7Hz), 4.5–4.65 (m, 4H), 6.14 (d, 1H, J=3Hz), 6.45 (s, 1H), 6.73 (d, 1H, J=3Hz), 7.15 (t, 2H, J=9, 11Hz), 7.38–7.43 (m, 1H), 7.52 (d, 2H, J=8Hz), 7.6–7.7 (m, 3H), 8.05 (s, 1H), 8.46 (d, 1H, J=9Hz), 8.57 (bs, 2H), MS (DCI/NH$_3$) m/e 512 (M+H)+. Anal calcd for $C_{29}H_{22}N_3O_3SF$; C, 68.09; H, 4.33; N, 8.21. Found: C, 67.78; H, 3.90; N, 8.06.

EXAMPLE 50

Preparation of
3-(Pyridin-3-yl)-7-[1-(2-sulfamylethyl)-6-(4-fluorophenyl)indol-3-ylcarbonyl]-1H,3H-pyrrolo[1,2-c]thiazole The title compound was prepared by the procedure described in Example 46 using vinylsulfonamide instead of methyl acrylate. $^1$H NMR (DMSO-d6, 300 MHz) δ 3.6 (t, 2H, J=7, 9Hz), 4.48 (d, 1H, J=15Hz), 4.65 (d, 1H, J=15Hz), 4.77 (t, 2H, J=6, 8Hz), 6.73 (d, 1H, J=3Hz), 6.78 (s, 1H), 6.95 (d, 1H, J=3Hz), 7.13 (s, 2H), 7.33 (t, 2H, J=9, 10Hz), 7.45 (dd, 1H, J=5, 9Hz), 7.54 (d, 1H, J=9Hz), 7.67 (d, 1H, J=8Hz), 7.8–7.88 (m, 3H), 8.32 (d, 1H, J=9Hz), 8.39 (s, 1H), 8.55–8.6 (m, 2H). MS (DCI/NH$_3$) m/e 547 (M+H)+. Anal calcd for $C_{28}H_{23}N_4O_3S_2F$: C, 61.52; H, 4.24; N, 10.25. Found: C, 60.82; H, 3.95; N, 9.95.

EXAMPLE 51

Preparation of
3-(Pyridin-3-yl)-7-[1-methanesulfonyl-6-(4-fluorophenyl)indol-3-ylcarbonyl]-1H,3H-pyrrolo[1,2-c]thiazole The desired compound was prepared according to the method of Example 29, except substituting methanesulfonyl chloride for N,N-dimethylcarbamoyl chloride. $^1$H NMR (DMSO-d6) δ3.76 (s, 3H), 4.48 (d, 1H, J=15Hz), 4.66 (dd, 1H, J=15, 1.5Hz), 6.78 (d, 1H, J=3Hz), 6.82 (bs, 1H), 6.9 (d, 1H, J=3Hz), 7.35 (t, 2H, J= 9Hz), 7.45 (dd, 1H, J=4.5, 6Hz), 7.65–7.74 (cm 2H), 7.82 (dd, 2H, J=6, 3Hz), 8.08 (bs, 1H), 8.2 (s, 1H), 8.3 (d, 1H, J=9Hz), 8.55–9.0 (cm, 2H), MS (DCI/NH$_3$) m/e 517 (M+H)+440. Anal calcd for $C_{27}H_{20}FN_3O_3S_2 \cdot 0.75H2O$: C, 51.06; H, 4.08; N, 7.91. Found; C, 51.14; H, 3.69; N, 7.62.

EXAMPLE 52

Preparation of
3-(Pyridin-3-yl)-7-(1-N,N-dimethylcarbamoyl-6-phenylindol-3-ylcarbonyl)-1H,3H-pyrrolo[1,2-c]thiazole Hydrochloride A solution of 3-(pyridin-3-yl)-7-(1-N,N-dimethylcarbamoyl-6-phenylindol-3-yl)carbonyl- 1H,3H-pyrrolo[1,2-c]thiazole, prepared as in Example 12, was treated at ambient temperature with excess 4N HCl in dioxane. After stirring for two hours, 3-(Pyridin-3-yl)-7-(1-N,N-dimethylcarbamoyl-6-phenylindol-3-ylcarbonyl)- 1H,3H-pyrrolo[1,2-c]thiazole Hydrochloride was isolated by filtration. $^1$H NMR (CD$_3$OD, 300 MHz) δ3.17 (s, 6H), 4.55 (d, 1H, J=15.0Hz), 4.72 (dd, 1H, J= 15.0, 1.0Hz), 6.72 (d, 1H, J=3.0Hz), 6.89 (d, 1H, J=1.0Hz), 6.98 (d, 1H, J= 3.0Hz), 7.36 (t, 1H, J=7.5Hz), 7.46 (t, 2H, J=7.5Hz), 7.61 (dd, 1H, J=9.0, 1.0Hz), 7.69 (d, 2H, J=8.0Hz), 7.81 (bs, 1H), 8.09 (dd, 1H, J=9.0, 6.0Hz), 8.24 (s, 1H), 8.31 (d, 1H, J=9.0Hz), 8.49 (dt, 1H, J=8.5, 1.0Hz), 8.84 (bs, 1H), 8.85 (m, 1H), IR (KBr) 3450, 1695, 1540, 1390. Anal calcd for $C_{29}H_{25}ClN4O_2S$: C, 65.84; H, 4.76; N, 10.59. Found: C, 65.96; H, 4.91; N, 10.48.

EXAMPLE 53

Preparation of 3-(Pyridin-3-yl)-7-[1-(2-N,N-dimethylcarbamoylmethyl)-6-(4-fluorophenyl)indol-3-ylcarbonyl]-1H,3H-pyrrolo[1,2-c]thiazole The desired compound was prepared according to the method of Example 46, except substituting N,N dimethylchloroacetamide for methyl acrylate. $^1$H NMR (DMSO-d6, 300 MHz) δ2.88 (s, 3H), 3.15 (s, 3H), 4.48 (d, 1H, J=15 Hz), 4.65 (dd, 1H, J=15, 2 Hz), 5.37 (s, 2H), 6.72 (d, 1H, J=3 Hz), 6.78 (bs, 1H), 6.85 (d, 1H, J=3 Hz), 7.31 (t, 2H, J=12 Hz), 7.44 (cm, 2H), 7.52 (dd, 2H, J=12, 2Hz), 7.66 (cm, 1H), 7.78 (cm, 3H), 8.25 (s, 1H), 8.32 (d, 1H, J=12 Hz), 8.57 (cm, 2H), MS (DCI/NH$_3$) m/e 525 (M+H)$^+$, 542 (M+NH$_4$)$^+$. IR (KBr) 1600(s), 1660(s). Anal calcd for C$_{30}$H$_{25}$N$_4$O$_2$SF: C, 68.69; H, 4.80; N, 10.68. Found: C. 68.20; H, 4.63; N, 10.68.

EXAMPLE 54

Preparation of 3-(1-Oxide-pyridin-3-yl)-7-(1-N,N-dimethylcarbamoyl-6-phenylindol-3-ylcarbonyl)-1H,3H-pyrrolo[1,2-c]thiazole hydrochloride The title compound was prepared by the procedure described in Example 52 using the compound resulting from Example 34, 3-(1-oxide-pyridin-3-yl)-7-(1-N,N-dimethylcarbamoyl- 6-phenylindol-3-ylcarbonyl)-1H,3H-pyrrolo[1,2-c]thiazole instead of 3-(pyridin-3-yl)-7-(1-N,N-dimethylcarbamoyl-6-phenylinol-3-ylcarbonyl)- 1H,3H-pyrrolo[1,2-c]thiazole. m.p. 122°–130° C. 1H NMR (CD$_3$OD, 300 MHz) δ 3.16 (s, 6H), 4.53 (d, 1H, J=15.0Hz), 4.69 (d, 1H, J=15.0Hz), 6.73 (s, 1H, J= 3.0Hz), 6.74 (bs, 1H), 6.97 (d, 1H, J=3.0Hz), 7.33 (t, 1H, J=7.5Hz), 7.45 (t, 2H, J=7.5Hz), 7.62 (dd, 1H, J=9.0, 1.0Hz), 7.68 (d, 2H, J=7.5Hz), 7.81 (m, 2H), 8.23 (s, 1H), 8.31 (d, 1H, J=9.0Hz), 8.58(bs, 1H), 8.60 (m, 1H), IR (KBr) 3410, 1695, 1535, 1395.

EXAMPLE 55

Preparation of 3-(Pyridin-3-yl)-7-[1-N,N-dimethylsulfamyl-6-(4-fluorophenyl)indol-3-ylcarbonyl]-1H,3H-pyrrolo[1,2-c]thiazole The title compound was prepared by the procedure described in Example 51, using N,N-dimethylaminosulfonylchloride instead of methanesulfonylchloride, m.p. 100° C. $^1$H NMR (DMSO-d6, 300 MHz) δ3.35 (s, 6H), 4.48 (d, 1H, J=15Hz), 4.67 (d, 1H, J=15Hz), 6.75–6.77 (m, 1H), 6.82 (d, 2H, J=3Hz), 7.35 (t, 2H, J=9Hz), 7.42–7.46 (dd, 1H, J=4.5,J=3Hz), 7.65–7.73 (cm, 2H), 7.75 (dd, 2H, J=6, 3Hz), 8.08 (m, 1H), 8.22 (s, 1H), 8.3 (d, 1H, J=9Hz), 8.58 (m, 2H). MS (FAB) m/e 546 (M+1), 563. Anal calcd for C$_{28}$H$_{23}$FN$_4$O$_3$S$_2$·0.75H$_2$O: C, 60.04; H, 4.41; N, 10.00. Found: C, 60.84; H, 4.75; N, 9.66.

EXAMPLE 56

Preparation of 3-(Pyridin-3-yl)-7-[1-N,N-dimethylcarbamoyl-6-[3-aminophenyl)indol-3-ylcarbonyl]-1H,3H-pyrrolo[1,2-c]thiazole To a solution of 3-(pyridin-3-yl)-7-(6-bromoindol-3-ylcarbonyl)- 1H,3H-pyrrolo[1,2-c]thiazole (370 mg, 0.75 mmol), prepared as in Example 64, in DME (15 mL), was added a solution of 3-aminophenylboronic acid (182 mg, 1.2 mmol). The reaction mixture was warmed to reflux, diluted with DME (15 mL), and stirred at reflux for 17 hours. The reaction mixture was cooled to ambient temperature and partitioned between saturated aqueous NaHCO$_3$ and ethyl acetate. The aqueous phase was extracted twice with ethyl acetate, then once with 3% methanol, methylene chloride. The combined organic layers where dried over MgSO$_4$, filtered, and concentrated in vacuo. Purification by chromatography on silica gel (3% methanol, methylene chloride) gave 3-(pyridin-3-yl)-7-(1-N,N-dimethylcarbamoyl-6-(3-aminophenyl)indol- 3-ylcarbonyl)-1H,3H-pyrrolo[1,2-c]thiazole as a pale-yellow foam. m.p. 86°–88° C. $^1$H NMR (DMSO-d6, 300 MHz) δ8.57 (m, 2H), 8.28 (d, 1H, J= 8.1Hz), 7.77 (m, 1H), 7.68 (m, 1H), 7.60 (m, 6H), 7.56 (m, 1H), 6.91 (d, 1H, J= 3.0Hz), 6.79 (bds, 1H), 6.73 (d, 1H, J=3.3 Hz), 5.19 (bds, 2H), 4.67 (dd, 1H, J= 2.2, 14.7Hz), 4.49 (d, 1H, J=14.7Hz), 3.08 (s, 6H). MS (DCI/NH$_3$) m/e 508 (M+H)$^+$ (75), 182 (100). Anal calcd for C$_{29}$H$_{25}$N$_5$O$_2$S: C, 68.62; H, 4.96; N, 13.80. Found: C, 67.20; H, 4.88; N, 11.08.

EXAMPLE 57

Preparation of 3-(Pyridin-3-yl)-7-[1-(2-tert-butoxycarbonylaminoethyl-6l(4-fluorophenyl)indol-3-ylcarbonyl]-1H,3H-pyrrolo[1,2-c]thiazole Step 1. N-tert-butoxycarbonylazide The desired compound was prepared according to the method of Example 9, except substituting aziridine for 3(Pyridin-3-yl)-7-(indol-3-yl)carbonyl-1H,3H-pyrrolo[1,2-c]thiazole Step 2. 3-(Pyridin-3-yl)-7-[1-(2-tert-butoxycarbonylaminoethyl)-6-(4-fluorophenyl)indol-3-ylcarbonyl]-1H,3H-pyrrolo[1,2-c]thiazole The desired compound was prepared according to the method of Example 46, except substituting N-tert-butoxycarbonylaziridine, prepared in step 1for methyl acrylate. $^1$H NMR (CDCl$_3$, 300 MHz) δ1.5–1.7 (bs, 2H), 3.25 (t, 2H, J=6, 8Hz), 4.3 (t, 2H, J=6, 7Hz), 4.56 (d, 1H, J=15Hz), 4.70 (dd, 1H, J=15, 3Hz), 6.35 (d, 1H, J=3Hz), 6.42 (s, 1H), 6.78 (d, 1H, J=3Hz), 7.15 (t, 2H, J=9, 12Hz), 7.35 (dd, 1h, J=5, 9Hz), 7.5 (m, 2H), 7.62 (dd, 3H, J=7. 9Hz), 7.93 (s, 1H), 8.45 (d, 1H, J=9Hz), 8.6 (d, 1H, J=3Hz) 8.65 (dd, 1H, J=3, 5Hz). MS (DCI/NH$_3$) m/e 483 (M+H)$^+$. Anal calcd for C$_{28}$H$_{23}$N$_4$OSF: C, 69.69; H, 4.80; N, 11.61. Found: C, 69.41; H, 4.55; N, 11.46.

EXAMPLE 58

Preparation of 3-(1-Oxide-pyridin-3-yl)-7-(1-methyl-6-phenylmethoxyindol-3-ylcarbonyl)-1H,3H-pyrrolo[1,2-c]thiazole The title compound was prepared by the procedure described in Example 34 using the compound resulting from Example 21, 3-(pyridin-3-yl)-7-(1-methyl- 6-phenylmethoxyindol-3-ylcarbonyl)-1H,3H-pyrrolo[1,2-c]thiazole instead of 3-(pyridin-3-yl)-7-(1-N,N-dimethylcarbamoyl-6-phenylindol-3-yl)carbonyl- 1H,3H-pyrrolo[1,2-c]thiazole. m.p. 98°–100° C. $^1$H NMR (DMSO-d6, 300 MHz) δ 8.22 (m, 1H), 8.18 (bds, 1H), 8.16 (m, 1H), 8.13 (s, 1H), 7.51 (m, 2H), 7.41 (m, 3H), 7.36 (m, 1H), 7.20 (d, 1H, J=2Hz), 7.12 (bdd, 1H, J=7.2 Hz), 6.94 (dd, 1H, J=2.8, 6.9Hz), 6.92 (d, 1H, J=3.0Hz), 6.92 (d, 1H, J=3.0 Hz), 6.67 (bds, 1H), 5.18 (s, 2H), 4.62 (bdd, 1H, J=15.1Hz), 4.43 (d, 1H, J=15.1Hz), 3.85 (s, 3H), MS (DCI/NH$_3$) m/e 499(M+NH4)$^+$ (30), 482(M+H)$^+$ (50), 466 (100).

EXAMPLE 59

Preparation of 3-(Pyridin-3-yl)-7-[1-(2-aminoethyl)-6-(4-fluorophenyl) indol- 3-ylcarbonyl]-1H,3H-pyrrolo[1,2-c]thiazole A solution of 3-(pyridin-3-yl)-7-[1-(2-tert-butoxycarbonylaminoethyl)- 6-(4-fluorophenyl)indol-3-ylcarbonyl]-1H, 3H-pyrrolo[1,2-c]thiazole (104 mg), prepared as in Example 57, in $CH_2Cl_2$ at 0° C. was treated with 4N HCl/dioxane (1 mL). The reaction mixture was stirred for 15 min at 0° C. and then concentrated in vacuo. The resulting solid was azeotroped three times with $CH_2Cl_2$ to give 3-(Pyridin-3-yl)-7-[1-( 2-aminoethyl)-6-(4-fluorophenyl)indol-3-ylcarbonyl]-1H,3H-pyrrolo[1,2-c]thiazole hydrochloride (115 mg), $^1$H NMR ($D_3$COD, 300 MHz) δ3.48–3.60 (m, 3H), 3.64– 3.75 (m, 4H), 4.53 (d, 1H, J=15Hz) 4.68–4.77 (m, 3H), 6.76 (d, 1H, J=3Hz), 6.9 (d, 1H, J=1.5Hz), 7.55 (dd, 1H, J=1.5 9Hz), 7.75 (dd, 2H, J=6, 8Hz), 7.83 (s, 1H), 8.13 (dd, 1H, J=6, 8Hz), 8.30 (s, 1H), 8.35 (d, 1H, J=9Hz), 8.49 (d, 1H, J=9Hz), 8.87 (d, 2H, J=7Hz), MS (DCI/$NH_3$) m/e 483 $(M+H)^+$.

EXAMPLE 60

Preparation of 3-(1-Oxide-pyridin-3-yl)-7-[1-N,N-dimethylsulfamyl-6-(4-fluorophenyl)indol-3-ylcarbonyl]-1H,3H-pyrrolo[1,2-c]thiazole The title compound was prepared by the procedure described in Example 34 using the compound resulting from Example 55, 3-(pyridin-3-yl)-7-[1-N,N-dimethylsulfamyl-6-(4-fluorophenyl)indol-3-ylcarbonyl]-1H,3H-pyrrolo[1,2-c]thiazole instead of 3-(pyridin-3-yl)-7-(1-N,N-dimethylcarbamoyl-6-phenylindol-3-yl)carbonyl- 1H,3H-pyrrolo[1,2-c]triazole. m.p. 118° C. $^1$H NMR ($CDCl_3$, 300 MHz) δ2.95 (s,6H), 4.57 (d, 1H, J=15Hz), 4.67 (dd, 1H, J=12, 3Hz), 6.34 (s, 1H), 6.48 (d, J=6Hz), 7.58–7.64 (cm, 3H), 8.11 (d, 2H, J=4.5Hz), 8.19 (d, 1H, J=6Hz), 8.37 (d, 1H, J=9Hz), MS (DCI/$NH_3$) m/e 562 $(M+H)^+$, 547.

EXAMPLE 61

Preparation of 3-(Pyridin-3-yl)-7-[1-phenylsulfonyl-6-(4-fluorophenyl)indol-3-ylcarbonyl]-1H,3H-pyrrolo[1,2-c]thiazole The title compound was prepared by the procedure by the procedure described in Example 51, using phenylsulfonylchloride instead of methane sulfonyl chloride. m.p. 115°–116° C. $^1$H NMR ($CDCl_3$, 300 MHz) δ4.55 (d, 1H, J=12Hz), 4.67 (dd, 1H, J=12, 1.5Hz), 6.42 (d, 1H, J=3Hz), 6.46 (s, 1H), 7.13–7.2 (cm, 1H), 7.25 (s, 1H), 7.38 (dd, 1H, J=4.5, 0.75Hz), 8.14 (s, 1H), 8.2 (m, 1H), 8.28 (d, 1H, J=9Hz), 8.62 (s, 1H), 8.66 (d, 1H, J=3Hz), MS (FAB) m/e 508 $(M+H)^+$, 307. Anal calcd for $C_{32}H_{22}FN_3O_3S_2 \cdot 0.25H_2O$: C, 65.79; H, 3.88; N, 7.19. Found: C, 65.68; H, 3.93; N, 6.81.

EXAMPLE 62

Preparation of 3-(Pyridin-3-yl)-7-[1-N-(2-hydroxyethyl)carbamoyl-6-(4-fluorophenyl)indol-3-ylcarbonyl]-1H,3H-pyrrolo[1,2-c]thiazole The desired compound was prepared according to the method of Example 37 except substituting 3-(pyridin-3-yl)-7-[6-(4-fluorophenyl)indol-3-ylcarbonyl]- 1H,3H-pyrrolo[1,2-c]thiazole, prepared as in Example 28, for 3-(Pyridin-3-yl)-7-( 6-phenylmethoxyindol-3-yl)carbonyl-1H,3H-pyrrolo[1,2-c]thiazole, and substituting ethanolamine for amounts. $^1$H NMR (DMSO-d6, 300 MHz) δ3.32–3.42 (m, 2H), 3.60 (q, 2H, J=6Hz), 4.51 (d, 1H, J=15Hz), 4.68 (dd, 1H, J=2, 15Hz), 4.88 (t, 1H, J=6Hz), 6.79 (d, 1H, J=3Hz), 6.81 (d, 1H, J=1Hz), 7.09 (d, 1H, J=3Hz,) 7.32 (t, 2H, J=9Hz), 7.45 (dd, 1H, J=5, 8Hz), 7.61 (dd, 1H, J=1, 8Hz), 7.69 (dt, 1H, J=1, 8Hz), 7.71–7.76 (m, 2H), 8.32 (d, 1H, J=8Hz), 8.51 (d, 1H, J=1Hz). 8.56–8.61 (m, 3H), 8.47 (t, 1H, J=6Hz). MS (FAB) m/e 527 $(M+H)^+$, 440. IR (KBr) 1701, 1601, 1530, 1510, 1475, Anal calcd for $C_{29}H_{23}FN_4O_3S$: C, 66.15; H, 4.40; N, 10.64. Found: C, 64.93; H, 4.14; N, 10.00.

EXAMPLE 63

Preparation of 3-(Pyridin-3-yl)-7-(6-bromoindol-3-ylcarbonyl)-1H,3H-pyrrolo[1,2-c]thiazole The title compound was prepared by the procedure described in Example 1, using 6-bromoindole instead of indole, m.p. 265° C. $^1$H NMR (DMSO-d6, 300 MHz) δ4.45 (d, 1H, J=15Hz), 4.52 (dd, 1H, J=1, 15Hz), 6.70 (d, 1H, J=3Hz), 6.77 (s, 1H), 6.89 (d, 1H, J=3Hz), 7.31 (dd, 1H, J=1, 9Hz), 7.43 (dd, 1H, J=5, 8Hz), 7.61– 7.69 (m, 2H), 8.20 (d, 1H, J=9Hz), 8.27 (d, 1H, J=3Hz), 8.53–8.59 (m, 2H), 11.98 (s, 1H), MS (DCI/$NH_3$) m/e 443 $(M+NH4)+$, 441 $(M+NH4)^+$, 426 $(M+H)^+$, 424 $(M+H)^+$, 394, IR (KBr) 1582, 1560, 1530, 1510, 1480. Anal calcd for $C_{20}H_{14}BrN_3OS$: C, 56.61; H, 3.33; N, 9.90. Found: C, 55.82; H, 3.25; N, 9.54.

EXAMPLE 64

Preparation of 3-(Pyridin-3-yl)-7-(1-N,N-dimethylcarbamoyl-6-bromoindol-3-ylcarbonyl)-1H,3H-pyrrolo[1,2-c]thiazole The title compound was prepared by the procedure described in Example 2 using the compound resulting from Example 63, 3-(pyridin-3-yl)-7-(6-bromoindol- 3-ylcarbonyl)-1H,3H-pyrrolo[1,2-c]thiazole, instead of 3-(pyridin-3-yl)- 7-(indol-3-yl)carbonyl- 1H,3H-pyrrolo[1,2-c]thiazole and using methylisocyanate instead of N,N-dimethylcarbamoyl chloride. m.p. 199°–201° C. $^1$H NMR (DMSO-d6, 300 MHz) δ 3.05 (s, 6H), 4.48 (d, 1H, J=15Hz), 4.55 (dd, 1H, J=2, 15Hz), 6.73 (d, 1H, J=3Hz), 6.79 (d, 1H, J=1Hz), 6.90 (d, 1H, J=3Hz), 7.40–7.50 (m, 2H), 7.68 (dt, 1H, J=2, 8Hz), 7.82 (d, 1H, J=1Hz), 8.19 (d, 1H, J=9Hz), 8.37 (s, 1H), 8.55–8.59 (m, 2H). MS (DCI/$NH_3$) m/e 497 $(M+H)^+$, 495 $(M+H)^+$. IR (KBr) 3100, 2920, 1680, 1590, 1530. Anal calcd for $C_{23}H_{19}BrN_4O_2S$: C, 55.76; H, 3.87; N, 11.31. Found: C, 55.63; H, 3.59; N, 11.06.

EXAMPLE 65

Preparation of 3-(Pyridin-3-yl)-7-(1-N,N-dimethylcarbamoyl-6-chloroindol-3-ylcarbonyl)-1H,3H-pyrrolo[1,2-c]thiazole The title compound was prepared by the procedure described in Example 2 using the compound resulting from Example 47, 3-(pyridin-3-yl)-7-(6-chloroindol- 3-ylcarbonyl)-1H,3H-pyrrolo[1,2-c]thiazole, instead of 3-(pyridin-3-yl)- 7-(indol-3-yl)carbonyl-1H,3H-pyrrolo[1,2-c]thiazole and using methylisocyanate instead of N,N-dimethylcarbamoyl chloride, m.p. 214°–215° C. $^1$H NMR (DMSO-d6, 300 MHz) δ 3.05 (s, 6H), 4.48 (d, 1H), J=15Hz), 4.56 (dd, 1H, J=2, 15Hz), 6.73 (d, 1H, J=3Hz), 6.79 (d, 1H, J=1Hz), 6.90 (d, 1H, J=3Hz), 7.36 (dd, 1H, J=2, 8Hz), 7.43 (dd, 1H, J=5, 8Hz), 7.65–7.70 (m, 2H), 8.24 (d, 1H, J=9Hz), 8.38 (s, 1H), 8.55– 8.59 (m, 2H). MS (DCl/NH$_3$) m/e 451 (M+H)$^+$, 329, 141, 124. Anal calcd for $C_{23}H_{19}ClN_4O_2S$: C, 61.26; H, 4.25; N, 12.42. Found: C, 60.99; H, 4.16; N, 12.13.

EXAMPLE 66

Preparation of 3-(1-Oxide-Pyridin-3-yl)-7-(1-N,N-dimethylcarbamoyl-6-chloroindol-3-ylcarbonyl)-1H,3H-pyrrolo[1,2-c]thiazole The title compound was prepared by the procedure described in Example 34 using the compound resulting from Example 65, 3-(pyridin-3-yl)-7-( 1-N,N-dimethylcarbamoyl-6-chloroindol-3-ylcarbonyl)-1H,3H-pyrrolo[1,2-c]thiazole instead of 3-(pyridin-3-yl)-7-(1-N,N-dimethylcarbamoyl-6-phenylindol-3-yl)carbonyl- 1H,3H-pyrrolo[1,2-c]thiazole m.p. 192°–194° C. $^1$H NMR (DMSO-d6, 300 MHz) δ3.06 (s, 6H), 4.45 (d, 1H, J=2, 15Hz), 4.55 (dd, 1H, J=2, 15Hz), 6.70 (d, 1H, J=1Hz), 6.87 (d, 1H, J=3Hz), 6.92 (d, 1H, J=3Hz), 7.14 (d, 1H, J=8Hz), 7.36 (dd, 1H, J=2, 9Hz), 7.39–7.45 (m, 1H), 7.69 (d, 1H, J=2Hz), 8.18–8.27 (m, 3H), 8.40 (s, 1H), MS (DCl/NH$_3$) m/e 484 (M=NH4)$^+$, 467 (M+H)$^+$, 451. anal calcd for $C_{23}H_{19}ClN_4O_3S$: C, 59.16; H, 4.10; N, 12.00. Found: C, 57.61; H, 3.96; N, 11.53.

EXAMPLE 67

Preparation of 3-(1-Amino-pyridin-3-yl)-7-[1-N,N-dimethylcarbamoyl-6-(4-fluorophenyl)indol-3-ylcarbonyl]-1H,3H-pyrrolo[1,2-c]thiazole The desired compound was prepared according to the method of Example 34, except substituting 3-(Pyridin-3-yl)-7-[1-N,N-dimethylcarbamoyl- 6-(4-fluorophenyl)indol-3-ylcarbonyl]-1H,3H-pyrrolo[1,2-c]thiazole, prepared as in Example 29, for 3-(pyridin-3-yl)-7-(1-N,N-dimethylcarbamoyl-6-phenylindol- 3-yl)carbonyl-1H,3H-pyrrolo[1,2-c]thiazole, and aqueous hydrazine for aqueous hydroxylamine, m.p. 253°–258° C. $^1$H NMR (CD$_3$OD, 300 MHz) δ2.36(s, 3H), 3.17 (s, 6H), 4.55(d, 1H, J=15.0Hz), 4.71 (d, 1H, J=15.0, 1.0Hz), 6.78 (d, 1H, J= 3.0Hz), 6.82 (d, 1H, J=1.0Hz), 6.98 (d, 1H, J=3.0Hz), 7.20 (t, 2H, J=7.5Hz), 7.22 (d, 2H, J=8.5Hz), 7.58 (dd, 1H, J=9.0, 1.0Hz), 7.69 (d, 2H, J=8.5Hz), 7.71 (m, 2H), 7.79 (bs, 1H), 7.99 (dd, 1H, J=7.5, 6.0Hz), 8.17 (d, 1H, J=8.5Hz), 8.25 (s, 1H), 8.31 (d, 1H, J=9.0Hz), 8.66 (bs, 1H), 8.71 (bd, 1H, J=6.0 Hz). MS (FAB) m/e 526 (M+1)$^+$. IR (KBr) 3410, 1695, 1610, 1210. Anal calcd for $C_{29}H_{25}FN_5O_2S$; C, 61.18; H, 4.71; N, 9.91. Found: C, 61.19; H, 4.72; N, 9.95.

EXAMPLE 68

Preparation of 3-(Pyridin-3-yl)-7-[1-(2-methanesulfonylaminoethyl)-6-(4-fluorophenyl)indol-3-ylcarbonyl]-1H,3H-pyrrolo[1,2-c]thiazole To a solution of 3-(pyridin-3-yl)-7-[1-(2-aminoethyl)-6-(4-fluorophenyl)indol- 3-ylcarbonyl]-1H,3H-pyrrolo[1,2-c]thiazole (0.20 g, 0.062 mmol), prepared according to the method of Example 59, and triethylamine (13 μL, 0.093 mmol) in THF (15 mL) was added methanesulfonyl chloride (6 μL, 0.074 mmol). The reaction mixture was stirred for two hours at ambient temperature. The reaction mixture was quenched with saturated aqueous NH$_4$Cl and extracted with ethyl acetate. The organic phase was washed with brine, dried over MgSO$_4$, filtered, and concentrated in vacuo. 3-(Pyridin- 3-yl)-7-[1-(2-methanesulfonylaminoethyl)-6-(4-fluorophenyl)indol-3-ylcarbonyl]- 1H,3H-pyrrolo[1,2-c]thiazole (66 mg) was obtained by flash chromatography on silica gel (98:2 CHCl3, methanol), $^1$H NMR (CDCl$_3$, 300 MHz) δ2.83 (s, 3H), 3.6 (d, 2H, J=6Hz), 4.42–4.52 (m, 3H), 4.65 (d, 1H, J=15Hz), 5.57 (bs, 1H), 6.38 (bs, 1H), 6.46 (bs, 1H), 6.8 (d, 1H, J=3Hz), 7.15 (t, 2H, J=9Hz, 11Hz), 7.47 (d, 2H, J=7Hz), 7.52 7.65 (m, 3H), 7.8 (d, 1H, J=9Hz), 7.95 (s, 1H), 8.38 (d, 1H, 9Hz), 8.55 (bs, 2H). MS (DCl/NH$_3$) m/e 561 (M+H)$^+$. Anal calcd for $C_{29}H_{25}FN_4O_3S_2$: C, 62.13; H, 4.49; N, 9.99. Found: C, 61.37; H, 4.57; N, 9.58.

EXAMPLE 69

Preparation of 3-(Pyridin-3-yl)-7-[1-hydrazinocarbonyl-6-(4-fluorophenyl)indol-3-ylcarbonyl]-1H,3H-pyrrolo[1,2-c]thiazole The title compound was prepared by the procedure described in Example 62 using hydrazine instead of ethanolamine. $^1$H NMR (DMSO-d6, 300 MHz) δ4.50 (d, 1H, J=15Hz), 4.60 (bs, 2H), 4.68 (dd, 1H, J=2, 15Hz), 6.78 (d, 1H, J=3Hz), 6.81 (d, 1H, J=1Hz), 7.09 (s, 1H), 7.33 (t, 2H, J=9Hz), 7.45 (dd, 1H, J=5. 8Hz), 7.61 (dd, 1H, J=1, 9Hz), 7.65–7.76 (m, 3H), 8.31 (d, 1H, J=9Hz), 8.47–8.51- (m, 2H), 8.56 8.60 (m, 2H), 9.90 (bs, 1H), MS (DCl/NH$_3$) m/e 498 (M+H)$^+$, 440. Anal calcd for $C_{27}H_{20}FN_5O_2S$: C, 65.18; H, 4.05; N, 14.08. Found: C, 64.18; H, 4.03; N, 13.79.

EXAMPLE 70

Preparation of 3-(Pyridin-3-yl)-7-[1-(2-aminoethyl)-6-(4-fluorophenyl)indol-3-ylcarbonyl]-1H,3H-pyrrolo[1,2-c]thiazole Hydrochloride The title compound was prepared by the procedure described in Example 52 using the compound resulting from Example 59, 3-(pyridin-3-yl)-7-[1-(2-aminoethyl)- 6-(4-fluorophenyl)indol-3-ylcarbonyl]-1H,3H-pyrrolo[1,2-c] thiazole instead of 3-(pyridin-3-yl)-7-(1-N,N-dimethylcarbamoyl-6-phenylindol-3-ylcarbonyl)- 1H,3H-pyrrolo[1,2-c] thiazole. $^1$H NMR (CDCl3, 300 MHz,) δ1.35 (s, 9H), 3.57 (q, 2H, J=15Hz), 4.35–4.45 (m, 2H), 4.57 (d, 1H, J=15Hz), 4.63 (m, 1H), 4.7 (dd, 1H, J=3Hz), 7.15 (t, 2H, J=9Hz), 11Hz), 7.35 (dd, 1H, J=6, 11Hz), 7.5 (m, 2H), 7.6– 7.7 (m, 3H), 7.83 (s, 1H), 8.45 (d, 1H, J=9Hz), 8.60 (d, 1H, J=2Hz), 8.65 (d, 1H, J=5Hz), MS (DCl/NH$_3$) m/e 583 (M+H)$^+$.

EXAMPLE 71

Preparation of 3-(Pyridin-3-yl)-7-[1-ethanesulfonyl-6-[4-fluorophenyl)indol-3-ylcarbonyl]-1H,3H-pyrrolo[1,2-c]thiazole The title compound was prepared by the procedure described in Example 51, using ethanesulfonylchloride instead of methanesulfonylchloride, m.p. 132° C. $^1$H NMR (CDCl$_3$, 300 MHz) δ1.25 (cm, 2H), 3.4–3.52 (m, 3H), 4.57 (d, 1H, J=13.5Hz), 4.7 (dd, 1H, J=1.5, 13.5Hz), 6.42 (d, 1H, J=3Hz), 6.52 (bs, 1H), 6.8 (m, 1H), 7.16 (t, 2H, J=6Hz), 7.55–7.68 (cm, 5H), 7.8 (d, 1H, J=4.5Hz), 8.05–8.12 (m, 2H), 8.4 (d, 1H, J=7.5), 8.68 (bs, 1H). MS (DCI/NH$_3$) m/e 532 (M+H)$^+$, 440, 534. Anal calcd for C$_{28}$H$_{22}$N$_3$FO$_3$S$_2$.1H$_2$O: C, 61.19; H, 4.40; N, 7.65. Found: C 61.37; H, 4.40; N, 6.47.

EXAMPLE 72

Preparation of
3-(Pyridin-3-yl)-7-[1-(2-hydroxyethyl)-6-(4-fluorophenyl)indol-3-ylcarbonyl]-1H,3H-pyrrolo[1,2-c]thiazole Step 1. Preparation of
3-(Pyridin-3-yl)-7-[1-(2-dimethyl-tert-butylsilyloxyethyl)-6-(4-fluorophenyl)indol-3-ylcarbonyl]-1H,3H-pyrrolo[1,2-c]thiazole The desired compound was prepared according to the method of Example 46, except substituting 2-bromoethyoxydimethyl-tert-butylsilane for methyl acrylate.

Step 2. Preparation of
3-(Pyridin-3-yl)-7-[1-(2-hydroxyethyl)-6-(4-fluorophenyl)indol-3-ylcarbonyl]-1H,3H-pyrrolo[1,2-c]thiazole To a solution of 3-(Pyridin-3-yl)-7-[1-(2-dimethyl-tert-butylsilyloxyethyl)- 6-(4-fluorophenyl)indol-3-ylcarbonyl]-1H,3H-pyrrolo[1,2-c]thiazole (365 mg, 0.61 mmol) and 18-crown-6 (168 mg, 0.64 mmol) in acetonitrile (8 mL) was added cerium fluoride (695 mg, 4.6 mmol). The reaction mixture was stirred 17 hours at ambient temperature. The reaction mixture was quenched with H$_2$O and concentrated in vacuo. The residue was taken up in CH$_2$Cl$_2$ and filtered. The filtrate was concentration in vacuo. 3-(Pyridin-3-yl)-7-[1-(2-hydroxyethyl)-6-(4-fluorophenyl)indol- 3-ylcarbonyl]-1H,3H-pyrrolo[1,2-c]thiazole was obtained by flash chromatography on silica gel. m.p. 170°–171° C. $^1$H NMR (DMSO-d6, 300 MHz) δ3.73 (dd, 2H, J=6, 6Hz), 4.37 (t, 2H, J=1.5, 13.5Hz), 4.41 (d, 1H, J=13.5Hz), 4.57 (dd, 1H, J=1.5, 13.5Hz), 4.89 (t, 1H, J=6Hz), 6.65 (d, 1H, J=3Hz), 6.70 (bs, 1H), 6.82 (d, 1H, J=3Hz), 7.20 (t, 2H, J=9Hz), 7.29–7.35 (c, 1H), 7.63–7.70 (c, 2H), 7.85 (bs, 1H), 8.15 (s, 1H), 8.19 (d, 1H, J=6Hz), 8.31–8.35 (c, 2H), MS (DCI/NH$_3$) m/e 484 (M+H)$^+$. IR (KBr) 3440, 1590, 1510, 1480, 1380, 1230, 1180, 1160, 1080, 1070, 870, 820, 710. Anal calcd for C$_{28}$H$_{23}$FN$_3$O$_2$S: C, 68.27; H, 4.91; N, 8.53. Found: C, 68.57; H, 4.71; N, 8.42.

EXAMPLE 73

Preparation of
3-(1-Oxide-pyridin-3-yl)-7-[1-phenylsulfonyl-6-(4-fluorophenyl)indol-3-ylcarbonyl]-1H,3H-pyrrolo[1,2-c]thiazole The title compound was prepared by the procedure described in Example 34 using the compound resulting from Example 61, 3-(pyridin-3-yl)-7-[1-phenylsulfonyl- 6-(4-fluorophenyl)indol-3-ylcarbonyl]-1H,3H-pyrrolo[1,2-c]thiazole instead of 3-(pyridin-3-yl)-7-(1-N,N-dimethylcarbamoyl-6-phenylindol-3-yl)carbonyl- 1H,3H-pyrrolo[1,2-c]thiazole. m.p. 135°–137° C. $^1$H NMR (CDCl$_3$, 300 MHz) δ4.55 (d, 1H, J=13.5Hz), 4.62–4.69 (dd, 1H, J=13.5, 3Hz), 6.38 (s, 1H), 6.53 (d, 1H, J=3Hz), 6.85 (d, 1H, J=3Hz), 7.18 (t, 2H, J=7.5Hz), 7.25–7.32 (m, 1H), 7.43 (t, 1H, J=3Hz), 7.47–7.64 (cm, 6H), 7.95 (m, 1H), 7.97 (s, 1H), 8.15 (d, 1H, J=1.5Hz), 8.22 (s, 1H), 8.26 (s, 1H), 8.28–8.34 (m, 2H). MS (FAB) m/e 596 (M+1)$^+$.

EXAMPLE 74

Preparation of
3-[Pyridin-3-yl)-7-(6-pyrimid-2-ylindol-3-ylcarbonyl)-1H,3H-pyrrolo[1,2-c]thiazole Step. 1. Preparation of
3-(pyridin-3-yl)-7-(1-N,N-dimethylcarbamoyl-6-trimethylstannylindol-3-ylcarbonyl)-1H,3H-pyrrolo[1,2-c]thiazole 3-(pyridin-3-yl)-7-(1-N,N-dimethylcarbamoyl-6-bromoindol-3-ylcarbonyl)- 1H,3H-pyrrolo[1,2-c]thiazole (2.00 g, 4.04 mmol), prepared according to the method of Example 64, and hexamethylditin (1.65 g, 5.04 mmol) where combined under N$_2$ in a dry flask. Toluene (81 mL) was added via syringe and tetrakis(triphenylphosphine)palladium(0) (0.34 g, 0.29 mmol) was added under a stream of N$_2$. The reaction mixture was warmed to reflux and stirred for 2.5 hours. The reaction mixture was cooled to ambient temperature and partitioned between ethyl acetate and pH 7 K$_2$HPO$_4$$^-$/NaOH buffer. The organic phase was washed with buffer and brine, dried over Na$_2$SO$_4$, filtered, and concentrated in vacuo to a small volume. The suspension was filtered, and the filtrate concentrated in vacuo and azeotroped with ethanol and CH$_2$CL$_2$ to give an orange solid. Pure 3-(pyridin-3-yl)-7-(1-N,N-dimethlycarbamoyl- 6-trimethylstannylindol-3-ylcarbonyl)- 1H,3H-pyrrolo[1,2-c]thiazole (1.88 g, 80%), was obtained as a pale-yellow foam by flash chromatography on silica gel (3:1 then 5:1 ethyl acetate, hexanes).

Step 2. Preparation of
3-(Pyridin-3-yl)-7-(6-pyrimid-2-ylindol-3-ylcarbonyl)-1H,3H-pyrrolo[1,2-c]thiazole 3-(pyridin-3-yl)-7-(1-N,N-dimethylcarbamoyl-6-trimethylstannylindol- 3-ylcarbonyl)-1H,3H-pyrrolo[1,2-c]thiazole (0.23 g, 0.40 mmol), prepared in step 1, and 5-bromopyrimidine (76 mg, 0.48 mmol) where combined under N$_2$ in a dry flask. Toluene (4 mL) was added via syringe and tetrakis(triphenylphosphine)palladium(0) (30 mg, 0.026 mmol) was added under a stream of N$_2$. The reaction mixture was warmed to reflux and heated for 23 hours. The reaction mixture was cooled to ambient temperature and partitioned between ethyl acetate and pH 7 K$_2$HPO$_4$$^-$/NaOH buffer. The organic phase was washed once with buffer, and the combined aqueous layers where extracted once with ethyl acetate. The combined organic layers where washed with brine, dried over Na$_2$SO$_4$, filtered,and concentrated in vacuo. Flash chromatography on silica gel (100:1, then 65:1, then 40:1 then 20:1 CHCl$_3$, methanol) afforded pure 3-(Pyridin- 3-yl)-7-(6-pyrimid-2-ylindol-3-ylcarbonyl)-1H,3H-pyrrolo[1,2-c]thiazole (0.14 g., 70%), m.p. 125°–128° C. $^1$H NMR (CDCl$_3$, 300 MHz) δ3.18 (s, 6H), 4.60 (d, 1H, J=15.1 Hz), 4.72 (dd, 1H, J=1.8, 15.1 Hz), 6.40 (d, 1H, J=2.9 Hz), 6.49 (s, 1H), 6.79 (d, 1H, J=2.9 Hz), 7.44 (dd, 1H, J=5.0, 7.9 Hz), 7.57 (dd, 1H, J=1.5, 8.5 Hz), 7.74 (d, 1H, J=8.1 Hz), 7.87 (s, 1H), 8.04 (s, 1H), 8.48 (d, 1H, J=8.1 Hz), 8.62–8.70 (c, 2H), 9.03 (s, 2H), 9.22 (s, 1H), MS (DCI/NH$_3$) m/e 495 (M+1)$^+$. IR (KBr) 866 (s), 1181 (s), 1226 (m), 1386 (s), 1416 (s), 1484 (m), 1539 (s), 1612 (s), 1695 (s), 3437 (br). Anal calcd for C$_{27}$H$_{22}$N$_6$O$_2$S.0.75H2O: C, 63.82; H, 4.67; N, 16.54 Found: C, 53.45; H, 4.31; N, 16.19.

EXAMPLE 75

Preparation of
3-(1-Oxide-pyridin-3-yl)-7-[1-(2-N,N-dimethylcarbamoylmethyl)-
6-(4-fluorophenyl)indol-3-ylcarbonyl]-1H,3H-pyrrolo[1,2-c]thiazole The title compound was prepared by the procedure described in Example 34 using the compound resulting from Example 53, 3-(pyridin-3-yl)-7-[1-( 2-N,N-dimethylcarbamoylmethyl)-6-(4-fluorophenyl)indol-3-ylcarbonyl]-1H,3H-pyrrolo[1,2-c]thiazole instead of 3-(pyridin-3-yl)-7-(1-N,N-dimethylcarbamoyl- 6-phenylindol-3-yl)carbonyl-1H,3H-pyrrolo[1,2-c]thiazole, m.p. 180.7° C. $^1$H NMR (DMSO-d6, 300 MHz) δ4.55 (d, 1H, J=13.5Hz), 4.62–4.69 (dd, 1H, J=13.5, 3Hz), 6.38 (s, 1H), 6.53 (d, 1H, J=3Hz), 6.85 (d, 1H, J=3Hz), 7.18 (t, 2H, J=7.5Hz), 7.25–7.32 (m, 1H), 7.43 (t, 1H, J=3Hz), 7.47–7.64 (cm, 6H), 7.95 (m, 1H), 7.97 (s, 1H), 8.15 (d, 1H, J=1.5Hz), 8.22 (s, 1H), 8.26 (s, 1H), 8.28–8.34 (m, 2H). MS (FAB) m/e 541 (M+1)$^+$. IR (KBr) 1600(s), 1660(s). Anal calcd for $C_{30}H_{25}FN_4O_3S$: C, 62.98; H, 5.02; N, 9.79. Found: C, 62.65; H, 3.97; N, 9.47.

EXAMPLE 76

Preparation of
3-(Pyridin-3-yl)-7-[1-carbamoyl-6-(4-fluorophenyl)indol-3-ylcarbonyl]-
1H,3H-pyrrolo[1,2-c]thiazole The title compound was prepared by the procedure described in Example 37 using 3(-pyridin-3-yl)-7-[6-(4-fluorophenyl)indol-3-ylcarbonyl]- 1H,3H-pyrrolo[1,2-c]thiazole, prepared as in Example 28, instead of 3-(Pyridin-3-yl)- 7-(6-phenylmethoxyindol-3-yl)carbonyl-1H,3H-pyrrolo[1,2-c]thiazole. $^1$H NMR (DMSO-d6, 300 MHz) δ4.50 (d, 1H, J=15Hz), 4.68 (dd, 1H, J=2, 15Hz), 6.78 (d, 1H, J=3Hz), 6.81 (s, 1H), 7.05 (d, 1H, J=3Hz), 7.32 (t, 2H, J=9Hz), 7.45 (dd, 1H, J=5, 8Hz), 7.61 (dd, 1H, J=1, 9Hz), 7.66–7.77 (m, 3H), 8.00 (bs, 2H), 8.30 (d, 1H, J=9Hz), 8.53–8.60 (m, 4H), MS (DCI/NH$_3$) m/e 483 (M+H)$^+$, 440. Anal calcd for $C_{27}H_{19}FN_4O_2S$: C, 67.21; H, 3.97; N, 11.61. Found: C, 66.92; H, 3.88; N, 11.44.

EXAMPLE 77

Preparation of
3(1-Carbamoylamino-pyridin-3-yl)-7-[1-N,N-dimethylcarbamoyl-
6-(4-fluorophenyl)indol-3-ylcarbonyl]-1H,3H-pyrrolo[1,2-c]thiazole The title compound was prepared by the procedure described in Example 67 using semicarbazide instead of hydrazine. m.p. 156–163. $^1$H NMR (CD$_3$OD, 300 MHz) δ3.14 (s, 6H), 4.52 (d, 1H, J=15.0Hz), 4.69 (dd, 1H, J=15.0, 1.0Hz), 6.76 (d, 1H, J=3.0Hz), 6.79 (d, 1H, J=1.0Hz), 6.93 (d, 1H, J=3.0Hz), 7.19 (t, 2H, J= 9.0Hz), 7.58 (dd, 1H, J=1.0Hz), 7.70 (dd, 2H, J=9.0, 6.0Hz), 7.80 (d, 1H, J= 1.0Hz), 7.81 (m, 1H), 7.98 (d, 1H, J=8.5Hz), 8.26 (s, 1H), 8.30 (d, 1H, J= 9.0Hz), 8.57 (d, 1H, J=1.0Hz), 8.58 (m, 1H), IR (KBr) 3410, 1695, 1610, 1480, 1380. MS (FAB) m/e 569 (M+1)$^+$552. Anal calcd for $C_{30}H_{25}FN_6O_3S$: C, 63.37; H, 4.43; N, 14.78. Found: C, 60.91; H, 4.99; N, 13.65.

EXAMPLE 78

Preparation of
3-(1-Pyrid-3-oylamino-pyridin-3-yl)-7-[1-N,N-dimethylcarbamoyl-
6-(4-fluorophenyl)indol-3-ylcarbonyl]-1H,3H-pyrrolo[1,2-c]thiazole The title compound was prepared by the procedure described in Example 62 using 3-pyridinehydrazide instead of hydrazine. m.p. 140°–149° C. $^1$H NMR (CD$_3$OD, 300 MHz) δ3.15 (s, 6H), 4.56 (d, 1H, J=15.0Hz), 4.73 (dd, 1H, J=15.0, 3.0Hz), 6.78 (d, 1H, J=3.0Hz), 6.82 (d, 1H, J=1.0Hz), 6.96 (d, 1H, J=3.0Hz), 7.19 (t, 2H, J=9.0Hz), 7.50 (dd, 1H, J=8.5, 4.5Hz), 7.57 (dd, 1H, J=9.0, 1.0Hz), 7.70 (dd, 1H, J=8.5, 4.5Hz), 7.79 (d, 1H, J=1.0Hz), 7.96 (dd, 1H, J=8.5, 4.5Hz), 8.12 (d, 1H, J=8.5Hz), 8.25 (s, 1H), 8.30 (d, 1H, J=9.0Hz), 8.93 (dt, 1H, J=8.5, 1.0Hz), 8.62 (dd, 1H, J=4.5, 1.0Hz), 8.78 (bd, 1H, J=6.5Hz), 8.80 (bs, 1H), 9.20 (bs, 1H). MS (FAB) m/e 631 (M+1)$^+$. IR (KBr) 3410, 1695, 1600, 1540, 1480, 1390.

EXAMPLE 79

Preparation of
3-(3-Oxide-pyridin-3-yl)-7-[1-(2-aminosulfonylethyl)-
6-(4-fluorophenyl)indol-3-ylcarbonyl]-1H,3H-pyrrolo[1,2-c]thiazole The title compound was prepared by the procedure described in Example 34 using the compound resulting from Example 50, 3-(pyridin-3-yl)-7-[1-(2-sulfamylethyl)- 6-(4-fluorophenyl)indol-3-ylcarbonyl]-1H,3H-pyrrolo[1,2-c] thiazole instead of 3-(pyridin-3-yl)-7-(1-N,N-dimethylcarbamoyl-6-phenylindol-3-yl)carbonyl- 1H,3H-pyrrolo[1,2-c]thiazole. m.p. 171°–176° C. $^1$H (NMR D$_3$COD, 300 MHz) δ 3.65 (t, 2H, J=7. 81Hz), 4.5 (d, 1H, J=15Hz), 4.65 (dd, 1H, J=2, 15Hz), 4.8 (m, 2H), 6.67 (d, 1H, J=2Hz), 6.73 (d, 1H, J=3Hz), 6.97 (d, 1H, J=3Hz), 7.2 (t, 2H, J=9, 12Hz), 7.45 (d, 1H, J=9Hz), 7.52–7.6 (m, 2H), 7.7–7.78 (m, 3H), 8.24 (s, 1H), 8.25–8.34 (m, 3H). MS (FAB) m/e 563 (M+H)$^+$. Anal calcd for $C_{28}H_{23}N_4O_4S_2F$: C, 59.77; H, 4.12; N, 9.96. Found: C, 58.83; H, 4.37; N, 9.57.

EXAMPLE 80

Preparation of
3-(Pyridin-3-yl)-7-[1-N,N-dimethylcarbamoyl-6-(3-aminosulfonylphenyl)indol-
3-ylcarbonyl]-1H,3H-pyrrolo[1,2-c]thiazole The title compound was prepared by the procedure described in Example 74, using 4-bromophenylsulfonamide instead of 2-bromopyrimidine. m.p. 155°–160° C. $^1$H NMR (DMSO-d6, 300 MHz) δ3.09 (s, 6H), 4.50 (d, 1H, J=15.1 Hz), 4.68 (d, 1H, J=15.1 Hz), 6.74 (d, 1H, J=3.3 Hz), 6.81 (s, 1H), 6.94 (d, 1H, J=2.9 Hz), 7.42 (s, 2H), 7.44 (dd, 1H, J=5.0, 7.9 Hz), 7.66–7.73 (c, 2H), 7.93 (s, 5H), 8.36 (d, 1H, J=8.1 Hz), 8.41 (s, 1H), 8.57 (br s, 2H). MS (CDI/NH$_3$) m/e 572(M+)$^+$. IR 865 (s), 1163 (s), 1182 (s), 1226(m), 1341 (m), 1388 (s), 1433 (m), 1483 (m), 1537 (s), 1595 (m), 1609 (m), 1693 (s), 3427 (br). Anal calcd for $C_{29}H_{25}N_5O_4S_2 \cdot 0.6H_2O$: C, 67.09; H, 4.25; N, 11.25. Found C, 67.17; H, 4.15; N, 11.06.

EXAMPLE 81

Preparation of 3-(Pyridin-3-yl)-7-[1-(2-N-methylcarbamoylmethyl)-6-(4-fluorophenyl)indol-3-ylcarbonyl]-1H,3H-pyrrolo[1,2-c]thiazole The title compound was prepared by the procedure described in Example 53, using N-methyl bromoacetamide instead of N,N-dimethyl bromoactamide. m.p. 166°– 168° C. $^1$H NMR (DMSO-d6, 300 MHz) δ2.62 (d, 3H, J=5 Hz), 4.48 (d, 1H, J=15 Hz), 4.65 (dd, 1H, J=15, 2Hz), 5.02 (s, 2H), 6.72 (d, 1H, J=3Hz), 6.78 (bs, 1H), 6.89 (d, 1H, J=3 Hz), 7.31 (t, 2H, J=12 Hz), 7.44 (dd, 2H, J=12, 8 Hz), 7.66 (cm, 1H), 7.77 (cm, 3H), 8.15 (bd, 1H, J=5 Hz), 8.33 (d, 2H, J=12 Hz), 8.57 (cm, 2H). MS (DCI/NH$_3$) m/e 511 (M+H)$^+$, 528 (M+NH$_4$)$^+$. IR (KBr) 1600(s), 1660(s). Anal calcd for C$_{29}$H$_{23}$FN$_4$O$_2$S: C, 66.46; H, 4.71; N, 10.69. Found: C, 66.74; H, 4.38; N, 10.22.

EXAMPLE 82

Preparation of 3-(Pyridin-3-yl)-7-[1-N,N-dimethylcarbamoyl-6-(4-fluorophenyl)indol-3-ylcarbonyloxime]-1H,3H-pyrrolo[1,2-c]thiazole To a solution of 3-pyridin-3-yl)-7-[1-N,N-dimethylcarbamoyl- 6-(4-fluorophenyl)indol-3-ylcarbonyl]-1H,3H-pyrrolo[1,2-c]thiazole (0.33 g, 0.64 mmol), prepared as in Example 29, in 1:1 pyridine, ethanol (8 mL) was added hydroxylamine hydrochloride (0.36 g, 5.2 mmol). The reaction mixture was heated for 30 min at 110° C. The reaction mixture was cooled to ambient temperature and partioned between ether and H$_2$O. The organic phase was washed with pH 7 buffer and brine, dried over Na$_2$SO$_4$, filtered, and concentrated in vacuo. Flash chromatography on silica gel (3:1 hexanes,ethyl acetate, then ethyl acetate) afforded 3-(Pyridin- 3-yl)-7-[1-N,N-dimethylcarbamoyl-6-(4-fluorophenyl)indol- 3-ylcarbonyloxime]-1H,3H-pyrrolo[1,2-c] thiazole. m.p. 132° C. $^1$H NMR (D$_3$COD, 300 MHz) δ3.1 (s, 3H), 3.13 (s, 3H), 3.93–4.0 (c, 2H), 6.35 (d, 0.5H, J=3Hz), 6.45 (d, 0.5H, J=2Hz), 6.51(d, 0.5H, J=1.5Hz), 6.52 (s, 0.5H), 6.54 (s, 0.5H), 6.55 (d, 0.5H, J=4.5Hz), 7.11–7.19 (m, 2H), 7.38–7.45 (m, 2H), 7.53 (s, 1H), 7.61–7.7 (m, 2H), 7.8–7.84 (c, 2H), 7.95 (s, 0.5H), 7.97 (s, 0.5H), 8.43–8.53 (m, 2H). MS (FAB) m/e 526 (M+1)$^+$.

EXAMPLE 83

Preparation of 3-(Pyridin-3-yl)-7-[6-(4-fluorophenyl)indol-3-ylcarbonyloxime]- 1H,3H-pyrrolo[1,2-c]thiazole The title compound was prepared by the procedure described in Example 82, using 3-(pyridin-3-yl)-7-[6-(4-fluorophenyl)indol-3-ylcarbonyl]- 1H,3H-pyrrolo[1,2-c]thiazole instead of 3-pyridin-3-yl)-7-[1-N,N-dimethylcarbamoyl- 6-(4-fluorophenyl)indol-3-ylcarbonyl]-1H,3H-pyrrolo-[ 1,2-c]thiazole. m.p. 106°–108° C. $^1$H NMR (CDCl$_3$, 300 MHz) δ3.94–4.21 (c, 2H), 6.36 (d, 5H, J=3Hz), 6.46 (d, 0.5H, J=3Hz), 6.54 (s, 0.5H), 6.55 (s, 0.5H), 6.56–6.6 (c, 1H), 7.12–7.2 (m, 2H), 7.4–7.46 (m, 2H), 7.54 (s, 1H), 7.62–7.7 (m, 4H), 7.8–7.82 (br s, 1H), 7.95 (s, 0.5H), 7.98 (s, 0.5H), 8.42–8.54 (m, 2H). MS (DCI/NH$_3$) m/e 454 (M+H)$^+$.

EXAMPLE 84

Preparation of 3-(Pyridin-3-yl)-7-[1-(N-methyl-N-(dimethylaminoethyl))carbamoyl-6-(4-fluorophenyl)indol-3-ylcarbonyl]-1H,3H-pyrrolo[1,2-c]thiazole The title compound was prepared by the procedure described in Example 62 using N,N,N'-trimethylethylenediamine instead of ethanolamine. m.p. 149°–152° C. $^1$H NMR (DMSO-d6, 300 MHz) δ2.08 (s, 6H), 2.50 (m, 2H), 3.02 (s, 3H), 3.58 (t, 2H, J=6Hz), 4.49 (d, 1H, J=15Hz), 4.68 (dd, 1H, J=1, 15Hz), 6.73 (d, 1H, J=3Hz), 6.80 (s, 1H), 6.91 (d, 1H, J=3Hz), 7.32 (t, 2H, J=9Hz), 7.44 (dd, 1H, J=5, 8Hz), 7.49–7.79 (m, 4H), 7.88 (s, 1H), 8.32 (d, 1H, J=8Hz), 8.37 (s, 1H), 8.56–8.60 (m, 2H). MS (DCI/NH$_3$) m/e 568 (M+H)$^+$, 440. IR (CDCl$_3$) 1685, 1600, 1540, 1510. Anal calcd. for C$_{32}$H$_{30}$FN$_5$O$_2$S: C, 67.71; H, 5.33; N, 12.34. Found: C, 66.96; H, 5.10; N, 12.06.

EXAMPLE 85

Preparation of 3-(Pyridin-3-yl)-7-[1-N-carboxymethylcarbamoyl-6-(4-fluorophenyl)indol-3-ylcarbonyl]-1H,3H-pyrrolo[1,2-c]thiazole, The title compound was prepared by the procedure described in Example 62 using glycine instead of ethanolamine. m.p. 255° C. $^1$H NMR (DMSO-d6, 300 MHz) δ 4.01 (d, 2H, J=6H), 4.52(d, 1H, J=15Hz), 4.69 (dd, 1H, J=15, 2Hz), 6.79 (d, 1H, J=3Hz), 6.81 (d, 1H, J=1Hz), 7.06 (d, 1H, J=3Hz), 7.32 (t, 2H, J=9Hz), 7.45 (dd, 1H, J=5Hz, 8Hz), 7.63 (dd, 1H, J–1, 8Hz), 7.69 (dt, 1H, J=2, 9Hz), 7.72–7.78 (m, 2H), 8.32 (d, 1H, J=8Hz), 8.51 (d, 1H, J=1Hz), 8.5–8.61 (m, 3H), 9.12 (t, 1H, J=6Hz). MS (DCI/NH$_3$) m/e 541 (M+H)$^+$, 440. IR (KBr) 1708, 1600, 1532, 1510, 1475 Anal calcd for C$_{29}$H$_{21}$FN$_4$O$_4$S: C, 64.44; H, 3.92; N, 10.36. Found: C, 63.53; H, 3.82; N, 10.08.

EXAMPLE 86

Preparation of 3-(1-Methyl-pyridin-3-yl)-7-[1-N,N-dimethylcarbamoyl-6-(4-fluorophenyl)indol-3ylcarbonyl]-1H,3H-pyrrolo[1,2-c]thiazole The title compound was prepared by the procedure described in Example 33 using the compound resulting from Example 29, 3-(pyridin-3-yl)-7-8 1-N,N-dimethylcarbamoyl- 6-(4-fluorophenyl)indol-3-ylcarbonyl]- 1H,3H-pyrrolo [1,2-c]thiazole instead of 3-(pyridin-3-yl)-7-(1-N,N-dimethylcarbamoyl- 6-phenylindol-3-ylcarbonyl)-1H,3H-pyrrolo [1,2-c]thiazole, m.p. 168° C. $^1$H NMR (DMSO-d6, 300 MHz) δ3.08 (s, 6H), 4.37 (s, 3H), 4.54 (d, 1H, J=15Hz), 4.78 (dd, 1H, J=2, 15Hz), 6.83 (d, 1H, J=3Hz), 6.95(d, 1H, J=1Hz), 6.99 (d, 1H, J=3Hz), 7.32 (t, 2H, J=6Hz), 7.61 (dd, 1H, J=2, 9Hz), 7.73–7.82 (m, 3H), 8.16 (dd, 1H, J=7, 9Hz), 8.32 (d, 1H, J=9Hz), 8.38 (s, 1H), 8.49 (d, 1H, J=8Hz), 8.98 (d, 1H, J=6Hz), 9.03 (s, 1H). MS (FAB) me 525 (M+H)$^+$, 307, 289. Anal calcd for C$_{30}$H$_{26}$FlN$_4$O$_2$S: C, 55.22; H, 4.02; N, 8.59. Found: C, 53.97; H, 3.88; N, 8.39.

EXAMPLE 87

Preparation of
3-(Pyridin-3-yl)-7-(1-N,N-dimethylcarbamoyl-6-
thiazol-2-ylindol-3-ylcarbonyl)-
1H,3H-pyrrolo[1,2-c]thiazole The title compound was prepared by the procedure described in Example 74, using 2-bromothiazole instead of 2-bromopyrimidine. m.p. 123°–126° 1 C. $^1$H NMR (CDCl$_3$, 300 MHz) δ3.17 (s, 6H), 4.58 (d, 1H, J=15.4 Hz), 4.71 (dd, 1H, J=2.2, 15.1 Hz), 6.38 (d, 1H, J=3.0 Hz), 6.47 (s, 1H), 6.80 (d, 1H, J=2.9 Hz), 7.36 (d, 1H, J=2.9 Hz), 7.42 (dd, 1H, J=5.0, 7.9 Hz), 7.72 (d, 1H, J=7.7 Hz), 7.88 (d, 1H, J=3.3 Hz), 7.92 (dd, 1H, J=1.6, 8.3 Hz), 8.07 (s, 1H), 8.25 (s, 1H), 8.42 (d, 1H, J=8.1 Hz), 8.63 (br s, 1H), 8.65 (br s, 1H), MS (DCI/NH$_3$) m/e 500 (M+H)$^+$. IR (KBr) 857 (s), 1181 (s), 123 (m,), 1388 (s), 1435 (s), 1482 (s), 1538 (s), 1612 (s), 1696 (s), 3439 (br). Anal calcd for $C_{26}H_{21}N_5O_2S_2 \cdot 0.4H_2O$: C, 61.61; H, 4.34; N, 13.82. Found: C, 61.59; H, 3.95; N, 13.41.

EXAMPLE 88

Preparation of
3-(Pyridin-3-yl)-7-[1-N-sulfoethylcarbamoyl-6-(4-
fluorophenyl)indol- 3-yl
carbonyl]-1H,3H-pyrrolo[1,2-c]thiazole The title compound was prepared by the procedure described in Example 62 using taurine instead of ethanolamine. m.p. 238° C. (dec). $^1$H NMR (DMSO-d$_6$, 300 MHz) δ2.79(t,2H,J=6Hz), 4.51(d,1H,J=15Hz), 4.70 (d, 1H, J=15Hz), 6.80 (d, 1H,J=3Hz), 6.85 (s, 1H), 7.05 (d, 1H, J=3Hz), 7.32 (t,2H,J=2Hz), 7.57–7.65 (c,2H), 7.73–7.81 (c,2H), 7.84–7.90 (c,2H), 8.31 (d,1H,J=9Hz), 8.49 (s,1H), 8.53 (s,1H), 8.67 (bs,2H), 8.75 (bs,1H), IR (KBr cm$^{-1}$) 3440, 1710, 1610, 1540, 1510, 1475, 1425, 1220, 1040, 875, 820. MS (FAB) m/e 613(M+Na)$^+$, 591(M+H)$^+$, 207, 185, 115.

EXAMPLE 89

Preparation of
3-(Pyridin-3-yl)-7-[1-N,N-dimethylcarbamoyl-6-(2-
aminopyrimid-5-yl)indol-
3-yl)carbonyl-]-1H,3H-pyrrolo[1,2-c]thiazole The title compound was prepared by the procedure described in Example 74, using 2-amino-5-bromopyrimidine instead of 2-bromopyrimidine. m.p. 145°–148° C. $^1$H NMR (DMSO-d6, 300 MHz) δ3.07 (s, 6H), 4.49 (d, 1H, J=15.2 Hz), 4.66 (dd, 1H, J=1.6, 15.2 Hz), 6.73 (d, 1H, J=2.9 Hz), 6.77 (s, 2H), 6.80 (s, 1H), 6.91(d, 1H, J=3.3 Hz), 7.44 (dd, 1H, J=4.9, 7.8 Hz), 7.56 (dd, 1H, J=1.6, 8.6 Hz), 7.68 (d, 1H, J=8.2 Hz), 7.76 (s, 1H), 8.29 (d, 1H, J=8.2 Hz), 8.33 (s, 1H), 8.58 (s, 2H), 8.62 (s, 2H), MS (DCI/NH$_3$) m/e 510 (M+H)$^+$. IR (KBr) 863 (m), 1183 (m), 1225 (m), 1384 (m), 1437 (m), 1464 (s), 1539 (s), 1612 (s), 1693 (s), 3409 (br), 3438 (br). Anal calcd for $C_{27}H_{23}N_7O_2S \cdot H_2O$: C, 51.47; H, 4.78; N, 18.58 Found: C, 51.87; H, 4.74; N, 18.12.

EXAMPLE 90

Preparation of
3-(1-Oxide-pyridin-3-yl)-7-[1-(2-aminoethyl)-6-(4-
fluorophenyl)indol-
3-ylcarbonyl]-1H,3H-pyrrolo[1,2-c]thiazole The title compound was prepared by the procedure described in Example 34 using the compound resulting from Example 59, 3-(Pyridin-3-yl)-7-[1-(2-aminoethyl)- 6(4-fluorophenyl)indol-3-ylcarbonyl]-1H,3H-pyrrolo[1,2-c] thiazole instead of 3-(pyridin-3-yl)-7-(1-N,N-dimethylcarbamoyl-6-phenylindol-3-yl)carbonyl- 1H,3H-pyrrolo[1,2-c] thiazole. m.p. 178°–190° C. $^1$H NMR (CDCl$_3$, 300 MHz) δ3.87 (t, 2H, J=9Hz), 4.44 (t, 2H, J=9Hz), 4.59 (d, 1H, J=15Hz), 4.69 (dd, 1H, J=15, 1Hz) 6.37 (bs, 1H), 6.48 (d, 1H, J=3Hz), 6.87 (d, 1H, J=3Hz), 7.15 (t, 2H, J=12Hz), 7.37 (cm, 2H), 7.47 (bs, 1H) 7.53 (bd, 1H, J=12Hz), 7.62 (cm, 2H), 7.92 (s, 1H), 8.32 (cm, 2H), 8.48 (d, 1H, J=12Hz). MS (FAB) m/e 499 (M+1)$^+$. IR (KBr) 1515 (s), 1600 (s), 3430 (br). Anal calcd for $C_{28}H_{23}FN_4O_2S$: C, 67.45; H, 4.65; N, 11.24. Found: C, 55.69; H, 4.63; N, 8.40.

EXAMPLE 91

Preparation of 3-(1-Oxide-pyridin-3-yl)-7-8
1-N,N-dimethylcarbamoyl-
6-(4-hydrazinylcarbonylphenyl)indol-3-ylcarbonyl]-
1H,3H-pyrrolo[1,2-c]thiazole The title compound was prepared by the procedure described in Example 74, using 4-bromobenzoyl hydrazide instead of 2-bromopyrimidine. m.p. 151°–154° C. $^1$H NMR (DMSO-d6, 300 MHz) δ3.09 (s, 6H), 450 (d, 1H, J=14.7 Hz), 4.52 (s, 2H), 4.68 (d, 1H, J=14.3 Hz), 6.74 (d, 1H, J=2.9 Hz), 6.80 (s, 1H), 6.92 (d, 1H, J=2.9 Hz), 7.44 (dd, 1H, J=4.8, 7.7 Hz), 7.68 (d, 2H, J=8.1 Hz), 7.82 (d, 1H, J=8.5 Hz), 7.83 (s, 1H), 7.92 (d, 2H, J=9.6 Hz), 7.95 (d, 1H, J=8.5 Hz), 8.34 (d, 1H, J=8.5 Hz), 8.39 (s, 1H), 8.57 (br s, 2H), 9.85 (br s, 1H). MS (DCI/NH$_3$) m/e 551 (M+H)$^+$. IR (KBr) 864 (s), 1182 (m), 1226 (m), 1387 (s), 1433 (m), 1480 (s), 1538 (s), 1609 (s), 1692 (s), 3431 1 (br). Anal calcd for $C_{30}H_{26}N_6O_3S \cdot 0.85H_2O$: C, 63.66; H, 4.94; N, 14.85. Found: C, 63.99; H, 4.86; N, 14.47.

EXAMPLE 92

Preparation of
3-(1-Acetoxymethylpyridin-3-yl)-7-[1-N,N-
dimethylcarbamoyl-
6-(4-fluorophenyl)indol-3-ylcarbonyl]-1H,3H-
pyrrolo[1,2-c]thiazole To a solution of 3-(Pyridin-3-yl)-7-[1-N,N-dimethylcarbamoyl- 6-(4-fluorophenyl)indol-3-ylcarbonyl]-1H,3H-pyrrolo[1,2-c]thiazole (206 mg, 0.41 mmol) prepared as in Example 29, in acetone (8 mL) was added bromomethyl acetate (60 µL, 0.62 mmol). The reaction mixture was warmed to reflux and stirred for four hours. The reaction mixture was cooled to ambient temperature and concentrated to a foam. The foam was dissolved in methanol, and 3-(1-Acetoxymethylpyridin-3yl)- 7-[1-N,N-dimethylcarbamoyl-6-(4-fluorophenyl)indol-3-ylcarbonyl]- 1H,3H-pyrrolo[1,2-c]thiazole was precipitated addition of ether. m.p. 218°–223° 1 C. $^1$H NMR (DMSO-d6, 300 MHz), δ2.18 (s, 3H), 3.09 (s, 6H), 4.55 (d, 1H, J= 15.0Hz), 4.75 (dd, 1H, J=15.0, 1.0Hz), 6.41 (s, 2H), 6.86 (d, 1H, J=3.0Hz), 7.00 (d, 1H, J=3.0Hz), 7.01 (s, 1H), 7.32 (t, 2H, J=8.5Hz), 7.62 (dd, 1H, J=8.5, 1.0Hz), 7.77 (m, 2H), 7.81 (bs, 1H), 8.26 (dd, 1H, J=8.5, 1.0Hz), 8.31 (d, 1H, J= 8.5Hz), 8.39 (s, 1H), 8.61 (bd, 1H, J=8.5Hz), 9.20 (d, 1H), J=6.0Hz), 9.22 (bs, 1H), MS (FAB) m/e 583. 511. IR (KBr) 3450 (br), 1685, 1480, 1220.

EXAMPLE 93

Preparation of 3-(Pyridin-3-yl)-7-[1-N-methyl-N-
hydroxymethylcarbamoyl-
6-(4-fluorophenyl)indol-3-ylcarbonyl]-1H,3H-
pyrrolo[1,2-c]thiazole To a solution of 3-(pyridin-3-yl)-7-[1-(2-N-methylcarbamoylmethyl)- 6-(4-fluorophenyl)indol-3-ylcarbonyl]-1H, 3H-pyrrolo[1,2-c]thiazole (100 mg, 0.20 mmol), prepared as in Example 81, in THF (5 mL) was added a solution of $K_2CO_3$ (13 mg, 0.098 mmol) in $H_2O$ (5 mL). Formaldehyde (37% aqueous solution, 10 mL, 123 mmol) was added and the reaction mixture was stirred overnight at ambient temperature. The THF was removed in vacuo and the residue was extracted three times with ethyl acetate. The combined organic layers were washed with saturated aqueous $NaHCO_3$ and concentrated in vacuo. Purification by flash chromatography on silica gel (2% methanol, ethyl acetate) afforded 3-(Pyridin-3-yl)-7-[1-N-methyl-N-hydroxymethyl-carbamoyl- 6-(4-fluorophenyl)indol-3-ylcarbonyl]- 1H,3H-pyrrolo[1,2-c]thiazole (32 mg). m.p. 172°–182° C. (decomp). $^1H$ NMR (DMSO-d6, 300 MHz) δ2.89 (s, 2.25H), 3.15 (s, 0.75H), 4.48 (d, 1H, J=15Hz), 4.62 (dd, 1H, J=15, 1Hz), 4.71 (d, 0.5H, J=10Hz), 4.92 (d, 1.5H, J=10Hz), 5.39 (s, 0.5H), 5.47 (s, 1.5H), 5.9 (t, 0.25, J=10Hz), 6.21 (t, 0.75H, J=10Hz), 6.71 (d, 1H, J=3Hz), 6.78 (s, 1H), 6.87 (d, 0.25H, J=3Hz), 6.88 (d, 0.75, J=3Hz), 7.312 (t, 2H, J=12Hz), 7.44 (cm, 1H), 7.51 (d, 1H, J=12Hz), 7.65 (d, 1H, J=12Hz), 7.75 (cm, 3H), 8.27 (s, 1H), 8.32 (d, 1H, J=12Hz), 8.57 (d, 2H, J=9Hz). MS (FAB) m/e 541 (M+1)$^+$. Anal calcd for $C_{30}H_{25}N_4O_3SF$: C, 63.48; H, 4.97; N, 9.87. Found: C, 63.77; H, 5.87; N, 7.45.

EXAMPLE 94

Preparation of
3-(Pyridin-3-yl)-7-[1-cyanomethyl-6-(4-fluorophenyl)indol-3-ylcarbonyl]-1H,3H-pyrrolo[1,2-c]thiazole The desired compound was prepared according to the method of Example 46, except substituting iodoacetonitrile for methyl acrylate. m.p. 219–223. $^1H$ NMR (DMSO-d6, 300 MHz) δ4.5 (d, 1H, J=1.5Hz), 4.65 (dd, 1H, J=1.5, 0.3Hz), 5.7 (s, 2H), 6.75 (d, 1H, J=0.3Hz), 6.8 (d, 1H, J=0.2Hz), 6.93 (d, 1H, J=0.3Hz), 7.35 (t, 2H, J=0.9, 1.2Hz), 7.4 (dd, 1H, 0.6, 0.9Hz), 7.63 (dd, 1H, J=0.9, 0.3Hz), 7.68 (dd, 1H, J=0.9, 0.3Hz), 7.83 (dd, 2H, J=0.3, 0.9Hz), 8.2 (s, 1H), 8.35 (d, 1H), J=0.9Hz), 8.48 (s, 1H), 8.55–8.60 (m, 2H), MS (DCI/NH$_3$) m/e 479 (M+H)$^+$. IR (KBr) 2200.

EXAMPLE 95

Preparation of
3-(Pyridin-3-yl)-7-[1-carbamoylmethyl-6-(4-fluorophenyl)indol-3-ylcarbonyl]-1H,3H-pyrrolo[1,2-c]thiazole To a solution of 3-(pyridin-3-yl)-7-[1-cyanomethyl-6-(4-fluorophenyl)indol- 3-ylcarbonyl]-1H,3H-pyrrolo[1,2-c]thiazole (290 mg, 0.607 mmol), prepared as in Example 94, in 2:1 isopropanol, methanol (60 mL). was added a solution of borax (sodium tetraborate decahydrate, 0.693 g, 1.82 mmol) in $H_2O$ (20 mL). The reaction mixture was heated for four hours at 80° C. The reaction mixture was cooled to ambient temperature and concentrated in vacuo. The residue was taken up in CHCl$_3$ and filtered through a pad of celite. The organic phase was washed with brine, dried over MgSO$_4$, filtered, and concentrated in vacuo. The crude product was purified by flash chromatography on silica gel to give 3-(Pyridin-3-yl)-7-[1-carbamoylmethyl- 6-(4-fluorophenyl)indol-3-ylcarbonyl]-1H,3H-pyrrolo[1,2-c]thiazole (20 mg), m.p. 215°–225° C. $^1H$ NMR (DMSO-d6, 300 MHz) δ4.49 (d, 1H, J=15Hz), 4.65 (dd, 1H, J=15, 3Hz), 5.03 (s, 2H), 6.73 (d, 1H, J=3Hz), 6.79 (s, 1H), 6.9 (d, 1H, J=3Hz), 7.28–7.39 (m, 3H), 7.40–7.48 (m, 1H), 7.53 (d, 1H, J=9Hz), 7.6–7.8 (m, 5H), 8.33 (m, 1H), 8.58 (m, 1H), MS (DCI/NH$_3$) m/e 497 (M+H)$^+$. Anal calcd for $C_{28}H_{21}FN_4O_2S$: C, 67.73; H, 4.26; N, 11.28. Found: C, 65.63; H, 4.37; N, 10.31.

EXAMPLE 96

Preparation of
3-(Pyridin-3-yl)-7-[1-carboxymethyl-6-(4-fluorophenyl)indol-3-ylcarbonyl]-1H,3H-pyrrolo[1,2-c]thiazole Step 1. Preparation of
3-(pyridin-3-yl)-7-[1-carboxymethyl-6-(4-fluorophenyl)indol-3-ylcarbonyl]-1H,3H-pyrrolo[1,2-c]thiazole The desired compound was prepared according to the method of Example 46, except substituting ethyl chloroacetate for methyl acrylate.

Step 2. Preparation of
3-(Pyridin-3-yl)-7-[1-carboxymethyl-6-(4-fluorophenyl)indol-3-ylcarbonyl]-1H,3H-pyrrolo[1,2-c]thiazole The desired compound was prepared according to the method of Example 49, step 2except substituting 3-(pyridin-3-yl)-7-[1-carboethoxymethyl- 6-(4-fluorophenyl)indol-3-ylcarbonyl]-1H,3H-pyrrolo[1,2-c]thiazole, prepared in step 1, for 3-(Pyridin-3-yl)-7-[1-(2-carbomethoxyethyl)-6-(4-fluorophenyl)indol- 3-ylcarbonyl]-1H,3H-pyrrolo[1,2-thiazole, m.p. 240°–249° C. $^1H$ NMR (DMSO-d6, 300 MHz) δ4.45 (d, 1H, J=1.5Hz), 4.65 (dd, 1H, J=1.5, 0.3Hz), 4.84 (s, 2H), 6.7 (d, 1H, J=0.3Hz), 6.78 (s, 1H), 6.87 (d, 1H, J=0.3Hz), 7.3 (t, 2H, J= 0.9, 1.5Hz), 7.4–7.5 (m, 2H), 7.6–7.8 (m, 4H), 8.25–8.33 (m, 2H), 8.5–8.6 (m, 2H), MS (DCI/NH$_3$) m/e 498 (M+H)$^+$.

EXAMPLE 97

Preparation of
3-(Pyridin-3-yl)-7-[1-(1H-tetrazol-5-ylmethyl)-6-(4-fluorophenyl)indol-3-ylcarbonyl]-1H,3H-pyrrolo[1,2-c]thiazole A mixture of 3(pyridin-3-yl)-7-[1-cyanomethyl-6-(4-fluorophenyl)indol- 3-ylcarbonyl]-1H,3H-pyrrolo[1,2-c]thiazole (77 mg, 0.161 mmol), prepared as in Example 94, dibutyltin oxide (40 mg, 0.161 mmol), and trimethylsilylazide (47.3 μL, 0.322 mmol) in toluene (15 mL) was heated at reflux for three hours. The reaction mixture was cooled to ambient temperature and concentrated in vacuo. The crude product was azeotroped with CH$_2$Cl$_2$ and purified by flash chromatography on silica gel (9:1 CHCl$_3$, methanol) to give 3-(Pyridin-3-yl)-7-[1-(1H-tetrazol-5-ylmethyl)- 6-(4-fluorophenyl)indol-3-ylcarbonyl]-1H,3H-pyrrolo[1,2-c]thiazole (53 mg), m.p. 110°–118° C. $^1H$ NMR (D$_3$COD, 300 MHz) δ45 (d; 1H, J=15Hz), 4.63 (dd, 1H, 15, 3Hz), 5.75 (s, 2H), 6.57 (d, 1H, J=3Hz), 6.67 (bs, 1H), 6.98 (d, 1H, J=3Hz, 7.15 (t, 2H, J=9Hz), 7.45–7.51 (m, 2H), 7.67–7.77 (m, 3H), 7.79 (s, 1H), 8.25 (s, 1H), 8.31 (d, 1H, 9Hz), 8.55 (bs, 2H). MS (FAB) m/e 522 (M+H)$^+$.

EXAMPLE 89

Preparation of
3-(Pyridin-3-yl)-7-[1-N,N-dimethylcarbamoyl-6(2,4(1H,3H)-pyrimidinedion-5-yl)indol-3-yl)carbonyl]-1H,3H-pyrrolo[1,2-c]thiazole The title compound was prepared by the procedure described in Example 74, using 5-bromouracil instead of 2-bromopyrimidine. $^1H$ NMR (DMSO-d6, 300 MHz) δ3.06 (s, 6H), 4.48 (d, 1H, J=15.1 Hz), 4.66 (d, 1H, J=15.4 Hz), 6.72 (d, 1H, J=3.3 Hz), 6.79 (s, 1H), 6.90 (d, 1H, J=2.9 Hz), 7.40–7.47 (c, 2H), 7.65– 7.70 (c, 2H), 7.83 (s, 1H), 8.20 (d, 1H, J=8.1 Hz), 8.32 (s, 1H), 8.55–8.59 (c, 2H), 11.17 (br s, 0.67H), 11.24 (br s, 0.33H), 11.27 (s, 0.67H), 11.52 (br s, 0.33H). MS (DCI/NH$_3$) m/e 527 (M+H)$^+$.

EXAMPLE 99

Preparation of
3-(Pyridin-3-yl)-7-[1-N-sulfoethylcarbamoyl-6-(4-fluorophenyl)indol-3-ylcarbonyl]-1H,3H-pyrrolo[1,2-c]thiazole The title compound was prepared by the procedure described in Example 62 using ethylamine instead of ethanolamine. m.p. 210°–213° C. $^1$H NMR (DMSO-d6, 300 MHz), δ1.21 (t, 3H, J=7Hz), 3.35–3.42 (m, 2H), 4.51 (d, 1H, J=15Hz), 4.68 (dd, 1H, J=2, 15Hz), 6.78 (d, 1H, J=3Hz), 6.81 (s, 1H), 7.05 (d, 1H, J=3Hz), 7.32 (t, 2H, J=9Hz), 7.45 (dd, 1H, J=5, 8Hz), 7.61 (dd, 1H, J=1, 9Hz), 7.65 (m, 3H), 8.31 (d, 1H, J=8Hz), 8.50–8.61 (m, 4H), 8.68 (t, 1H, J=6Hz). MS (DCI/NH$_3$) m/e 511 (M+H)$^+$, 441,417. IR (KBr) 1710, 1600, 1532, 1512, 1475, Anal calcd for C$_{29}$H$_{23}$FN$_4$O$_2$S: C, 68.22; H, 4.54; N, 10.97. Found: C, 67.96; H, 4.42; N, 10.73.

EXAMPLE 100

Preparation of
3-(Pyridin-3-yl)-7-[1-N-sulfoethylcarbamoyl-6-(4-fluorophenyl)indol-3-ylcarbonyl]-1H,3H-pyrrolo[1,2-c]thiazole The title compound was prepared by the procedure described in Example 62 using leucine instead of ethanolamine. m.p. 214°–215° C. 1HMR (DMSO-d6, 300 MHz) δ0.91 (bs, 6H), 1.24 (bs, 3H), 1.72 (bs, 3H), 4.25 (bs, 1H), 4.51 (bd, 1H, J=15Hz), 4.67 (bd, 1H, J=15Hz), 6.80 (bs, 2H), 7.09 (bs, 1H), 7.33 (t, 2H, J=9Hz), 7.40–7.48 (c, 1H), 7.61 (bd, 1H, J=9Hz), 7.67–7.81 (c, 3H), 8.32 (d, 1H, J=7.5Hz), 8.51–8.62(c, 4H), MS (DCI/NH$_3$) m/e 597 (M+H)$^+$, 440, 228, 200. IR (KBr) 3420, 2950, 2940, 1710, 1600, 1535, 1515, 1480, 1430, 1380, 1220, 1160, 1140, 820, 710.

EXAMPLE 101

Preparation of
3-(Pyridin-3-yl)-7-(1-N,N-dimethylcarbamoyl-6-thiophen-2-ylindol-3-ylcarbonyl)-1H,3H-pyrrolo[1,2-c]thiazole The desired compound was prepared according to the method of Example 74, except substituting 2-bromothiophene for 5-bromopyrimidine. m.p. 115°–118° C. $^1$H NMR (DMSO-d6, 300 MHz) δ3.08 (s, 6H), 4.50 (d, 1H, J=15.1 Hz), 4.66 (dd, 1H, J=1.8, 15.1 Hz), 6.72 (d, 1H, J=2.9 Hz), 6.80 (d, 1H, J=1.5 Hz), 6.91 (d, 1H, J=3.3 Hz), 7.16 (dd, 1H, J=3.8, 5.0 Hz), 7.44 (dd, 1H, J=5.0, 7.9 Hz), 7.55 (d, 1H, J=5.5 Hz), 7.56 (d, 1H, J=3.7 Hz), 7.64 (dd, 1H, J=1.5, 8.4 Hz), 7.68 (dt, 1H, J=1.9, 8.1 Hz), 7.85 (dd, 1H, J=0.7, 1.5 Hz), 8.26 (d, 1H, J=8.4 Hz), 8.35 (s, 1H), 8.54–8.60 (c, 2H), MS (DCI/NH$_3$) m/e 499 (M+H)$^+$. IR (KBr) 707 (m), 862 (m), 1180 (s), 1224 (m), 1387 (m), 1435 (m), 1483 (s), 1539 (s), 1611 (m), 1694 (s), 3439 (br). Anal calcd for C$_{27}$H$_{22}$N$_4$O$_2$S$_2$.0.1C$_5$H$_{12}$: C, 65.30; H, 4.62; N, 11.08. Found: C, 65.23; H, 4.73; N, 10.72.

EXAMPLE 102

Preparation of
3-(Pyridin-3-yl)-7-(1-N,N-dimethylcarbamoyl-6-(4-hydroxymethyl)phenylindol-3-ylcarbonyl)-1H,3H-pyrrolo[1,2-c]thiazole The desired compound was prepared according to the method of Example 74, except substituting 4-bromobenzyl alcohol for 5-bromopyrimidine. m.p. 134°–137° C. $^1$H NMR (DMSO-d6, 300 MHz) δ3.08 (s, 6H), 4.50 (d, 1H, J=15.1 Hz), 4.56 (d, 2H, J=5.5 Hz), 4.67 (dd, 1H, J=2.0, 15.2 Hz), 5.20 (t, 1H, J=5.7 Hz), 6.74 (d, 1H, J=3.3 Hz), 6.80 (d, 1H, J=1.8 Hz), 6.92 (d, 1H, J=3.3 Hz), 7.41–7.47 (m, 1H), 7.42 (d, 2H, J=8.5 Hz), 7.62 (dd, 1H, J=1.8, 8.4 Hz), 7.66–7.71 (m, 1H), 7.68 (d, 2H, J=8.1 Hz), 7.83 (s, 1H), 8.30 (d, 1H, J=8.5 Hz), 8.35 (s, 1H), 8.56– 8.59 (c, 2H), MS (FAB) m/e 523 (M+1)$^+$. IR (KBr) 866 (s), 1182 (s), 1225 (m), 1388 (s), 1433 (m), 1482 (s), 1538 (s), 1610 (m), 1694 (s), 3436 (br). Anal calcd for C$_{30}$H$_{26}$N$_4$O$_3$S.0.75H$_2$O: C, 67.21; H, 5.17; N, 10.45. Found: C, 67.44; H, 4.83; N, 10.46.

EXAMPLE 103

Preparation of
2-Oxide-3-(1-oxide-pyridin-3-yl)-7-[1-N,N-dimethylcarbamoyl-6-(4-fluorophenyl)indole-3-ylcarbonyl]-1H,3H-pyrrolo[1,2-c]thiazole The desired compound was prepared according to the method of Example 13, except substituting 3-(1-oxide-pyridin-3-yl)-7-[1-N,N-dimethylcarbamoyl-6-(4-fluorophenyl)indole- 3-ylcarbonyl]-1H,3H-pyrrolo[1,2-c]thiazole, prepared as in Example 39, for 3-(pyridin-3-yl)-7-(1-tert-butyloxycarbonylindol-3-yl)carbonyl- 1H,3H-pyrrolo[1,2-c]thiazole. m.p. 187°–206° C. $^1$H NMR (DMSO-d6, 300 MHz) δ 3.10 (s, 6H), 4.29 (d, 1H, J=17.0Hz), 4.75 (d, 1H, J=17.0Hz), 6.61 (s, 1H), 6.92 (bd, 1H, J=8.0Hz), 7.04 (d, 1H, J=3.0Hz), 7.18 (d, 1H, J=3.0Hz), 7.31 (t, 2H, J=8.5 Hz), 7.45 (dd, 1H, J=7.0, 8.0Hz), 7.52 (dd, 1H, J=1.5, 8.5Hz), 7.78 (m, 2H), 7.82(d, 1H, J=1.5Hz), 8.09 (s, 1H), 8.24 (d, 1H, J=6.0Hz), 8.31 (d, 1H, J=8.0Hz), 8.43 (s, 1H). MS (FAB) m/e 543 (M+1)$^+$. IR (KBr) 1695, 1480,

EXAMPLE 104

Preparation of
3-(Pyridin-3-yl)-7-[1-N,N-dimethylcarbamoyl-6-(4-fluorophenyl)indol-3-ylcarbonylhydrazone]-1H,3H-pyrrolo[1,2-c]thiazole To a solution of 3-(pyridin-3-yl)-7-[1-N,N-dimethylcarbamoyl- 6-(4-fluorophenyl)indol-3-ylcarbonyl]-1H,3H-pyrrolo[1,2-c]thiazole (0.30 g, 0.59 mmol), prepared as in Example 29, in n-butanol was added hydrazine hydrate (55% solution in H$_2$O, 0.20 mL, 2.9 mmol) and acetic acid (0.20 mL). The reaction mixture was heated at 80°–90° C. for 72 hours. The reaction mixture was cooled to ambient temperature and concentrated in vacuo. 3-(Pyridin-3-yl)-7-[1-N,N-dimethylcarbamoyl- 6-(4-fluorophenyl)indol-3-ylcarbonylhydrazone]-1H,3H-pyrrolo[1,2-c]thiazole was obtained by flash chromatography on silica gel. m.p. 150°–151° C. $^1$H NMR (D$_3$COD, 300 MHz) δ3.1 (s, 6H), 3.95–4.1 (dd, 2H, J=1.5, 12Hz), 6.5 (d, 1H, J=3Hz), 6.63 (br s, 1H), 6.66 (d, 1H, J=3Hz), 7.13–7.2 (c, 2H), 7.35 (s, 1H), 7.42 (dd, 1H, J=1.5, 6Hz), 7.45–7.5 (c, 1H), 7.64–7.59 (c, 2H), 7.75–7.78 (c, 1H), 7.79–7.8 (c, 1H), 8.08 9d, 1H, J=7.5Hz), 8.5 (br, s, 1H), 8.54 (d, 1H, J=3Hz). MS (FAB) m/e 525 (M+1)⁺.

EXAMPLE 105

Preparation of 3-(Pyridin-3-yl)-7-[1-N-(2-(4-imidazolyl)ethyl) carbamoyl-6-(4-fluorophenyl)indol-3-ylcarbonyl]-1H,3H-pyrrolo[1,2-c]thiazole The desired compound was prepared according to the method of Example 62, except substituting histamine for ethanolamine, m.p. 156°–158° C. ¹H NMR (D₃COD, 300 MHz), δ2.97 (t, 2H, J=7.5Hz), 3.68 (t, 2H, J=7.5Hz), 4.50 (d, 1H, J= 15Hz), 4.65 (dd, 1H, J=3, 15Hz), 6.60 (d, 1H, J=3Hz), 6.79 (d, 1H, J=1.5Hz), 6.92 (bs, 1H), 6.96 (d, 1H, J=3Hz), 7.19 (t, 2H, J=9Hz), 7.45–7.51 (c, 1H), 7.55 (dd, 1H, J=1.5, 9Hz), 7.59 (d, 1H, J=1Hz), 7.63–7.70 (c, 2H), 7.75 (dt, 1H, J=1.5, 7.5Hz), 8.26 (d, 1H, J=7.5Hz), 8.34 (s, 1H), 8.37 (d, 1H, J=1Hz), 8.52 (d, 1H, J=1.5Hz), 8.55 (dd, 1H, J=1.5, 4.5Hz), MS (FAB) m/e 577 (M+H)⁺, 460, 440, 154, 136. IR (KBr) 3410, 1710, 1600, 1530, 1510, 1475, 1430, 1220, 875, 820. Anal calcd for C₃₂H₂₇FN₆O₃S: C, 64.63; H, 4.58; N, 14.13. Found: C, 64.88; H, 4.28; N, 14.16.

EXAMPLE 106

Preparation of 3-(pyridin-3-yl)-7-[1-N,N-dimethylcarbamoyl-6-(4-fluorophenyl)indol-3-ylcarbonylsemicarbazide]-1H,3H-pyrrolo[1,2-c]thiazole To a suspension of 3-(pyridin-3-yl)-7-[1-N,N-dimethylcarbamoyl- 6-(4-fluorophenyl)indol-3-ylcarbonyl]-1H,3H-pyrrolo[1,2-c]thiazole (0.62 g, 1.21 mmol), prepared as in Example 29, in 1:1 ethanol, pyridine (12 mL) was added semicarbazide hydrochloride (1.08 g, 9.72 mmol) and the reaction mixture was heated for 24 hours at 105° C. The reaction mixture was cooled to ambient temperature and concentrated in vacuo. The residue was taken up in CH₂Cl₂ and the solution was washed with saturated aqueous NaHCO₃, dried over Na₂SO₄, filtered, and concentrated. Flash chromatography on silica gel (20% methanol/acetone) provided 3-(pyridin- 3-yl)-7-[1-N,N-dimethylcarbamoyl-6-(4-fluorophenyl)indol- 3-ylcarbonylsemicarbazide]-1H,3H-pyrrolo[1,2-c]thiazole (30 mg), m.p. 160°–161° C. ¹H NMR (D₃COD, 300 MHz) δ3.3 (s, 6H), 4.03–4.35 (2H), 6.45–6.67 (3H), 7.07– 7.2 (3H), 7.35–7.5 (4H), 7.6–7.75 (4H), 8.4–8.53 (2H), 8.4–8.53 (2H). MS (FAB) m/e 567 (M+1)⁺.

We claim:

1. A compound of formula:

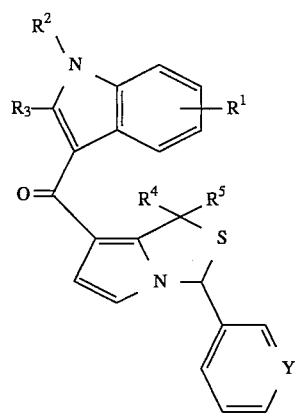

or a pharmaceutically acceptable salt thereof wherein
R¹ is one or more groups independently selected from the group consisting of
  hydrogen,
  halogen,
  alkyl of from one to six carbon atoms,
  alkoxy of from one to six carbon atoms,
  alkanoyl of from one to seven carbon atoms, phenyl, optionally substituted by
    alkyl of from one to six carbon atoms,
    alkoxy of from one to sic carbon atoms, or
    halogen,
  -NR⁷R⁸ where R⁷ and R⁸ are independently selected from hydrogen,
    alkyl of from one to six carbon atoms,
  -COOR⁹ where R⁹ is independently selected from hydrogen, and alkyl of from one to six carbon atoms,
  -CONR⁷R⁸ where R⁷ and R⁸ are as defined above, and
  -SO₂NR⁷R⁸ where R and R⁸ are as defined above,
  benzoyl, wherein the phenyl moiety is optionally substituted by
    halogen,
    alkyl of from one to six carbon atoms, or
    alkoxy of from one to six carbon atoms,
  phenoxy optionally substituted by
    halogen,
    alkyl of from one to six carbon atoms, or
    alkoxy of from one to six carbon atoms,
  phenylalkyloxy in which the alkyl portion contains from one to six carbon atoms and the phenyl is optionally substituted with
    halogen,
    alkyl of from one to six carbon atoms, or
    alkoxy of from one to six carbon atoms, or
  phenylalkanoyl in which the alkanoyl portion contains from one to seven carbon atoms and the phenyl moiety is optionally substituted by
    halogen,
    alkyl of from one to six carbon atoms, or
    alkoxy of from one to six carbon atoms;
R² is selected from the group consisting of hydrogen,
  alkyl of from one to six carbon atoms,
  -(CH₂)ₚCOOR⁹, where p is 0 or an integer of from 1 to 4 and R⁹ is as defined above,
  -(CH₂)qNR⁷R⁸, where q is an integer of from 2 and 4 and R⁷ and R⁸ are as defined above,
  -(CH₂)ₚCOR⁹ where R⁹ is as defined above,
  -(CH₂)qOH,
  -(CH₂)ₚSO₂R⁹ where p and R⁹ are as defined above, -(CH$_2$S0$_2$NR$^7$R$^8$ where p, R$^7$ and R$^8$ are as defined above,
-(CH$_2$)$_p$CONR$^{10}$R$^{11}$, where p is defined above and R$^{10}$ and R$^{11}$ are independently selected from
hydrogen,
alkyl of from one to six carbon atoms,
-CONHNH$_2$, or;
-(CH$_2$)$_r$phenyl, where r is integer of 1 to 4 and the phenyl moiety is optionally substituted by
halogen,
alkyl of from one to six carbon atoms, or
alkoxy of from one to six carbon atoms;

R$^{3l}$, R$^4$, and R$^5$ are independently selected from hydrogen or alkyl of from one to six carbon atoms; and Y is selected from the groups consisting of
N
N+R$^{12}$ where R$^{12}$ is an alkyl group of from one to six carbon atoms,
N$^+ \rightarrow$O$^-$
N$^+$OR$^{12}$ where R$^{12}$ is as defined above,
N$^+$NR$^7$R$^8$ where R$^7$ and R$^8$ are as defined above,
N$^+$NHCONR$^7$R$^8$ where R$^7$ and R$^8$ are as defined above,
N$^+$NHCOR$^9$ where R$^9$ is as defined above,
N$^+$OCR$^7$R$^8$OCOR$^{12}$ where R$^7$, R$^8$ and R$^{12}$ are as defined above,
N$^+$CR$^7$R$^8$OCONR$^7$R$^8$ where R$^7$ and R$^8$ are as defined above,
N$^+$O-CR$^7$R$^8$CONR$^7$R$^8$ where R$^7$ and R$^8$ are as defined above.

2. A compound as defined by claim 1 or a pharmaceutically acceptable salt thereof wherein R$^1$ is phenyl, optionally substituted by alkyl of from one to six carbon atoms, alkoxy of from one to six carbon atoms, or halogen, R$^2$ is selected from the group consisting of hydrogen, alkyl of from one to six carbon atoms;
-(CH$_2$)$_p$COOR$^9$, where p and R$^9$ are as defined therein,
-(CH$_2$)$_q$NR$^7$R$^8$, where q, R$^7$ and R$^8$ are as defined therein,
-(CH$_2$)$_p$COR$^9$ where p and R$^9$ is as defied therein,
-(CH$_2$)$_q$OH where q is as defined therein,
-(CH$_2$)$_p$SO$_2$R$^7$ where p and R$^7$ are as defined therein,
-(CH$_2$)$_p$SO$_2$NR$^7$R$^8$ where p, R$^7$ and R$^8$ are as defined therein,
-(CH$_2$)$_p$CONR$^{10}$R$^{11}$, where p, R$^{10}$ and R$^{11}$ are as defined therein,
-(CH$_2$)$_r$CN,
-CONHNH$_2$, or
-(CH$_2$)$_r$phenyl, where r is as defined therein and the phenyl moiety is optionally substituted by
halogen,
alkyl of from one to six carbon atoms, or
alkoxy of from one to six carbon atoms;

R$^3$, R$^4$, and R$^5$ are hydrogen;

X is S;

Y is selected from the group consisting of
N,
N$^+ \rightarrow$O$^-$,
N$^+$-CR$^7$R$^8$OCOR$^{12}$ where R$^7$, R$^8$ and R$^{12}$ are as defined therein, and
N$^+$-OCR$^7$R$^8$OCOR$^{12}$ where R$^7$, R$^8$ and R$^{12}$ are as defined therein, and.

3. A compound as defined by claim 2 or a pharmaceutically acceptable salt thereof wherein R$^1$ is phenyl or 4-fluorophenyl and R$^2$ is selected from the group consisting of CONH$_2$, CONHCH$_3$, and CON(CH$_3$)$_2$.

4. A compound as defined by claim 1 is selected from the group consisting of:

3-(pyridin-3-yl)-7-(indol-3-yl)carbonyl-1H,3H-pyrrolo[1,2-c]thiazole;

3-(pyridin-3-yl)-7-(1-N,N-dimethylcarbamoylindol-3-yl)carbonyl-1H,3H-pyrrolo[1,2-c]thiazole;

3-(pyridin-3-yl)-7-(5-phenylmethoxyindol-3-yl)carbonyl-1H,3H-pyrrolo[1,2-c]thiazole;

3-(pyridin-3-yl)-7-(6-phenylmethoxyindol-3-yl)carbonyl-1H,3H-pyrrolo[1,2-c]thiazole;

3-(pyridin-3-yl)-7-(7-phenylmethoxyindol-3-yl)carbonyl-1H,3H-pyrrolo[1,2-c]thiazole;

3-(pyridin-3-yl)-7-(1-N,N-dimethylcarbamoyl-5-phenylmethoxyindol-3-yl)carbonyl- 1H,3H-pyrrolo[1,2-c]thiazole;

3-(pyridin-3-yl)-7-(1-N,N-dimethylcarbamoyl-6-phenylmethoxyindol-3-yl)carbonyl- 1H,3H-pyrrolo[1,2-c]thiazole;

3-(pyridin-3-yl)-7-(1-N,N-dimethylcarbamoyl-7-phenylmethoxyindol-3-yl)carbonyl- 1H,3H-pyrrolo[1,2-c]thiazole;

3-(pyridin-3-yl)-7-(1-tert-butyloxycarbonylindol-3-yl)carbonyl-1H,3H-pyrrolo[1,2-c]thiazole;

3-(pyridin-3-yl)-7-(67-phenylindol-3-yl)carbonyl-1H,3H-pyrrolo[1,2-c]thiazole;

3-(pyridin-3-yl)-7-(1-N,N-dimethylcarbamoyl-6-phenylindol-3-yl)carbonyl- 1H,3H-pyrrolo[1,2-c]thiazole;

2-oxide-3-(pyridin-3-yl)-7-(1-tert-butyoxycarbohylindol-3-ylcarbonyl)- 1H,3H-pyrrolo[1,2-c]thiazole;

2-oxide-3-(pyridin-3-yl)-7-(indol-3-ylcarbonyl)-1H,3H-pyrrolo[1,2-c]thiazole;

3-(pyridin-3-yl)-7-(1-N,N-diisopropylcarbamoyl-6-phenylmethoxyindol- 3-ylcarbonyl)-1H,3H-pyrrolo[1,2-c]thiazole;

1,1-dimethyl-3-(pyridin-3-yl)-7-(indol-3-ylcarbonyl)-1H,3H-pyrrolo[1,2-c]thiazole;

3-(pyridin-3-yl)-7-(1-carbomethoxycarbamoyl-6-phenylmethoxyindol-3-ylcarbonyl)- 1H,3H-pyrrolo[1,2-c]thiazole;

1,1-dimethyl-3-(pyridin-3-yl)-7-(1-N,N-dimethylcarbamoyl-indol-3-yl-carbonyl)- 1H,3H-pyrrolo[1,2-c]thiazole;

3-(pyridin-3-yl)-7-(1-N-methyl-N-phenylcarbamoyl-6-phenylmethoxyindol- 3-ylcarbonyl)-1H,3H-pyrrolo[1,2-c]thiazole;

3-(pyridin-3-yl)-7-(1-methyl-6-phenylmethoxyindol-3-ylcarbonyl)- 1H,3H-pyrrolo[1,2-c]thiazole;

3-(pyridin-3-yl)-7-(1-N-methylcarbamoyl-6-phenylmethoxyindol-3-yl-carbonyl)- 1H,3H-pyrrolo[1,2-c]thiazole;

2-oxide-3-(pyridin-3-yl)-7-(1-N,N-dimethylcarbamoyl-6-phenylindol-3-ylcarbonyl)- 1H,3H-pyrrolo[1,2-c]thiazole;

1,1-dimethyl-3-(pyridin-3-yl)-7-(1-N,N-dimethylcarbamoyl-6-phenylindol- 3-ylcarbonyl)-1H,3H-pyrrolo[1,2-c]thiazole;

1,1-dimethyl-3-(pyridin-3-yl)-7-[6-(4-methoxyphenyl)indol-3-ylcarbonyl]- 1H,3H-pyrrolo[1,2-c]thiazole;

1,1-dimethyl-3-(pyridin-3-yl)-7-[1-N,N-dimethylcarbamoyl- 6-(4-methoxyphenyl)indol-3-ylcarbonyl]-1H,3H-pyrrolo[1,2-c]thiazole;

3-(pyridin-3-yl)-7-(1-carbophenoxy-6-phenylmethoxyindol-3-ylcarbonyl)- 1H,3H-pyrrolo[1,2-c]thiazole;

3-(pyridin-3-yl)-7-[6-(4-fluorophenyl)indol-3-ylcarbonyl]- 1H,3H-pyrrolo[1,2-thiazole;

3-(pyridin-3-yl)-7-[1-N,N-dimethylcarbamoyl-6-(4-fluorophenyl)indol- 3-ylcarbonyl]-1H,3H-pyrrolo[1,2-c]thiazole;

3-(pyridin-3-yl)-7-(1-N-methylcarbamoyl-6-phenylindol-3-ylcarbonyl)- 1H,3H-pyrrolo[1,2-c]thiazole;

3-(pyridin-3-yl)-7-[1-N-methylcarbamoyl-6-(4-fluorophenyl)indol-3-yl-carbonyl]- 1H,3H-pyrrolo[1,2-c]thiazole;

1,1-dimethyl-3-(pyridin-3-yl)-7-[1-N-methylcarbamoyl-6-(4-methoxyphenyl)indol-3-ylcarbonyl]-1H,3H-pyrrolo[1,2-c]thiazole;

3-(1-methylpyridin-3-yl)-7-(1-N,N-dimethylcarbamoyl-6-phenylinol-3-ylcarbonyl)- 1H,3H-pyrrolo[1,2-c]thiazole;

3-(1-oxide-pyridin-3-yl)-7-(1-N,N-dimethylcarbamoyl-6-phenylindol-3-ylcarbonyl)- 1H,3H-pyrrolo[1,2-c]thiazole;

3-(1-oxide-pyridin-3-yl)-7-(1-N-methylcarbamoyl-6-phenylindol-3-ylcarbon)- 1H,3H-pyrrolo[1,2-c]thiazole;

1,1-dimethyl-3-(pyridin-3-yl)-7-[6-(4-fluorophenyl)indol-3-ylcarbonyl]- 1H,3H-pyrrolo[1,2-c]thiazole;

3-(pyridin-3-yl)-7-(1-N-methylcarbamoyl-6-phenylmethoxyindol-3-ylcarbonyl)- 1H,3H-pyrrolo[1,2-c]thiazole;

3-(pyridin-3-yl)-7-[6-(4-methoxyphenyl)indol-3-yl]carbonyl- 1H,3H-pyrrolo[1,2-c]thiazole;

3-(1-oxide-pyridin-3-yl)-7-[1-N,N-dimethylcarbamoyl-6-(4-fluorophenyl)indol- 3-ylcarbonyl]-1H,3H-pyrrolo[1,2-c]thiazole;

3-(pyridin-3-yl)-7-[1-N,N-dimethylcarbamoyl-6-(4-methoxyphenyl)indol- 3-ylcarbonyl]-1H,3H-pyrrolo[1,2-c]thiazole;

3-(pyridin-3-yl)-7-[1-N-methylcarbamoyl-6-(4-methoxyphenyl)indol- 3-ylcarbonyl]-1H,3H-pyrrolo[1,2-c]thiazole;

3-(1-oxide-pyridin-3-yl)-7-(1-N,N-dimethylcarbamoylindol-3-ylcarbonyl)- 1H,3H-pyrrolo[1,2-c]thiazole;

3-(1-oxide-pyridin-3-yl)-7-[1-N,N-dimethylcarbamoyl-6-(4-methoxyphenyl)indol- 3-ylcarbonyl]-1H,3H-pyrrolo[1,2-c]thiazole;

3-(pyridin-3-yl)-7-[1-(2-carbomethoxyethyl)-6-(4-fluorophenyl)indol- 3-ylcarbonyl]-1H,3H-pyrrolo[1,2-c]thiazole;

3-(pyridin-3-yl)-7-(6-chloroindol-3-ylcarbonyl)-1H,3H-pyrrolo[1,2-c]thiazole;

3-(pyridin-3-yl)-7-[1-N,N-dimethylcarbamoyl-6-(3,4,5-trimethoxyphenyl)indol- 3-ylcarbonyl]-1H,3H-pyrrolo[1,2-c]thiazole;

3-(pyridin-3-yl)-7-[1-(2-carboxyethyl)-6-(4-fluorophenyl)indol- 3-ylcarbonyl]- 1H,3H-pyrrolo[1,2-c]thiazole;

3-(pyridin-3-yl)-7-[1-(2-sulfamylethyl)-6-(4-fluorophenyl)indol- 3-ylcarbonyl]- 1H,3H-pyrrolo[1,2-c]thiazole;

3-(pyridin-3-yl)-7-[1-methanesulfonyl-6-(4-fluorophenyl)indol- 3-ylcarbonyl]- 1H,3H-pyrrolo[1,2-c]thiazole;

3-(pyridin-3-yl)-7-(1-N,N-dimethylcarbamoyl-6-phenylindol-3-ylcarbonyl)- 1H,3H-pyrrolo[1,2-c]thiazole Hydrochloride;

3-(pyridin-3-yl)-7-[1-(2-N,N-dimethylcarbamoylmethyl)-6-(4-fluorophenyl)indol- 3-ylcarbonyl]-1H,3H-pyrrolo[1,2-c]thiazole;

3-(1-oxide-pyridin-3-yl)-7-(1-N,N-dimethylcarbamoyl-6-phenylindol-3-ylcarbonyl)- 1H,3H-pyrrolo[1,2-c]thiazole hydrochloride;

3-(pyridin-3-yl)-7-[1-N,N-dimethylsulfamyl-6-(4-fluorophenyl)indol- 3-ylcarbonyl]-1H,3H-pyrrolo[1,2-c]thiazole;

3-(pyridin-3-yl)-7-[1-N,N-dimethylcarbamoyl-6-(3-aminophenyl)indol-3-ylcarbonyl]- 1H,3H-pyrrolo[1,2-c]thiazole;

3-(pyridin-3-yl)-7-[1-(2-tert-butoxycarbonylaminoethyl)-6-(4-fluorophenyl)indol- 3-ylcarbonyl]-1H,3H-pyrrolo[1,2-c]thiazole;

3-(1-oxide-pyridin-3-yl)-7-(1-methyl-6-phenylmethoxyindol-3-ylcarbonyl)- 1H,3H-pyrrolo[1,2-c]thiazole;

3-(pyridin-3-yl)-7-[1-(2-aminoethyl)-6-(4-fluorophenyl)indol-3-ylcarbonyl]- 1H,3H-pyrrolo[1,2-c]thiazole;

3-(1-oxide-pyridin-3-yl)-7-[1-N,N-dimethylsulfamyl-6-(4-fluorophenyl)indol- 3-ylcarbonyl]-1H,3H-pyrrolo[1,2c]thiazole;

3-(pyridin-3-yl)-7-[1-phenylsulfonyl-6-(4-fluorophenyl)indol-3-ylcarbonyl]- 1H,3H-pyrrolo[1,2-c]thiazole;

3-(pyridin-3-yl)-7-[1-N-(2-hydroxyethyl)carbamoyl-6-(4-fluorophenyl)indol- 3-ylcarbonyl]-1H,3H-pyrrolo[1,2-c]thiazole;

3-(pyridin-3-yl)-7-(6-bromoindol-3-ylcarbonyl)-1H,3H-pyrrolo[1,2-c]thiazole;

3-(pyridin-3-yl)-7-(1-N,N-dimethylcarbamoyl-6-bromoindol-3-ylcarbonyl)- 1H,3H-pyrrolo[1,2-c]thiazole;

3-(pyridin-3-yl)-7-(1-N,N-dimethylcarbamoyl-6-chloroindol-3-ylcarbonyl)- 1H,3H-pyrrolo[1,2-c]thiazole;

3-(1-oxide-Pyridin-3-yl)-7-(1-N,N-dimethylcarbamoyl-6-chloroindol- 3-ylcarbonyl)-1H,3H-pyrrolo[1,2-c]thiazole;

3-(1-amino-pyridin-3-yl)-7-[1-N,N-dimethylcarbamoyl-6-(4-fluorophenyl)indol- 3-ylcarbonyl]-1H,3H-pyrrolo[1,2-c]thiazole;

3-(pyridin-3-yl)-7-[1-(2-methanesulfonylaminoethyl)-6-(4-fluorophenyl)indol-3-ylcarbonyl]-1H,3H-pyrrolo[1,2-c]thiazole;

3-(pyridin-3-yl)-7-[1-hydrazinocarbonyl-6-(4-fluorophenyl)indol-3-yl-carbonyl]- 1H,3H-pyrrolo[1,2-c]thiazole;

3-(pyridin-3-yl)-7-[1-(2-aminoethyl)-6-(4-fluorophenyl)indol-3-ylcarbonyl]- 1H,3H-pyrrolo[1,2-c]thiazole Hydrochloride;

3-(pyridin-3-yl)-7-[1-ethanesulfonyl-6-(4-fluorophenyl)indol- 3-ylcarbonyl]- 1H,3H-pyrrolo[1,2-c]thiazole;

3-(pyridin-3-yl)-7-[1-(2-hydroxyethyl)-6-(4-fluorophenyl)indol-3-ylcarbonyl]- 1H,3H-pyrrolo[1,2-c]thiazole;

3-(1-oxide-pyridin-3-yl)-7-[1-phenylsulfonyl-6-(4-fluorophenyl)indol- 3-ylcarbonyl]-1H,3H-pyrrolo[1,2-c]thiazole;

3-(1-oxide-pyridin-3-yl)-7-[1-(2-N,N-dimethylcarbamoylmethyl)- 6-(4-fluorophenyl)indol-3-ylcarbonyl]-1H,3H-pyrrolo[1,2-c]thiazole;

3-(pyridin-3-yl)-7-[1-carbamoyl-6-(4-fluorophenyl)indol-3-ylcarbonyl]-1H,3H-pyrrolo[1,2-c]thiazole;

3-(1-carbamoylamino-pyridin-3-yl)-7-[1-N,N-dimethylcarbamoyl-6(4-fluorophenyl)indol-3-ylcarbonyl]-1H,3H-pyrrolo[1,2-c]thiazole;

3-(1-oxide-pyridin-3-yl)-7-[1-(2-aminosulfonylethyl)-6-(4-fluorophenyl)indol-3-ylcarbonyl]-1H,3H-pyrrolo[1,2-c]thiazole;

3-(pyridin-3-yl)-7-[1-N,N-dimethylcarbamoyl-6-(3-aminosulfonylphenyl)indol-3-ylcarbonyl]-1H,3H-pyrrolo[1,2-c]thiazole;

3-(pyridin-3-yl)-7-[1-(2-N-methylcarbamoylmethyl)-6-(4-fluorophenyl)indol-3-ylcarbonyl]-1H,3H-pyrrolo[1,2-c]thiazole;

3-(pyridin-3-yl)-7-[1-N,N-dimethylcarbamoyl-6-(4-fluorophenyl)indol-3-ylcarbonyloxime]-1H,3H-pyrrolo[1,2-c]thiazole;

3-(pyridin-3-yl)-7-[1-(N-methyl-N-(dimethylaminoethyl)carbamoyl-6-(4-fluorophenyl)indol-3-ylcarbonyl]-1H,3H-pyrrolo[1,2-c]thiazole;

3-(pyridin-3-yl)-7-[1N-carboxymethylcarbamoyl-6-(4-fluorophenyl)indol-3-ylcarbonyl]-1H,3H-pyrrolo[1,2-c]thiazole;

3(1-methyl-pyridin-3-yl)-7-[1-N,N-dimethylcarbamoyl-6-(4-fluorophenyl)indol-3-ylcarbonyl]-1H,3H-pyrrolo[1,2-c]thiazole;

3-(pyridin-3-yl)-7-[1-N-sulfoethylcarbamoyl-6-(4-fluorophenyl)indol-3-ylcarbonyl]-1H,3H-pyrrolo[1,2-c]thiazole;

3-(1-oxide-pyridin-3-yl)-7-[1-(2-aminoethyl)-6-(4-fluorophenyl)indol-3-ylcarbonyl]-1H,3H-pyrrolo[1,2-c]thiazole;

3-(1-oxide-pyridin-3-yl)-7-[1-N,N-dimethylcarbamoyl-6-(4-hydrazinylcarbonylphenyl)indol-3-ylcarbonyl]-1H,3H-pyrrolo[1,2-thiazole;

3-(1-acetoxymethylpyridin-3-yl)-7-[1-N,N-dimethylcarbamoyl-6-(4-fluorophenyl)indol-3-ylcarbonyl]-1H,3H-pyrrolo[1,2]-c]thiazole;

3-(pyridin-3-yl)-7-[1-N-methyl-N-hydroxymethylcarbamoyl-6-(4-fluorophenyl)indol-3-ylcarbonyl]-1H,3H-pyrrolo[1,2-c]thiazole;

3-(pyridin-3-yl)-7-[1-cyanomethyl-6-(4-fluorophenyl)indol-3-ylcarbonyl]-1H,3H-pyrrolo[1,2-c]thiazole;

3-(pyridin-3-yl)-7-[1-carbamoylmethyl-6-(4-fluorophenyl)indol-3-ylcarbonyl]-1H,3H-pyrrolo[1,2-c]thiazole;

3-(pyridin-3-yl)-7-[1-carboxymethyl-6-(4-fluorophenyl)indol-3-ylcarbonyl]-1H,3H-pyrrolo[1,2-c]thiazole;

3-(pyridin-3-yl)-7-[1-N-sulfoethylcarbamoyl-6-(4-fluorophenyl)indol-3-ylcarbonyl]-1H,3H-pyrrolo[1,2-c]thiazole;

3-(pyridin-3-yl)-7-[1-N-sulfoethylcarbamoyl-6-(4-fluorophenyl)indol-3-ylcarbonyl]-1H,3H-pyrrolo[1,2-c]thiazole;

3-(pyridin-3-yl)-7-(1-N,N-dimethylcarbamoyl-6-(4-hydroxymethyl)phenylindol-3-ylcarbonyl)-1H,3H-pyrrolo[1,2-c]thiazole;

2-oxide-3-(1-oxide-pyridin-3-yl)-7-(1-N,N-dimethylcarbamoyl-6-(4-fluorophenyl)indol-3-ylcarbonyl]-1H,3H-pyrrolo[1,2-c]thiazole;

5. A pharmaceutical composition useful for inhibiting PAF in a mammal in need of such treatment comprising a PAF-inhibitive effective amount of a compound as defined by claim 1 in combination with a pharmaceutically acceptable carrier.

6. A method of inhibiting PAF activity in a mammal in need of such treatment comprising administering a PAF-inhibitive effective amount of a compound as defined by claim 1.

7. A compound having the name 3-(1-acetoxymethylpyridin-3-yl)-7-[1-N,N-dimethylcarbamoyl-6-(4-fluorophenyl)indol-3-ylcarbonyl]-1H,3H-pyrrolo[1,2-c]thiazole or a pharmaceutically acceptable salt thereof.

* * * * *

UNITED STATES PATENT AND TRADEMARK OFFICE
CERTIFICATE OF CORRECTION

PATENT NO. : 5,459,152  
DATED : October 17, 1995  
INVENTOR(S) : J. B. Summers, et. Al.

Page 1 of 2

It is certified that error appears in the above-indentified patent and that said Letters Patent is hereby corrected as shown below:

In the abstract, line 3, change "oxazole" to --oxazoline--.

Column 72, line 29, change "sic" to --six--.

Column 73, between lines 6-7, insert -- $-(CH_2)_p CN$ where p is as defined above;--.

Column 73, line 13, change "$R^{3l}$" to --$R^3$--.

Column 73, line 21, change "$N^+$" to --N+--.

Column 73, line 41, change "defied" to --defined--.

Column 73, line 50, change "$-(CH_2)_r$ phenyl" to -- $-(CH_2)_r$-phenyl--.

Column 74, line 26, change "67" to --6--.

Column 74, line 30, change "butyoxycarbohylindol" to --butoxycarbonyl indol--.

Column 74, line 61, change "yl)" to --(pyridin-3-yl)--.

Column 75, line 3, change "[1,2-thiazole" to --[1,2-c]thiazole--.

Column 75, line 22, change "ylcarbon" to --ylcarbonyl--.

Column 77, line 22, change "1N" to --1-N--.

Column 77, line 25, change "3" to --3- --.

UNITED STATES PATENT AND TRADEMARK OFFICE
CERTIFICATE OF CORRECTION

PATENT NO. : 5,459,152  Page 2 of 2
DATED : October 17, 1995
INVENTOR(S) : J. B. Summers, et. Al.

It is certified that error appears in the above-indentified patent and that said Letters Patent is hereby corrected as shown below:

Column 77, line 37, change "[1,2-thiazole" to --[1,2-c]thiazole--.

Column 77, line 40, change "[1,2]-c]" to --[1,2-c]--.

Column 78, line 24, change "indol" to --indole--.

Column 78, line 25, after "thiazole;" insert --or a pharmaceutically acceptable salt therof.--.

Signed and Sealed this

Twenty-ninth Day of April, 1997

Attest:

BRUCE LEHMAN

Attesting Officer  Commissioner of Patents and Trademarks